United States Patent [19]

Matsuo et al.

[11] Patent Number: 5,187,156
[45] Date of Patent: Feb. 16, 1993

[54] PEPTIDE COMPOUNDS, PROCESSES FOR PREPARATION THEREOF AND PHARMACEUTICAL COMPOSITION COMPRISING THE SAME

[75] Inventors: Masaaki Matsuo, Toyonaka; Daijiro Hagiwara, Moriguchi; Hiroshi Miyake, Kyoto, all of Japan

[73] Assignee: Fujisawa Pharmaceutical Co., Ltd., Osaka, Japan

[21] Appl. No.: 317,858

[22] Filed: Mar. 2, 1989

[30] Foreign Application Priority Data

Mar. 16, 1988 [GB] United Kingdom ................ 8806193
Oct. 28, 1988 [GB] United Kingdom ................ 8825323
Jan. 30, 1989 [GB] United Kingdom ................ 8901964

[51] Int. Cl.$^5$ ..................... A61K 37/00; C07K 5/00
[52] U.S. Cl. ..................................... 514/18; 530/331; 930/21

[58] Field of Search ................ 514/18, 19; 530/331; 930/21

[56] References Cited

FOREIGN PATENT DOCUMENTS 0018072 10/1980 European Pat. Off. .

OTHER PUBLICATIONS

Mizrahi, Eur. J. Pharm. vol. 99 (1984) 192–202.
Barnes, TIPS (Jan. 1987) (vol. 8) 24–27.

Primary Examiner—Merrell C. Cashion, Jr.
Assistant Examiner—B. Celsa
Attorney, Agent, or Firm—Oblon, Spivak, McClelland, Maier & Neustadt

[57] ABSTRACT

The present invention relates to DTrp-Phe containing tripeptides and pharmaceuticals, which possess tachykinin antagonism activity as well as processes of making such peptides.

5 Claims, No Drawings

PEPTIDE COMPOUNDS, PROCESSES FOR PREPARATION THEREOF AND PHARMACEUTICAL COMPOSITION COMPRISING THE SAME

The present invention relates to new peptide compounds and pharmaceutically acceptable salts thereof.

More particularly, it relates to new peptide compounds and pharmaceutically acceptable salts thereof which have pharmacological activities such as tachykinin antagonism and the like, to processes for preparation thereof, to pharmaceutical composition comprising the same, and to a method of using the same therapeutically in the treatment and the prevention of asthma and the like.

One object of the present invention is to provide new and useful peptide compounds and pharmaceutically acceptable salts thereof which have pharmacological activities such as tachykinin antagonism and the like.

Another object of the present invention is to provide processes for the preparation of said peptide compounds and salts thereof.

A further object of the present invention is to provide a pharmaceutical composition comprising, as an active ingredient, said peptide compounds and pharmaceutically acceptable salts thereof.

Still further object of the present invention is to provide a method for the treatment and the prevention of asthma and the like.

The object compound of the present invention can be represented by the following general formula (I).

$$R^1\text{—}A\text{—}D\text{—}Trp(R^2)\text{—}Phe\text{—}R^3 \qquad (I)$$

wherein $R^1$ is hydrogen or an amino protective group, $R^2$ is hydrogen, an amino protective group, carbamoyl(lower)alkyl, carboxy(lower)alkyl or protected carboxy(lower)alkyl, $R^3$ is ar(lower)alkyl, a group of the formula:

wherein $R^4$ and $R^5$ are each hydrogen, aryl or lower alkyl which may have suitable substituent(s), or $R^4$ and $R^5$ are linked together to form benzene-condensed lower alkylene, or a group of the formula:

wherein $R^6$ is hydrogen, aryl or lower alkyl which may have suitable substituent(s), and A is a single bond or one or two amino acid(s) residue, provided that when A is one amino acid residue of —D—Trp—, then $R^4$ is not hydrogen.

Particularly, the compound represented by the following formula (I') is useful as tachykinin antagonist and the like.

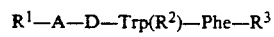

wherein $R^1$ is hydrogen or an amino protective group, $R^2$ is hydrogen, an amino protective group, carbamoyl(lower)alkyl, carboxy(lower)alkyl or protected carboxy(lower)alkyl, $R^3$ is ar(lower)alkyl, a group of the formula:

wherein $R^4$ is hydrogen, aryl or lower alkyl which may have suitable substituent(s), and $R^5$ is aryl or lower alkyl which may have suitable substituent(s), or $R^4$ and $R^5$ are linked together to form benzene-condensed lower alkylene, or a group of the formula:

—OR$^6$ wherein $R^6$ is aryl or lower alkyl which may have suitable substituents(s), and A is a single bond or one or two amino acid(s) residue.

According to the present invention, the new peptide compounds (I) can be prepared by processes which are illustrated in the following schemes.

Process 1

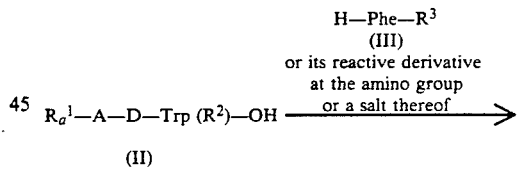

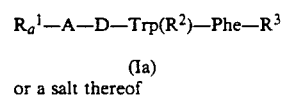

Process 2

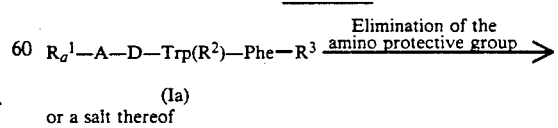

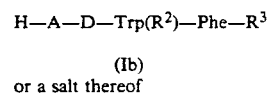

Process 3

H—D—Trp(R²)—Phe—R³

(Ic)
or its reactive derivative
at the amino group or
a salt thereof $R_a^1$—A¹—OH
(IV)
or its reactive derivative
at the carboxy group or
a salt thereof
⟶

$R_a^1$—A¹—D—Trp(R²)—Phe—R³

(Id)
or a salt thereof

Process 4

H—A—D—Trp(R²)—Phe—R³

(Ib)
or its reactive derivative
at the amino group or
a salt thereof

Introduction of the
amino protective group ⟶

$R_a^1$—A—D—Trp(R²)—Phe—R³

(Ia)
or a salt thereof

Process 5

H—A²—D—Trp(R²)—Phe—R³

(Ie)
or its reactive derivative
at the amino group or
a salt thereof $R_a^1$—A³—OH
(V)
or its reactive derivative
at the carboxy group or
a salt thereof
⟶

$R_a^1$—A³—A²—D—Trp(R²)—Phe—R³

(If)
or a salt thereof

Process 6

R¹—A—D—Trp($R_a^2$)—Phe—R³

(Ig)
or a salt thereof

Elimination of the
carboxy protective group ⟶

R¹—A—D—Trp($R_b^2$)—Phe—R³

(Ih)
or a salt thereof

Process 7

R¹—A⁴—D—Trp(R²)—Phe—R³

(Ii)
or a salt thereof

Elimination of the amino,
hydroxy or carboxy
protective group ⟶

R¹—A⁵—D—Trp(R²)—Phe—R³

(Ij)
or a salt thereof

Process 8

R¹—A—D—Trp($R_c^2$)—Phe—R³

(Ik)
or a salt thereof

Elimination of the amino
protective group ⟶

R¹—A—D—Trp—Phe—R³

(Il)
or a salt thereof

Process 9

R¹—A—D—Trp(R²)—Phe—$OR_a^6$ (Im)
or a salt thereof

Elimination of $R_a^6$ ⟶

R¹—A—D—Trp(R²)—Phe—OH (In)
or a salt thereof

Process 10

R¹—A—D—Trp(R²)—Phe—N⟨$R_a^4$/R⁵

(Io)
or a salt thereof

Elimination of the hydroxy
protective group ⟶

R¹—A—D—Trp(R²)—Phe—N⟨$R_b^4$/R⁵

(Ip)
or a salt thereof

Process 11

R¹—A—D—Trp(R²)—Phe—OR⁶

(Iq)
or a salt thereof

HN⟨R⁴/R⁵
(VI)
⟶

R¹—A—D—Trp(R²)—Phe—N⟨R⁴/R⁵

(Ir)
or a salt thereof

Process 12

$R_b^1$—A—D—Trp(R²)—Phe—R³

(Is)
or a salt thereof

Elimination of the carboxy
protective group ⟶

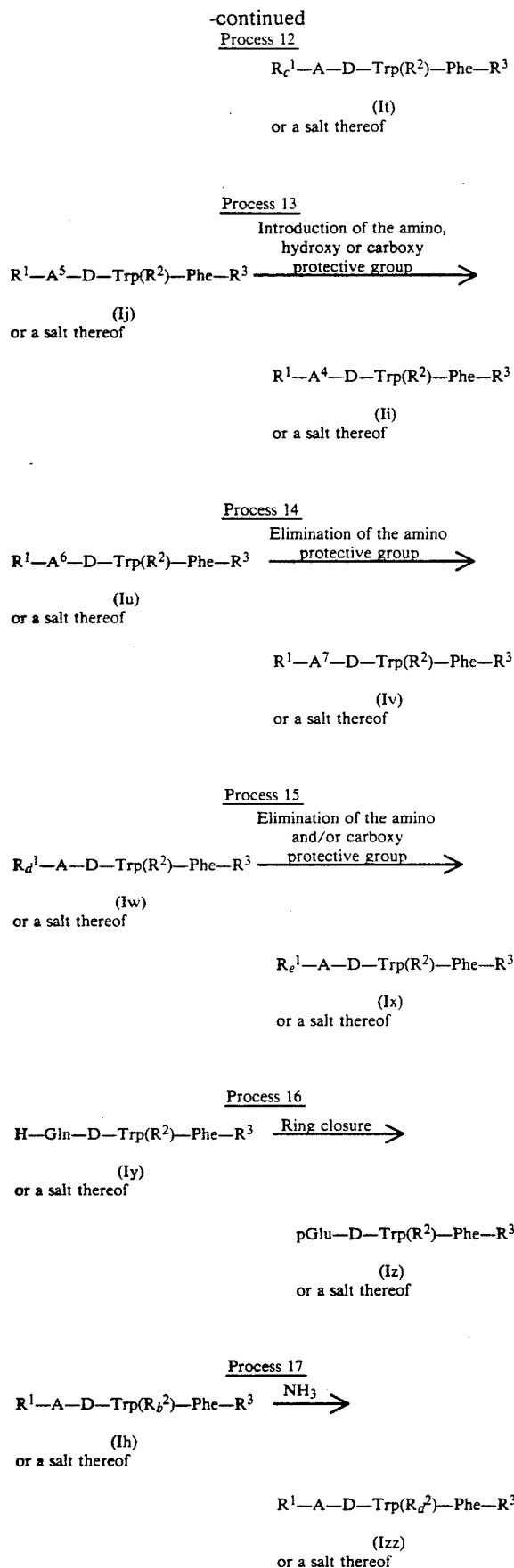

wherein
R$^1$, R$^2$, R$^3$, R$^4$, R$^5$, R$^6$ and A are each as defined above, R$_a^1$ and R$_c^2$ are each an amino protective group, R$_b^1$ is an amino protective group containing a protected carboxy, R$_c^1$ is an amino protective group containing a carboxy, R$_d^1$ is an amino protective group containing an amino group which is substituted by an amino protective group and additionally a protected carboxy(lower)alkyl or an ar(lower)alkyl, R$_e^1$ is an amino protective group containing an amino group which is substituted by a carboxy(lower)alkyl or an ar(lower) alkyl, R$_a^2$ is protected carboxy(lower)alkyl, R$_b^2$ is carboxy(lower)alkyl, R$_d^2$ id carbamoyl(lower)alkyl, R$_a^4$ is protected hydroxy(lower)alkyl, R$_b^4$ is hydroxy(lower)alkyl, R$_a^6$ is lower alkyl which may have suitable substituent(s), A$^1$ is one or two amino acid(s) residue, A$^2$ and A$^3$ are each an amino acid residue, A$^4$ is one or two amino acid(s) residue containing a protected hydroxy group, a protected amino group, a protected imino group or a protected carboxy group, A$^5$ is one or two amino acid(s) residue containing a hydroxy group, an amino group, an imino group or a carboxy group, A$^6$ is one or two amino acid(s) residue which is substituted by acyl having protected amino, and A$^7$ is one or two amino acid(s) residue which is substituted by acyl having amino.

As to the starting compounds (II), (III), (IV) and (V) some of them are novel and can be prepared by the procedures described in the Preparation 1 to 22 mentioned later or a conventional manner.

Throughout the present specification, the amino acids, peptides, protective groups, condensing agents, etc. are indicated by the abbreviations according to the IUPAC-IUB (Commission on Biological Nomenclature) which are in common use in the field of art.

Moreover, unless otherwise indicated, the amino acids and their residues when shown by such abbreviations are meant to be L-configured compounds and residues, while the D-configured compounds and residues are shown with the prescript of D-.

Suitable pharmaceutically acceptable salts of the object compounds (I) are conventional non toxic salt and include an acid addition salt such as an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydriodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention include within the scope thereof are explained in detail as follows.

The term "lower" is intended to mean 1 to 6, preferably 1 to 4 carbon atom(s), unless otherwise indicated.

Suitable "one or two amino acid(s) residue" means a bivalent residue derived from one or two amino acid(s), and such amino acid may be neutral amino acid such as glycine (Gly), D- or L- alanine (Ala), β-alanine (β-Ala), D- or L-valine (Val), D- or L- leucine (Leu), D- or L-isoleucine (Ile), D- or L- serine (Ser), D- or L-threonine (Thr), D- or L- cysteine (Cys), D- or L-methionine (Met), D- or L- phenylalanine (Phe), D- or L-tryptophan (Trp), D- or L- tyrosine (Tyr), D- or L-proline (Pro), D- or L- 4-hydroxyproline (Hyp), D- or L-pyroglutamic acid (pGlu), acidic amino acid such as D- or L- glutamic acid (Glu), D- or L- aspartic acid (Asp), D- or L- β-aspartic acid (βAsp), D- or L- glutamine (Gln), D- or L- asparagine (Asn), and basic amino acid such as D- or L- lysine (Lys), D- or L- arginine (Arg), D- or L-histidine (His), D- or L- ornithine (Orn), and combination of two of such amino acid, whose side chains, which are amino, hydroxy, thiol or carboxy groups, may be substituted by the suitable substituent(s) such as di(lower)alkylamino (e.g., dimethylamino, etc.), trihalo(lower)alkoxycarbonyl (e.g., 2,2,2-trichloroethoxycarbonyl, etc.), ar(lower)alkoxycarbonyl (e.g., benzyloxycarbonyl, etc.), arenesulfonyl (e.g., benzenesulfonyl, toluenesulfonyl, etc.), haloar(lower)alkoxycarbonyl (e.g., o-chlorobenzyloxycarbonyl, etc.), ar(lower)alkyl (e.g., benzyl, phenethyl, etc.), trihalo(lower)alkyl (e.g., 2,2,2-trichroroethyl, etc.), carboxy(lower)alkanoyl (e.g., carboxyacetyl, carboxypropionyl, etc.), glycyl, β-alanyl, N-lower alkoxycarbonylglycyl (e.g., N-t-butoxycarbonylglycyl, etc.) and N-lower alkoxycarbonyl- β-alanyl (e.g., N-t-butoxycarbonylglycyl, etc.), or usual protecting group used in the field of amino acid and peptide chemistry such as those mentioned below.

Suitable "an amino acid residue" means a bivalent residue derived from the amino acid as mentioned above.

As to the formula "—Trp($R^2$)—", it means the group $R^2$ being substituted at 1-position of indole group in tryptophan residue.

Suitable "amino protective group" may include a conventional protective group, which is used in the field of amino acid and peptide chemistry, that is may be ar(lower)alkyl (e.g. trityl, benzhydryl, benzyl, etc.), dinitrophenyl, lower alkoxycarbonyl(lower)alkenyl (e.g. 1-methoxycarbonyl-1-propen-2-yl, etc.), aroyl(lower)alkenyl (e.g. 1-benzoyl-1-propen-2-yl, etc.), hydroxyar(lower)alkylidene (e.g. 2-hydroxybenzylidene, etc.), silyl compound such as tri(lower)alkylsilyl (e.g. trimethylsilyl, etc.), acyl as mentioned below, or the like.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as carbamoyl, lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, t-butoxycarbonyl, etc.), lower alkenoyl (e.g. acryloyl, methacryloyl, crotonoyl, etc.), ($C_3$-$C_7$)-cycloalkanecarbonyl (e.g. cyclohexanecarbonyl, etc.), amidino, protected carboxycarbonyl such as lower alkoxalyl (e.g. methoxalyl, ethoxalyl, t-butoxalyl, etc.), and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, morpholinocarbonyl, etc.), and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as carboxy, lower alkyl (e.g. methyl, ethyl, propyl, isopropyl, butyl, t-butyl, pentyl hexyl, etc.), halogen (e.g. chlorine, bromine, iodine, fluorine), carbamoyl, amino which may be substituted by suitable substituent(s) such as lower alkanoyl (e.g. formyl, acetyl, propionyl, etc.), ar(lower)alkyl (e.g. benzyl, etc.), lower alkyl (e.g. methyl, ethyl, propyl, isopropyl, butyl, t-butyl, etc.), lower alkoxycarbonyl (e.g. methoxycarbonyl, ethoxycarbonyl, t-butoxycarbonyl, etc.), carboxy(lower)alkyl (e.g. carboxymethyl, carboxyethyl, etc.), protected carboxy(lower)alkyl (e.g. t-butoxycarbonylmethyl, etc.) and the like.

Suitable "carbamoyl(lower)alkyl" may include carbamoylmethyl, carbamoylethyl, carbamoylpropyl, and the like.

Suitable "carboxy(lower)alkyl" may include carboxymethyl, carboxyethyl, carboxypropyl, and the like.

Suitable "protected carboxy(lower)alkyl" means the above-mentioned carboxy(lower)alkyl, in which the carboxy group is protected by a conventional protective group such as esterified carboxy group. Preferred example of the ester moiety thereof may include lower alkyl ester (e.g. methyl ester, ethyl ester, propyl ester, etc.) and the like.

Suitable "aryl" may include phenyl, tolyl, xylyl, naphthyl, and the like.

Suitable "lower alkyl which may have suitable substituent(s)" may include a conventional group, which is used in the field of amino acid and peptide chemistry, such as lower alkyl (e.g., methyl, ethyl, propyl isopropyl, butyl, tert-butyl, cyclohexyl, etc.), hydroxy(lower)alkyl (e.g. hydroxymethyl, hydroxyethyl, etc.), protected hydroxy(lower)alkyl such as acyloxy(lower)alkyl (e.g. benzyloxycarbonyloxymethyl, benzyloxycarbonyloxyethyl, etc.), substituted or unsubstituted ar(lower)alkyl (e.g., trityl, benzyl, phenethyl, halogen substituted ar(lower)alkyl such as o-fluorobenzyl, p-chlorobenzyl, p-nitrobenzyl, etc.), heterocyclic(lower)alkyl, for instance, pyridyl(lower)alkyl (e.g., 2-pyridylmethyl, 3-pyridylmethyl, 4-pyridylmethyl, etc.) and the like.

Suitable "lower alkyl" may include a straight or branched one such as methyl, ethyl, propyl, isopropyl, butyl, isobutyl, tert-butyl, pentyl, hexyl, and the like.

Suitable "ar(lower)alkyl" may include trityl, benzhydryl, benzyl, phenethyl, and the like.

Suitable group of the formula:

in which R⁴ and R⁵ are linked together to form benzene-condensed lower alkylene, may include 1-indolinyl, 2-isoindolinyl, 1,2,3,4-tetrahydroquinolin-1-yl-, 1,2,3,4-tetrahydroisoquinolin-2-yl, and the like.

Suitable "amino protective group containing a protected carboxy" may include a protected carboxycarbonyl (e.g methoxalyl, ethoxalyl, t-butoxalyl, etc.), and the like.

Suitable "amino protective group containing a carboxy" may include carboxycarbonyl, and the like.

Suitable "amino protective group containing an amino group which is substituted by an amino protective group and additionally a protected carboxy(lower)alkyl or an ar(lower)alkyl" may include N-lower alkoxycarbonyl-N-lower alkoxycarbonyl(lower)alkylamino(lower)alkanoyl (e.g. N-t-butoxycarbonyl-N-t-butoxycarbonylmethylaminoacetyl, etc.), N-lower alkoxycarbonyl-N-ar(lower)alkylamino(lower)alkanoyl (e.g. N-t-butoxycarbonyl-N-benzylaminoacetyl, etc.), and the like.

Suitable "an amino protective group containing an amino group which is substituted by a carboxy(lower)alkyl or an ar(lower)alkyl" may include carboxy(lower)alkylamino(lower)alkanoyl (e.g. carboxymethylaminoacetyl, etc.), ar(lower)alkylamino(lower)alkanoyl (e.g. benzylaminoacetyl, etc.), and the like.

Suitable "hydroxy(lower)alkyl" may include hydroxymethyl, hydroxyethyl, hydroxypropyl, and the like.

Suitable "protected hydroxy(lower)alkyl" means the above-mentioned hydroxy(lower)alkyl, in which the hydroxy group is protected by a conventional protective group. Preferred example of the protective group may include aforesaid acyl (e.g. benzyloxycarbonyl, etc.), ar(lower)alkyl (e.g. benzyl, etc.) and the like.

Suitable "one or two amino acid(s) residue containing a hydroxy group, an amino group, an imino group or a carboxy group" may include bivalent residue of an amino acid such as Thr, His, Lys, Orn, Trp, Arg, Glu, and the like, and the bivalent residue of two amino acid(s) in which one of said amino acids is Thr, His, Lys, Orn, Trp, Arg, Glu, and the like.

Suitable "one or two amino acid(s) residue containing a protected hydroxy group, a protected amino group, a protected imino group or a protected carboxy group" means the above-mentioned group, in which the hydroxy, amino, imino or carboxy group is protected by a conventional group used in the field of the amino acid chemistry such as the ar(lower)alkyl or amino-protected group mentioned above.

Suitable "one or two amino acid(s) residue which is substituted by acyl having amino" means a bivalent residue derived from one or two amino acid(s), whose side chain is substituted by acyl having amino such as amino(lower)alkanoyl (e.g. aminoacetyl, aminopropionyl, etc.).

Suitable "one or two amino acid(s) residue which is substituted by acyl having protected amino" means a bivalent residue derived from one or two amino acid(s), whose side chain is substituted by acyl having protected amino. Such acyl group means the above mentioned group, and is protected by the amino protected group mentioned above.

Particularly, the preferred embodiments of R¹, R², R³, R⁴, R⁵, R⁶ and A are as follows.

R¹ is hydrogen: or
acyl, for example, carbamoyl;
lower alkoxycarbonyl (e.g. methoxycarbonyl, ethoxycarbonyl, t-butoxycarbonyl, etc.); lower alkanoyl (e.g. formyl, acetyl, propionyl, butyryl, etc);
ar(lower)alkoxycarbonyl such as mono or di or triphenyl(lower)alkoxycarbonyl (e.g. benzyloxycarbonyl, etc.), etc.;
carbamoyl(lower)alkanoyl (e.g. carbamoylacetyl, succinamoyl, etc.);
lower alkoxalyl (e.g. methoxalyl, t-butoxalyl, etc.); di(lower)alkylamino(lower)alkanoyl (e.g. dimethylaminoacetyl, diethylaminoacetyl, diethylaminopropionyl, etc.);
N-ar(lower)alkyl-N-lower alkoxycarbonylamino(lower)alkanoyl such as N-mono or di or triphenyl(lower)alkyl-N-lower alkoxycarbonylamino(lower)alkanoyl (e.g. N-benzyl-N-t-butoxycarbonylaminoacetyl, etc.), etc.; heterocyclic (lower)alkanoyl optionally substituted with acylamino such as tetrazolyl(lower)alkanoyl (e.g. tetrazolylacetyl, etc.), acylaminothiazolyl(lower)alkanoyl which may have acylamino on the alkanoyl moiety, for instance, lower alkanoylaminothiazolyl(lower)alkanoyl (e.g. formamidothiazolylacetyl, etc.), lower alkanoylaminothiazolyl(lower)alkanoyl having lower alkoxycarbonylamino or lower alkanoylamino on the alkanoyl moiety (e.g. 2-formamidothiazolyl-2-t-butoxycarbonylaminoacetyl, 2-formamidothiazolyl-2-acetamidoacetyl, etc.) , etc.; carboxy(lower)alkanoyl (e.g. oxalo, carboxyacetyl, carboxypropionyl, carboxybutyryl, carboxyvaleryl, etc.);
hydroxy(lower)alkanoyl (e.g. hydroxyacetyl, etc.); heterocyclic carbonyl such as morpholinecarbonyl (e.g. 4-morpholinecarbonyl, etc.), etc.;
lower alkylcarbamoyl (e.g. methylcarbamoyl, t-butylcarbamoyl, etc.);
carboxy(lower)alkylamino(lower)alkanoyl (e.g. carboxymethylaminoacetyl, etc.);
ar(lower)alkylamino(lower)alkanoyl such as mono or di triphenyl(lower)alkylamino(lower)alkanoyl (e.g. benzylaminoacetyl, etc.), etc.;
N-lower alkoxycarbonyl-N-lower alkoxycarbonyl(lower)alkylamino(lower)alkanoyl (e.g. N-t-butoxycarbonyl-N-t-butoxycarbonylmethylaminoacetyl, etc.); and the like:

R² is hydrogen;
acyl such as lower alkanoyl (e.g. formyl, acetyl, etc.), arenesulfonyl (e.g. benzenesulfonyl, toluenesulfonyl, etc.), etc.;
carbamoyl(lower)alkyl (e.g. carbamoylmethyl, etc.); esterified carboxy(lower)alkyl such as lower alkoxycarbonyl(lower)alkyl (e.g. ethoxycarbonylmethyl, etc.), etc.; or
carboxy(lower)alkyl (e.g. carboxymethyl, etc.);

R³ is ar(lower)alkyl such as mono or di or triphenyl(lower)alkyl (e.g. benzyl, phenethyl, etc.), etc.;

a group of the formula:

wherein $R^4$ is hydrogen;

lower alkyl (e.g. methyl, ethyl, etc.); hydroxy(lower)alkyl (e.g. hydroxymethyl, hydroxyethyl, etc.); or acyloxy(lower)alkyl such as phenyl(lower)alkoxycarbonyloxy(lower)alkyl (e.g. benzyloxycarbonyloxyethyl, etc.), etc.;

$R^5$ is aryl (e.g. phenyl, tolyl, xylyl, etc.); ar(lower)alkyl such as mono or di or triphenyl(lower)alkyl (e.g. benzyl, phenethyl, etc.), etc.; or haloar(lower)alkyl such as halo-substituted mono or di or triphenyl(lower)alkyl (e.g. fluorobenzyl, etc.), etc.;

$R^4$ and $R^5$ are linked together to form benzene-condensed lower alkylene (e.g. 1-indolinyl, 1,2,3,4-tetrahydroquinolin-1-yl, 2-isoindolinyl, 1,2,3,4-tetrahydroquinolin-2-yl, etc.);

or a group of the formula:

—$OR^6$ wherein $R^6$ is lower alkyl (e.g. methyl, ethyl, propyl, isopropyl, etc.);

ar(lower)alkyl such as mono or di or triphenyl(lower)alkyl (e.g. benzyl, phenethyl, etc.), etc.;

haloar(lower)alkyl such as halo-substituted mono or di or triphenyl(lower)alkyl (e.g. chlorobenzyl, etc.);

lower cycloalkyl(lower)alkyl (e.g. cyclohexylmethyl, etc.);

heterocyclic lower alkyl such as pyridyl(lower)alkyl (e.g. pyridylmethyl, etc.), etc.;

A is one or two amino acid residue(s) derived from one or amino acid such as glutamine, serine, asparagine, glutamic acid, threonine, lysine, histidine, β-aspartic acid, ornithine, glycine, tyrosine, tryptophan, hydroxyproline, pyroglutamic acid, β-alanine, $N^5,N^5$-di(lower)alkylglutamine, $N^6$-trihalo(lower)alkoxycarbonyllysine, $N^6$-ar(lower)alkoxycarbonyllysine, $N^\tau$-arenesulfonylhistidine, $N^5$-ar(lower)alkoxycarbonylornithine, $R^6$-haloar(lower)alkoxycarbonyllysine, $O^3$-ar(lower)alkylthreonine, N-lower alkylthreonine, $O^5$-trihalo(lower)alkyl glutamate, $O^3$-carboxy(lower)alkanoylthreonine, $O^3$-glycylthreonine, $O^3$-β-alanylthreonine, $O^3$-(N-lower alkoxycarbonylglycyl)threonine $O^3$-(N-lower alkoxycarbonyl-β-alanyl)threonine, etc., more preferably Gln, Ser, Asn, Thr, D—Gln, Lys, His, βAsp, Orn, Gly, Tyr, D—Trp, Hyp, pGlu, Glu, NMe₂, OTce,
                                    |       |
                                   Glu     Glu Troc  Z    Cl—Z   Tos  Z     Bzl   CO(CH₂)₂COOH
 |    |     |      |   |      |     |
Lys, Lys,  Lys, His, Orn, Thr, Thr        , MeThr, H—Gly—┐    , H—βAla—┐  , Boc—Gly—┐
             Thr           Thr          Thr Bzl
                         |
Boc—βAla—┐  , βAla—Thr, βAsp—Thr and Gly—Thr.
         Thr The processes for preparing the object compound (I) are explained in detail in the following.

PROCESS 1

The object compound (Ia) or a salt thereof can be prepared by reacting a compound (II) or its reactive derivative at the carboxy group or a salt thereof with a compound (III) or its reactive derivative at the amino group or a salt thereof.

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide, bis(trimethylsilyl)urea or the like; a derivative formed by react on of the compound (III) with phosphorus trichloride or phosgene, and the like.

Suitable salts of the compound (III) and its reactive derivative can be referred to the ones as exemplified for the compound (I).

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride within acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2{}^LN$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (II) to be used.

Suitable salts of the compound (II) and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt N,N'-dibenzylethylenediamine salt, etc.], or the like, and an acid addition salt as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy) -6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower-)alkylmorpholine, N,N-di(lower)alkylbenzylamine, or the like.

The reaction temperature is not critical, and the reaction is usually carried out under cooling to warming.

PROCESS 2

The object compound (Ib) or a salt thereof can be prepared by subjecting a compound (Ia) or a salt thereof to elimination reaction of the amino-protective group.

Suitable salts of the compounds (Ia) and (Ib) can be referred to the ones as exemplified for the compound (I).

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reaction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acid to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to heating.

PROCESS 3

The object compound (Id) or a salt thereof can be prepared by reacting the compound (Ic) or its reactive derivative at the amino group or a salt thereof with the compound (IV) or its reactive derivative at the carboxy group or a salt thereof.

Suitable salts of the compound (Ic) and its reactive derivative can be referred to the ones as exemplified for the compound (III).

Suitable salts of the compound (IV) and its reactive derivative can be referred to the ones as exemplified for the compound (II).

Suitable salts of the compound (Id) can be referred to the ones as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

PROCESS 4

The object compound (Ia) or a salt thereof can be prepared by subjecting the compound (Ib) or its reactive derivative at the amino group to introduction reaction of the amino protective group.

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

PROCESS 5

The object compound (If) or a salt thereof can be prepared by reacting the compound (Ie) or its reactive derivative at the amino group or a salt thereof with the compound (V) or its reactive derivative at the carboxy group or a salt thereof.

Suitable salts of the compound (Ie) and its reactive derivative can be referred to the ones as exemplified for the compound (III).

Suitable salts of the compound (V) and its reactive derivative can be referred to the ones as exemplified for the compound (II).

Suitable salts of the compound (If) can be referred to the ones as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

PROCESS 6

The object compound (Ih) or a salt thereof can be prepared by subjecting the compound (Ig) or a salt thereof to elimination reaction of the carboxy protective group.

Suitable salt of the compound (Ig) can be referred to the acid addition salt exemplified for the compound (I) and suitable salt of the compound (Ih) can be referred to the ones as exemplified for the compound (I).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4.3.0]non-5-one, 1,4-diazabicyclo[2.2.2]octane, 1,5-diazabicyclo[5.4.0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the carboxy protective group and the elimination method.

The elimination using Lewis acid is preferable to eliminate substituted or unsubstituted ar(lower)alkyl ester and carried out by reacting the compound (Ig) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof.

The reduction elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like.

The reduction method applicable for the elimination reaction may include, for example, reduction by using a combination of a metal (e.g. zinc, zinc amalgam, etc.) or a salt of chromium compound (e.g. chromous chloride, chromous acetate, etc.) and an organic or an inorganic acid (e.g. acetic acid, propionic acid, hydrochloric acid, etc.); and conventional catalytic reduction in the presence of a conventional metallic catalyst (e.g. palladium carbon, Raney nickel, etc.).

The reaction temperature is not critical, and the reaction is usually carried out under cooling, at ambient temperature or under warming.

PROCESS 7

The object compound (Ij) or a salt thereof can be prepared by subjecting the compound (Ii) or a salt thereof to elimination reaction of the amino, hydroxy or carboxy protective group.

This reaction can be carried out in substantially the same manner as Process 2, and therefore the reaction mode and reaction conditions [e.g. bases, acids, reducing agents, catalysts, solvents, reaction temperature, etc.] of this reaction are to be referred to those as explained in Process 2.

PROCESS 8

The object compound (Il) or a salt thereof can be prepared by subjecting the compound (Ik) or a salt thereof to elimination reaction of the amino protective group.

This reaction can be carried out in substantially the same manner at Process 2, and therefore the reaction mode and reaction conditions [e.g. bases, acids, reducing agents, catalysts, solvents, reaction temperature, etc.] of this reaction are to be referred to those as explained in Process 2.

The present elimination reaction includes, within its scope, the case that the amino protective group for $R^1$ and/or lower alkyl which may have suitable substituent(s) for $R^4$, $R^5$, or $R^6$ in $R^3$ is eliminated during the reaction or at the post-treating step of the present process.

PROCESS 9

The object compound (In) or a salt thereof can be prepared by subjecting the compound (Im) or a salt thereof to elimination reaction of $R_a{}^6$.

This reaction can be carried out in substantially the same manner as Process 2, and therefore the reaction mode and reaction conditions [e.g. bases, acids, reducing agents, catalysts, solvents, reaction temperature, etc.] of this reaction are to be referred to those as explained in Process 2.

The present elimination reaction includes, within its scope, the case that the amino protective group for $R^1$ and/or $R^2$ is eliminated during the reaction or at the post-treating step of the present process.

PROCESS 10

The object compound (Ip) or a salt thereof can be prepared by subjecting the compound (Io) or a salt thereof to elimination reaction of the hydroxy protective group.

This reaction can be carried out in substantially the same manner as Process 2, and therefore the reaction mode and reaction conditions [e.g. bases, acids, reducing agents, catalysts, solvents, reaction temperature, etc.] of this reaction are to be referred to those as explained in Process 2.

The present elimination reaction includes, within its scope, the case that the amino protective group for $R^1$ and/or $R^2$ is eliminated during the reaction or at the post-treating step of the present process.

PROCESS 11

The object compound (Ir) or a salt thereof can be prepared by reacting the compound (Iq) or a salt thereof with the compound (VI).

This reaction is usually conducted in a conventional solvent which does not adversely influence the reaction such as water, acetic acid, benzene, methanol, ethanol, tetrahydrofuran, dichloromethane, or a mixture thereof. The reaction temperature is not critical and the reaction is preferably conducted within the range of cooling to warming.

PROCESS 12

The object compound (It) or a salt thereof can be prepared by subjecting the compound (Is) or a salt thereof to elimination reaction of the carboxy protective group.

This reaction can be carried out in substantially the same manner as Process 2, and therefore the reaction mode and reaction conditions [e.g. bases, acids, reducing agents, catalysts, solvents, reaction temperature, etc.] of this reaction are to be referred to those as explained in Process 2.

The present elimination reaction includes, within its scope, the case that the amino protective group for $R^1$ and/or $R^2$ and/or lower alkyl which may have suitable substituent(s) for $R^4$, $R^5$ or $R^6$ in $R^3$ is eliminated during the reaction or at the post-treating step of the present process.

PROCESS 13

The object compound (Ii) or a salt thereof can be prepared by subjecting the compound (Ij) or a salt thereof to introduction reaction of the amino, hydroxy or carboxy protective group.

The reaction can be carried out in substantially the same manner as Process 1, and therefore the reaction mode and reaction conditions [e.g. solvents, reaction temperature, etc.] of this reaction are to be referred to those as explained in Process 1.

PROCESS 14

The object compound (Iv) or a salt thereof can be prepared by subjecting the compound (Iu) or a salt thereof to elimination reaction of the amino protective group.

This reaction can be carried out in substantially the same manner as Process 2, and therefore the reaction mode and reaction conditions [e.g. bases, acids, reducing agents, catalysts, solvents, reaction temperature, etc.] of this reaction are to be referred to those as explained in Process 2.

The present elimination reaction includes, within its scope, the case that the amino protective group for $R^1$ and/or $R^2$ and/or lower alkyl which may have suitable substituent(s) for $R^4$, $R^5$ or $R^6$ in $R^3$ is eliminated during the reaction or at the post-treating step of the present process.

PROCESS 15

The object compound (Ix) or a salt thereof can be prepared by subjecting the compound (Iw) or a salt thereof to elimination reaction of the amino and/or carboxy protective group.

This reaction can be carried out in substantially the same manner as Process 2, and therefore the reaction mode and reaction condition [e.g. bases, acids, reducing agents, catalysts, solvents, reaction temperature, etc.] of this reaction are to be referred to those as explained in Process 2.

The present elimination reaction includes, within its scope, the case that the amino protective group for $R^2$ and/or lower alkyl which may have suitable substituent(s) for $R^4$, $R^5$ or $R^6$ in $R^3$ is eliminated during the reaction or at the post-treating step of the present process.

PROCESS 16

The object compound (Iz) or a salt thereof can be prepared by subjecting the compound (Iy) or a salt thereof to ring closure reaction.

The reaction may be carried out in the presence of an inorganic or organic acid such as acetic acid, and the like.

The reaction temperature is not critical, and the reaction is usually carried out under cooling to warming.

PROCESS 17

The object compound (Izz) or a salt thereof can be prepared by reacting the compound (Ih) or a salt thereof with ammonia.

This reaction can be carried out in substantially the same manner as Process 11, and therefore the reaction conditions [e.g. solvents, reaction temperature, etc.] of this reaction are to be referred to those as explained in Process 11.

The compounds obtained by the above processes can be isolated and purified by a conventional method such as pulverization, recrystallization, column chromatography, reprecipitation, or the like.

It is to be noted that the compound (I) and the other compounds may include one or more stereoisomers due to asymmetric carbon atoms, and all of such isomers and mixture thereof are included within the scope of this invention.

The object compounds (I) and pharmaceutically acceptable salts thereof have pharmacological activities such as tachykinin antagonism and the like, and useful for therapeutic treatment and prevention of asthma and the like.

For therapeutic purpose, the compounds (I) and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compounds (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating asthma and the like. In general, amounts between 0.1 mg/body and about 1,000 mg/body may be administered per day.

In order to illustrate the usefulness of the object compound (I), the pharmacological test data of some representative compounds of the compound (I) are shown in the following.

Test Methods

1. ³H-Substance P receptor binding (a) Crude lung membrane preparation

Male Hartley strain guinea pigs were sacrificed by decapitation. The trachea and lung were removed and homogenized in buffer (0.25M sucrose, 50 mM Tris-HCl pH 7.5, 0.1 mM EDTA) by using Polytoron (Kinematica). The homogenate was centrifuged (1000 xg, 10 min) to remove tissue clumps and the supernatant was centrifuges (14000 xg 20 min) to yield pellets. The pellets were resuspended in buffer (5 mM Tris-HCl pH 7.5), homogenized with a teflon homogenizer and centrifuged (14000 xg, 20 min) to yield pellets which were referred to as crude membrane fractions. The obtained pellets were stored at −70° C. until use.

(b) ³H-Substance P binding to preparative membrane

Frozen crude membrane fractions were thawed and resuspended in Medium 1 (50 mM Tris-HCl pH 7.5, 5 mM MnCl₂, 0.02% BSA, 2 μg/ml chymostatin, 4 μg/ml leupeptin, 40 μg/ml bacitracin.) ³H-substance P (1 nM) was incubated with 100 μl of the membrane preparation in Medium 1 at 4° C. for 30 minutes in a final volume of 500 82 1. At the end of the incubation period, reaction mixture was quickly filtered over a Whatman GF/B glass filter (pretreated with 0.1% polyethylene imine for 3 hours prior to use) under aspiration. The filters were then washed four times with 5 ml of the buffer (50 mM Tris-HCl, pH 7.5). The radioactivity was counted in 5 ml of Aquazol-2 in Packerd scintillation counter (Packerd TRI-CARB 4530).

Test Compounds (a) Boc-Gln-D-Trp(CHO)-Phe-OBzl
(b) Ac-Gln-D-Trp(CHO)-Phe-OBzl
(c) Z-Gln-D-Trp(CHO) -Phe-OBzl
(d) Boc-Asn-D-Trp(CHO)-Phe-OBzl
(e) Boc-Ser-D-Trp(CHO)-Phe-OBzl
(f) Boc-Glu(NMe₂)-D-Trp(CHO)-Phe-OBzl
(g) Boc-Thr-D-Trp(CHO)-Phe-OBzl
(h) Boc-Gln-D-Trp(CHO)-Phe-NMeBzl
(i) Boc-Thr-D-Trp(CHO)-Phe-NMeBzl
(j) Boc-Glu(NMe₂)-D-Trp(CHO)-Phe-NMeBzl
(k) Ac-Thr-D-Trp(CHO)-Phe-NMeBzl
(l) Ac-Glu(NMe₂)-D-Trp(CHO)-Phe-NMeBzl

| Test results: | |
|---|---|
| Test Compounds (1 μg/ml) | Inhibition (%) |
| (a) | 100 |
| (b) | 100 |
| (c) | 93 |
| (d) | 99 |
| (e) | 99 |
| (f) | 100 |
| (g) | 100 |
| (h) | 100 |
| (i) | 100 |
| (j) | 100 |
| (k) | 100 |
| (l) | 100 |

In the present specification, there are employed the following abbreviations in addition to the abbreviations adopted by the IUPAC-IUB.

| | |
|---|---|
| Ac | acetyl |
| AcOH | acetic acid |
| Ac₂O | acetic anhydride |
| Boc | t-butoxycarbonyl |
| Bzl | benzyl |
| Buᵗ | t-butyl |
| Bzl(Cl) | p-chlorobenzyl |
| Bzl(o-F) | o-fluorobenzyl |
| cHex | cyclohexyl |
| Cl-Z | o-chlorobenzyloxycarbonyl |
| DCC | dicyclohexylcarbodiimide |
| DMF | N,N-dimethylformamide |
| Et | ethyl |
| 4N—HCl/DOX | 4N-hydrogen chloride in 1,4-dioxane |
| HOBT | N-hydroxybenzotriazole |
| Hyp | 4-hydroxyproline |
| Me | methyl |
| NMM | N-methyl morpholine |
| Ph | phenyl |
| Prⁱ | isopropyl |
| Py(2) | 2-pyridyl |
| Py(3) | 3-pyridyl |
| Py(4) | 4-pyridyl |
| Su | succinimido |
| Tce | 2,2,2-trichloroethyl |
| TceOH | 2,2,2-trichloroethanol |
| TFA | trifluoroacetic acid |
| THF | tetrahydrofuran |
| Tos | Tosyl (p-toluenesulfonyl) |
| Tos-Cl | tosyl chloride (p-toluenesulfonyl chloride) |
| Troc | 2,2,2-trichloroethoxycarbonyl |
| TsOH | p-toluenesulfonic acid (tosic acid) |
| WSC | 1-ethyl-3-(3′-dimethylaminopropyl)carbodiimide |
| WSC.HCl | 1-ethyl-3-(3′-dimethylaminopropyl)carbodiimide.hydrochloride |
| Z | benzyloxycarbonyl |

Further, in these examples, substituent groups on side chains in an amino acid residue can be represented by the following formulae.

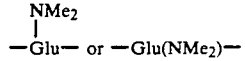

-continued

—Thr(Bzl) at Bzl position or —Thr(Bzl)—

—His— or —His(Tos)—

—Lys— or —Lys(Troc)—

—Lys— or —Lys(Cl—Z)—

—Lys— or —Lys(Z)—

—Orn— or —Orn(Z)—

—Trp— or —Trp(CHO)—

—Trp— or —Trp(Tos)—

—Trp— or —Trp(CH$_2$CO$_2$Et)—

—Trp— or —Trp(CH$_2$CO$_2$H)—

—Trp— or —Trp(CH$_2$CONH$_2$)—

—Glu— or —Glu(OTce)—

—Thr— or —Thr(CO(CH$_2$)$_2$CO$_2$H)—

—Thr— or —Thr(H—Gly)—

—Thr— or —Thr(H—βAla)—

—Thr— or —Thr(Boc—Gly)—

—Thr— or —Thr(Boc—βAla)—

More further, in these examples, the following groups can be represented by the following formulae.

—N(Me)(Bzl) or —NMeBzl

—N(Et)(Bzl) or —NEtBzl

—N(Et)(Bzl(Cl)) or —NEtBzl(Cl)

—N(Et)(Bzl(o-F)) or —NEtBzl(o-F)

—N((CH$_2$)$_2$OH)(Bzl) or —N((CH$_2$)$_2$OH)Bzl

—N((CH$_2$)$_2$OZ)(Bzl) or —N((CH$_2$)$_2$OZ)Bzl

Still more further, in these examples, it is understood that

—Asp—NH$_2$ means -β-Asp(α-NH$_2$)—, and MeThr means N-methylthreonine.

The following examples are given for purpose of illustrating the present invention in detail.

PREPARATION 1

(1)

Starting Compound: Boc—Phe—OH

Object Compound: Boc—Phe—N(Me)(Bzl)

A solution of Boc-Phe-OH (5.48 g) and NMM (2.09 g) in methylene chloride (50 ml) was cooled to −20° C. To this solution was added dropwise isobutyl chloroformate (2.82 g) maintaining the temperature between −22° C. to −20° C. in 7 minutes. After stirring the mixture for 20 minutes at the same temperature, the solution was cooled to −35° C. and HNMeBzl (2.50 g) was added dropwise to the solution. The reaction mixture was stirred for 2 hours during which period the temperature was gradually raised to −2° C. The solution was washed successively with water (twice), diluted sodium hydrogencarbonate solution (twice), water 0.5N hydrochloric acid (twice), and sodium chloride solution, and dried over magnesium sulfate. After evaporation, the solidified residue was pulverized in hot diisopropyl ether (10 ml), and after cooling, n-hexane (30 ml) was added to the mixture. The crystalline solid was filtered, washed with n-hexane (5 ml×2), and dried to give Boc-Phe-NMeBzl (6.49 g).

mp: 90°-91.5° C.

IR (Nujol): 3380, 1690, 1645 (sh), 1635, 1525 cm$^{-1}$.

NMR (CDCl$_3$, δ): 1.37 (s) and 1.43 (s)(9H), 2.67 (s) and 2.87 (s) (3H), 3.04 (2H, d, J=7Hz), 4.28 (ABq, J=14Hz) and 4.52 (s)(2H), 4.90 (1H, m), 5.4 (1H, m), 7.0-7.4 (10H).

Elemental analysis. Calculated for C$_{22}$H$_{28}$N$_2$O$_3$: C 71.71, H 7.66, N 7.60; Found: C 72.04, H 7.65, N 7.65. [α]$_D^{25}$ +19.99° (c 1.035, CHCl$_3$).

(2)

Starting Compound: Boc—Phe—N(Me)(Bzl)

Object Compound: HCl.H—Phe—N(Me)(Bzl)

To an ice-cooled solution of Boc-Phe-NMeBzl (3.0 g) and anisole (3 ml) in methylene chloride (10 ml) was added TFA (12 ml). The solution was stirred for 15 minutes at this temperature and for additional half an hour at room temperature. After evaporation, addition and re-evaporation of 4N-HCl/DOX were repeated twice (4.1 ml and 2.0 ml, respectively). The residue was dissolved in ether (15 ml), and crystallized by seeding. After standing overnight, the crystals were filtered, washed with ether, and dried to give HCl.H-Phe-NMeBzl (2.12 g).

mp: 133°–135° C.

IR (Nujol): 3400, 1650 cm$^{-1}$.

NMR (CDCl$_3$, δ): 2.43 (s) and 2.70 (s) (3H), 3.5 (2H, m), 4.13 and 4.75 (2H, ABq, J=14Hz), 5.0 (1H, m), 7.0–7.4 (10H, m), 8.85 (3H, br s).

Elemental Analysis. Calculated for C$_{17}$H$_{20}$N$_2$O.HCl.1/2H$_2$O: C 65.06, H 7.07, N 8.93; Found: C 65.53, H 6.86, N 8.90.

$[α]_D^{25}$ +57.78° (c 1.066, CHCl$_3$).

PREPARATION 2

(1)

Starting Compound: Boc-D-Trp-OH

Object Compound: Boc-D-Trp-OBzl

To an ice-cooled solution of Boc-D-Trp-OH (8.61 g) in DMF (100 ml) were added benzyl bromide (7.19 g) and diisopropylethylamine (4.02 g). The solution was stirred for two hours at the same temperature and overnight at room temperature. After evaporation, the residue was extracted with ethyl acetate. The organic layer was washed successively with water, sodium hydrogencarbonate solution, 0.5 hydrochlolic acid, and sodium chloride solution, and dried over magnesium sulfate. Evaporation gave Boc-D-Trp-OBzl (10.6 g) as a crystalline mass.

mp: 140° C.

IR (Nujol): 1730, 1690 cm$^{-1}$.

NMR (CDCl$_3$, δ): 1.45 (9H, s), 3.32 (2H, d, J=7Hz), 4.6–5.2 (2H, m), 5.12 (2H, s), 6.85 (1H, d, J=2Hz), 7.1–7.7 (4H, m), 7.30 (5H, s), 8.13 (1H, br s).

(2)

Starting Compound: Boc—D—Trp—OBzl

Object Compound: Boc—D—Trp—OBzl with Tos

Boc-D-Trp-OBzl (2.0 g) and ethyltrimethylammonium chloride (16.2 mg) were dissolved in methylene chloride (30 ml), and powdered sodium hydroxide (507 mg) was added. To this mixture was added a solution of Tos-Cl (1.45 g) in methylene chloride (5 ml) at room temperature. The reaction mixture was stirred for three and half an hour. After addition of 1N-hydrochloric acid (7.5 ml), the organic layer was separated, washed with sodium chloride solution, dried over magnesium sulfate, and evaporated to give Boc-D-Trp(Tos)-OBzl as an oil (3.23 g).

NMR (CDCl$_3$, δ): 1.43 (9H, s), 2.30 (3H, s), 3.20 (2H, d, J=6Hz), 4.5–5.2 (2H, m), 5.07 (2H, s), 7.1–8.1 (14H, m).

(3)

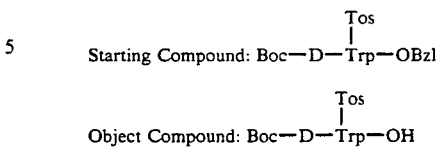

To an ice cooled solution of Boc-D-Trp(Tos)-OBzl (3.23 g) in ethanol (40 ml) was added 1N sodium hydroxide solution (6 ml) at room temperature. The solution was stirred for two hours, during this period two 2 ml portions of 1N sodium hydroxide solution were added. After evaporation of ethanol, and addition of water (50 ml), the solution was extracted once with ether. The aqueous layer was acidified with 1N hydrochloric acid and the resulting oily material was extracted with ethyl acetate, and the extract was washed with sodium chloride, and dried over magnesium sulfate. Evaporation gave Boc-D-Trp(Tos)-OH (2.5 g) as an amorphous solid.

NMR (CDCl$_3$, δ): 1.37 (9H, s), 2.32 (3H, s), 3.3 (2H, m), 4.5–4.8 (1H, m), 4.9–5.3 (1H, m), 7.2–8.3 (8H, m), 8.53 (2H, br s).

PREPARATION 3

The following object compound was obtained from the corresponding starting compound according to a similar manner to that of Preparation 1-(1).

Starting Compound: Boc—Phe—OH

Object Compound: Boc—Phe—N(Et)(Bzl)

NMR (CDCl$_3$, δ): 0.93 (3H, t, J=7Hz), 1.35 (9H, s), 2.8–3.2 (4H, m), 4.1–5.0 (3H, m), 5.1–5.4 (1H, m), 6.8–7.4 (10H, m).

PREPARATION 4

Starting Compound: Boc-Phe-OH

Object Compound: Boc-Phe-OCH$_2$Py(2)

A mixture of Boc-Phe-OH (1.59 g), 2-pyridinemethanol (0.65 g), DCC (1.24 g) in methylene chloride (30 ml) was stirred for one day at room temperature. The insoluble materials were filtered off, and the filtrate was evaporated. The residue was extracted with ethyl acetate and the organic layer was washed successively with 2% sodium hydrogencarbonate, water and saturated sodium chloride solution, and dried over magnesium sulfate. The evaporated residue was subjected to column chromatography on silica gel (50 g) and eluted with chloroform. The fractions containing the object compound were combined and evaporated to give Boc-Phe-OCH$_2$Py(2) (1.23 g).

IR (Neat): 3380, 2990, 1740–1710 (broad) cm$^{-1}$.

NMR (DMSO-d$_6$, δ): 1.32 (9H, s), 2.7–3.2 (2H, m), 4.2–4.5 (1H, m:, 5.19 (2H, s), 7.2–7.5 (8H, m), 7.7–8.0 (1H, m), 8.5–8.7 (1H, m).

PREPARATION 5

Starting Compound: Boc—D—Trp—OBzl

-continued

Object Compound: Boc—D—Trp—OBzl
              |
              CH$_2$CO$_2$Et

To a solution of Boc-D-Trp-OBzl (3.0 g) in methylene chloride (60 ml) were added powdered sodium hydroxide (1.52 g), ethyltrimethylammonium chloride (150 mg) and ethyl bromoacetate (2.54 g). The mixture was stirred overnight at room temperature, then powdered sodium hydroxide (0.61 g) and ethyl bromoacetate (0.63 g) were added. The mixture was stirred further for four and half an hour at room temperature and for two hours under reflux. After cooling, 1N-hydrochloric acid (53 ml) was added to the mixture, and the organic layer was washed with sodium chloride solution and dried with magnesium sulfate. After evaporation, the residue (4.87 g) was chromatographed on a silica gel column (60 g) eluting successively with chloroform and chloroform-ethyl acetate (4:1) to give a purified Boc-D-Trp(CH$_2$CO$_2$Et)-OBzl (4.14 g).

NMR (CDCl$_3$, δ): 1.20 (3H, t, J=7Hz), 1.43 (9H, s), 3.31 (2H, d, J=6Hz), 4.22 (2H, q, J=7Hz), 4.70 (2H, s), 5.11 (2H, s), 4.7 (1H, m), 5.1 (1H, m), 6.7 (1H, s), 7.1–7.4 (3H, m), 7.3 (5H, s), 7.5–7.7 (1H, m).

PREPARATION 6

Starting Compound: Boc—D—Trp—OBzl
                   |
                   CH$_2$CO$_2$Et Object Compound: Boc—D—Trp—OH
                 |
                 CH$_2$CO$_2$Et To a solution of Boc-D-Trp(CH$_2$CO$_2$Et)-OBzl (4.14 g) in ethanol (60 ml) was added 5% palladium on carbon (0.7 g) and the mixture was hydrogenated for one and half an hour under atmospheric pressure. Filtration of the catalyst and concentration of the filtrate under vacuum gave Boc-D-Trp(CH$_2$CO$_2$Et)-OH as an amorphous solid (3.06 g).

NMR (CDCl$_3$, δ): 1.23 (3H, t, J=7Hz), 1.40 (9H, s), 3.32 (2H, d, J=6Hz), 4.23 (2H, q, J=7Hz), 4.77 (2H, s), 4.6–4.8 (1H, m), 5.2 (1H, m), 7.00 (1H, s), 7.1–7.4 (2H, m), 7.6–7.9 (2H, m).

PREPARATION 7

Starting Compound: H-Phe-OH

Object Compound: TsOH.H-Phe-OBzl(Cl)

A mixture of H-Phe-OH (1.65 g), 4-chlorobenzyl alcohol (7.12 g) and p-toluenesulfonic acid monohydrate (2.09 g) in carbon tetrachloride (30 ml) was refluxed for 22 hours while water was removed by molecular sieves 3A/8. After adding diethyl ether, the white crystal was filtered, washed with diethyl ether and dried to give TsOH.H-Phe-OBzl(Cl) (4.59 g).

IR (Nujol): 3250, 1750, 1600, 1520 cm$^{-1}$.

NMR (DMSO-d$_6$, δ): 2.29 (3H, s), 2.9–3.4 (2H, m), 4.37 (1H, t, J=7Hz), 5.13 (2H, s), 7.1–7.7 (13H, m), 8.51 (3H, br s).

PREPARATION 8

The following object compound was obtained from the corresponding starting compound according to a similar manner to that of Preparation 7.

Starting Compound: H-Phe-OH

Object Compound: TsOH.H-Phe-OCH$_2$cHex

IR (Nujol): 1735, 1515, 1240, 1210, 1180 cm$^{-1}$.

NMR (DMSO-d$_6$, δ): 0.5–1.7 (11H, m), 2.30 (3H, s), 2.8–3.5 (2H, m), 3.86 (2H, d, J=6Hz), 4.33 (1H, dd, J=6 and 3Hz), 7.15 (2H, d, J=8Hz), 7.2–7.5 (5H, m), 7.55 (2H, d, J=8Hz), 8.48 (3H, br s).

PREPARATION 9

The following object compound was obtained from the corresponding starting compound according to a similar manner to that of Preparation 4.

Starting Compound: Boc-Phe-OH

Object Compound: Boc-Phe-OCH$_2$Py(4)

IR (Nujol): 3210, 1750, 1705, 1530 cm$^{-1}$.

NMR (DMSO-d$_6$, δ): 1.33 (9H, s), 2.8–3.2 (2H, m), 4.1–4.5 (1H, m), 5.16 (2H, s), 7.1–7.5 (3H, m), 7.28 (5H, s), 8.5–8.6 (2H, m).

PREPARATION 10

The following object compounds were obtained from the corresponding starting compounds according to a similar manner to that of Preparation 1-(2).

(1)

Starting Compound: Boc-Phe-OCH$_2$Py(4)

Object Compound: 2HCl.H-Phe-OCH$_2$Py(4)

NMR (DMSO-d$_6$, δ): 3.0–3.6 (2H, m), 4.3–4.6 (1H, m), 5.46 (2H, s), 7.33 (5H, s), 7.92 (2H, d, J=6Hz), 8.92 (2H, d, J=6Hz), 9.2 (4H, br s).

(2)

Starting Compound: Boc-Phe-NHBzl

Object Compound: HCl.H-Phe-NHBzl

IR (Nujol): 3430, 1670, 1545 cm$^{-1}$.

NMR (DMSO-d$_6$, δ): 3.13 (2H, d, J=6Hz), 4.0–4.5 (3H, m), 7.0–7.4 (5H, m), 7.28 (5H, s), 8.58 (3H, br s), 9.19 (1H, br t, J=6Hz).

(3)

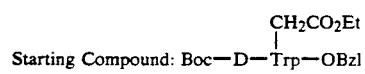

NMR (DMSO-d$_6$, δ): 2.91 (2H, d, J=6Hz), 3.10 (3H, s), 3.79 (1H, t, J=6Hz), 6.6–7.0 (4H, m), 7.1–7.4 (6H, m), 8.67 (3H, s).

(4)

Starting Compound: Boc-Phe-NHPh

Object Compound: HCl.H-Phe-NHPh

NMR (DMSO-d$_6$, δ): 3.88 (2H, d, J=6Hz), 4.36 (1H, t, J=6Hz), 7.0–7.5 (8H, m), 7.5–7.7 (2H, m), 8.52 (3H, br s), 11.00 (1H, s).

(5)

Starting Compound: Boc-Phe-(CH₂)₂Ph

Object Compound: HCl.H-Phe-(CH₂)₂Ph

IR (Nujol): 3200, 1720, 1610 cm⁻¹.
NMR (DMSO-d₆, δ): 2.6–2.9 (4H, m), 3.0–3.3 (2H, m), 4.37 (1H, t, J=7Hz), 7.0–7.4 (5H, m), 7.30 (5H, s), 8.61 (3H, br s).

PREPARATION 11

Starting Compound: Boc-Phe-OH

Object Compound: Boc-Phe-OCH₂Py(3)

To a solution of Boc-Phe-OH (2.65 g) and 3-pyridinemethanol (1.31 g) in DMF (30 ml) were added WSC.HCl (1.92 g) and 4-dimethylaminopyridine (0.12 g) under ice-cooling. The mixture was stirred for 3.5 hours. After evaporation and extraction with ethyl acetate, the organic layer was washed successively with water, 2% sodium hydrogencarbonate, water and saturated sodium chloride solution, dried over magnesium sulfate and evaporated. The residue was subjected to column chromatography on silica gel (50 g), and eluted with chloroform and then a mixture of chloroform and methanol (50:1). The fractions containing the object compound were combined and evaporated to give Boc-Phe-OCH₂Py(3) (3.56 g).

NMR (DMSO-d₆, δ): 1.31 (9H, s), 2.7–3.1 (2H, m), 3.9–4.4 (1H, m), 5.15 (2H, s), 7.1–7.5 (2H, m), 7.28 (5H, s), 7.6–7.8 (1H, m), 8.5–8.7 (2H, m).

PREPARATION 12

Starting Compound: Boc—Phe—OH

Object Compound: Boc—Phe—N(Me)(Ph)

To a solution of Boc-Phe-OH (2.65 g), N-methylaniline (1.09 g) and HOBT (1.35 g) in DMF (25 ml) was added WSC.HCl (1.92 g) under ice-cooling. The mixture was stirred for 5 hours at room temperature. After evaporation and extraction with ethyl acetate, the organic layer was washed successively with 2% hydrochloric acid, water, 2% sodium hydrogencarbonate, water and saturated sodium chloride solution, and dried over magnesium sulfate. The evaporated residue was subjected to column chromatography on silica gel (100 g) and eluted with a mixture of chloroform and methanol (100:1). The fractions containing the object compound were combined and evaporated to give Boc-Phe-NMePh (2.17 g).

IR (Neat): 3310, 2290, 1710, 1655, 1600, 1500 cm⁻¹.
NMR (DMSO-d₆, δ): 1.31 (9H, s), 2.5–3.0 (2H, m), 3.17 (3H, s), 4.0–4.4 (1H, m), 6.6–7.6 (11H, m).

PREPARATION 13

The following object compounds were obtained from the corresponding starting compounds according to a similar manner to that of Preparation 12.

(1)

Starting Compound: Boc-Phe-OH

Object Compound: Boc-Phe-NHBzl

IR (Nujol): 3310, 1680, 1660, 1525 cm⁻¹.
NMR (DMSO-d₆, δ): 1.31 (9H, s), 2.6–3.2 (2H, m), 4.0–4.4 (1H, m), 4.30 (2H, d, J=6Hz), 6.92 (1H, br d, J=8Hz), 7.28 (10H, s), 8.40 (1H, t, J=6Hz).

(2)

Starting Compound: Boc-Phe-OH

Object Compound: Boc-Phe-NHPh

NMR (DMSO-d₆, δ): 1.32 (9H, s), 2.6–3.2 (2H, m), 4.0–4.5 (1H, m), 6.9–7.5 (9H, m), 7.5–7.7 (2H, m), 10.09 (1H, s).

PREPARATION 14

The following object compounds were obtained from the corresponding starting compounds according to a similar manner to that of Preparation 1-(1).

(1)

Starting Compound: Boc—Phe—OH

Object Compound: Boc—Phe—N(Et)(Bzl(o-F))

IR (Neat): 1710, 1640, 1490 cm⁻¹.
NMR (DMSO-d₆, δ): 0.89 (t, J=6.5Hz) and 0.97 (t, J=6.5Hz)(3H), 1.25 (s) and 1.33 (s)(9H), 2.7–3.1 (2H, m), 3.28 (q, J=6.5Hz), and 3.43 (q, J=6.5Hz)(2H), 4.3–4.8 (3H, m), 6.9–7.4 (5H, m), 7.20 (5H, s).

(2)

Starting Compound: Boc—Phe—OH

Object Compound: Boc—Phe—N((CH₂)₂OH)(Bzl)

IR (Nujol): 3460, 3390, 1690, 1625, 1520 cm⁻¹.
NMR (DMSO-d₆, δ): 1.25 (s) and 1.32 (s)(9H), 2.6–3.8 (6H, m), 4.2–4.9 (4H, m), 6.9–7.4 (11H, m).

PREPARATION 15

Starting Compound: Boc—Phe—N((CH₂)₂OH)(Bzl)

Object Compound: Boc—Phe—N((CH₂)₂OZ)(Bzl)

To a solution of Boc-Phe-N((CH₂)₂OH)Bzl (3.75 g), pyridine (7.6 ml) and 4-dimethylaminopyridine (0.23 g) in THF (100 ml) was added dropwise a solution of benzyl chloroformate (2.7 ml) in THF (3 ml) under ice-cooling. After stirring for 2 hours, a solution of benzyl chloroformate (2.7 ml) in THF (3 ml) was added to the mixture. The mixture was stirred for further 3 hours and then evaporated. The residue was crystallized with petroleum ether, filtered, washed with petroleum ether and dried to give Boc-Phe-N((CH₂)₂OZ)Bzl (4.58 g).

mp: 85°–86° C.
IR (Nujol): 3390, 1740, 1690, 1650, 1520 cm⁻¹.

NMR (DMSO-d$_6$, δ): 1.25 (s) and 1.32 (s)(9H), 2.6-3.0 (2H, m), 3.2-3.8 (2H, m), 3.8-4.9 (5H, m), 5.10 (2H, s), 6.9-7.5 (16H, m).

PREPARATION 16

Starting Compound: Boc-Phe-OPy(2)

Object Compound: Boc-Phe-(CH$_2$)$_2$Ph

In a nitrogen atmosphere, a solution of phenethyl bromide (2.05 ml) in THF (10 ml) was added to a stirred mixture of magnesium (0.44 g) in THF (5 ml) at 30°-40° C. After filtration, the solution was added over fifteen minutes to a stirred solution of Boc-Phe-OPy(2) (1.71 g) in THF (100 ml) at −70° C. The mixture was stirred for half an hour at −70° C., then saturated ammonium chloride solution (15 ml) was added. After filtration, evaporation and extraction with ethyl acetate, the organic layer was washed with 0.1N sodium hydroxide solution and saturated sodium chloride solution, dried over magnesium sulfate and evaporated. The residual solid was filtered, washed with n-hexane. The solid was subjected to column chromatography on silica gel (200 g) and eluted with a mixture of chloroform and n-hexane (1:1). The fractions containing the object compound were combined and evaporated. The residual white crystals were filtered washed with n-hexane and dried to give Boc-Phe-(CH$_2$)$_2$Ph (1.30 g).

IR (Nujol): 3460, 1715, 1690, 1515 cm$^{-1}$.

NMR (DMSO-d$_6$, δ): 1.31 (9H, s), 2.6-3.2 (2H, m), 2.76 (4H, s), 4.0-4.4 (1H, m), 7.22 (11H, s).

PREPARATION 17

Starting Compound: Boc—Glu—OBzl

Object compound: Boc—Glu—OBzl
with OTce above

To a solution of Boc-Glu-OBzl (1.00 g) and TceOH (0.53 g) in methylene chloride (15 ml) were added 4-dimethylaminopyridine (0.04 g) and WSC.HCl (0.57 g) successively under ice cooling. The mixture was stirred for 3 hours at the same temperature. After evaporation, the residue was extracted with ethyl acetate. The organic layer was washed successively with 2% hydrochloric acid, water, 2% sodium hydrogencarbonate solution, water and saturated sodium chloride solution, and dried over magnesium sulfate. The evaporated residue was crystallized with petroleum ether, filtered and dried to give Boc-Glu(OTce)-OBzl (1.01 g).

IR (Nujol): 3400, 1740, 1700, 1510 cm$^{-1}$.

NMR (DMSO-d$_6$, δ): 1.36 (9H, s), 1.7-2.2 (2H, m), 2.4-2.7 (2H, m), 3.9-4.3 (1H, m), 4.88 (2H, s), 5.14 (2H, s), 7.3 (1H, br s), 7.38 (5H, s).

PREPARATION 18

Starting compound: Boc—Glu—OBzl (with OTce)

Object Compound: Boc—Glu—OH (with OTce)

Boc-Glu(OTce)-OBzl (0.50 g) was hydrogenated in ethanol (25 ml) with 10% palladium on carbon (0.10 g). The catalyst was filtered off and the filtrate was evaporated. The residue was extracted with ethyl acetate. The organic layer was washed successively with 2% hydrochloric acid, water and saturated sodium chloride, dried over magnesium sulfate and evaporated. The residue was pulverized with petroleum ether, filtered and dried to give Boc-Glu(OTce)-OH (0.30 g).

IR (Nujol): 3400, 1740, 1730, 1660, 1520 cm$^{-1}$.

NMR (DMSO-d$_6$, δ): 1.38 (9H, s), 1.7-2.2 (2H, m), 2.3-2.6 (2H, m), 3.8-4.2 (1H, m), 4.88 (2H, s), 7.12 (1H, br d, J=8Hz), 12.5 (1H, broad).

PREPARATION 19

Starting Compound: Boc—Gly—OMe

Object Compound: 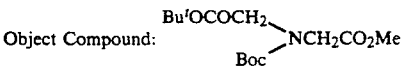

To an ice-cooled solution of Boc-Gly-OMe (1.89 g) and tert-butyl bromoacetate (3.90 g) in THF (30 ml) was added sodium hydride (60% in oil) (0.8 g) under nitrogen atmosphere. The solution was stirred for an hour under ice-cooling and further for two hours at room temperature. Acetic acid (1.5 ml) was added to the solution under cooling and the product was extracted with ethyl acetate. The organic layer was washed successively with 0.5N hydrochloric acid, diluted sodium hydrogencarbonate solution, and sodium chloride solution, and dried over magnesium sulfate to give

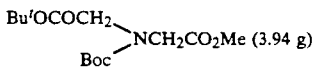 (3.94 g)

as an oil.

IR (film): 1750, 1710 cm$^{-1}$.

NMR (CDCl$_3$, δ) 1.15 (9H×2, s), 3.77 (3H, s), 3.97 (2H, dd, J=15Hz), 4.08 (2H, dd, J=15Hz).

PREPARATION 20

Starting Compound: 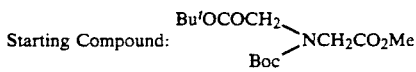

Object Compound: 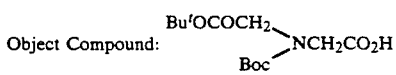

To an ice-cooled solution of

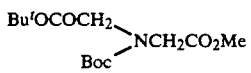

(3.9 g) in methanol (40 ml) was added dropwise 1N-sodium hydroxide solution (10 ml). After stirring for two hours 1N-sodium hydroxide solution (7 ml) was added. After evaporation of methanol, water (20 ml) was added and extracted with ether once. The aqueous layer was acidified to pH 2, and extracted with ethyl acetate and the organic layer was washed with sodium chloride solution and dried over magnesium sulfate to give

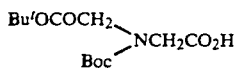

(3.02 g) as an oil.

IR (Film): 2600, 1740–1700 (br) cm$^{-1}$.

NMR (CDCl$_3$, δ): 1.43 (9H, s), 1.50 (9H, s), 3.95–4.3 (4H, m), 9.43 (1H, s).

PREPARATION 21

Starting Compound: 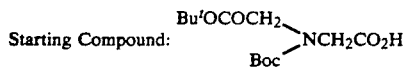

Object Compound: 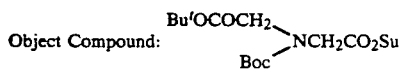

To an ice-cooled solution of

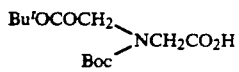

(3.95 g) and pyridine (1.08 g) in acetonitrile (50 ml) was added di-succinimidyl carbonate (3.49 g). The solution was stirred overnight at room temperature. After concentration, the product was extracted with ethyl acetate and the extract was washed successively with water, diluted sodium hydrogencarbonate solution, 0.5N hydrochloric acid, and sodium chloride solution, and dried over magnesium sulfate. The residue (3.84 g) was crystallized with diisopropyl ether-n-hexane (1:1) to give

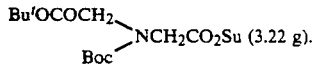

mp: 102°–108° C.

IR (Nujol): 1840, 1780, 1745 (sh), 1730 cm$^{-1}$.

NMR (CDCl$_3$, δ): 1.50 (18H, s), 2.87 (4H, s), 4.02 and 4.38 (4H, two set of ABq, J=10Hz).

PREPARATION 22

The following object compound was obtained from the corresponding starting compound according to a similar manner to that of Preparation 1-(1).

Starting Compound: Boc—Phe—OH

Object Compound: 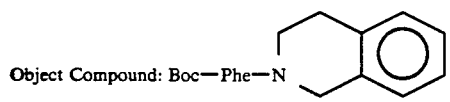

NMR (DMSO-d$_6$, δ): 1.29 (s) and 1.30 (s)(9H), 2.5–3.0 (4H, m), 3.4–3.8 (2H, m), 4.4–4.8 (3H, m), 6.7–6.9 (1H, m), 7.0–7.3 (9H, m).

EXAMPLE 1

Starting Compound: Boc—D—Trp—OH
$\quad\quad\quad\quad\quad\quad\quad\quad\quad$ CHO -continued Object Compound: Boc—D—Trp—Phe—OBzl
$\quad\quad\quad\quad\quad\quad\quad\quad\quad\quad\quad$ CHO Boc-D-Trp(CHO)-OH (2.99 g), TsOH.H-Phe-OBzl (3.85 g, and HOBT (1.22 g) were dissolved in a mixed solvent of methylene chloride (60 ml) and DMF (15 ml). To this solution was added WSC (1.53 g) under ice cooling, and the reaction mixture was stirred for 3 hours at the same temperature. The reaction mixture was concentrated and extracted with ethyl acetate. The organic layer was washed successively with diluted sodium hydrogencarbonate solution (twice), water, 0.5N hydrochloric acid, and saturated sodium chloride solution, and dried over magnesium sulfate. After concentration, the residue was crystallized from a mixture of ethyl acetate and diisopropyl ether (1:1), which was filtered, washed with diisopropyl ether, and dried to give Boc-D-Trp(CHO)-Phe-OBzl (4.95 g).

mp: 146°–147° C.

IR (Nujol): 3340, 1732 (sh), 1710, 1686, 1650, 1545, 1528 cm$^{-1}$.

NMR (DMSO-d$_6$, δ): 1.30 (9H, s), 2.65–2.85 (2H, m), 2.90 and 3.15 (2H, d of ABq, J=14Hz and 6Hz, 14Hz and 9Hz), 4.2–4.5 (1H, m), 4.5–4.85 (1H, m), 5.15 (2H, s), 6.83 (1H, d, J=8Hz), 7.25 (5H, s), 7.40 (5H, s), 7.2–7.85 (4H, m), 8.20 (1H, br s), 8.62 (1H, d, J=8Hz), 9.3–9.8 (1H, br s).

Elemental Analysis. Calculated for C$_{33}$H$_{35}$N$_3$O$_6$: C 69.58, H 6.19, N 7.38; Found: C 69.69, H 6.09, N 7.36.

EXAMPLE 2

Starting Compound: Boc—D—Trp—Phe—OBzl
$\quad\quad\quad\quad\quad\quad\quad\quad\quad\quad$ CHO Object Compound: HCl.H—D—Trp—Phe—OBzl
$\quad\quad\quad\quad\quad\quad\quad\quad\quad\quad$ CHO TFA (45 ml) was added to a mixture of Boc-D-Trp(CHO)-Phe-OBzl (4.86 g) and anisole (6.0 ml) under ice cooling and the mixture was stirred for 15 minutes at the same temperature and for additional 20 minutes after removing the ice bath. The reaction mixture was concentrated and 4N-HCl/DOX (4.27 ml) was added, and concentrated again. Addition of diisopropyl ether gave precipitates, which were collected by filtration, washed with the same solvent, and dried to give HCl.H-D-Trp(CHO)-Phe-OBzl (4.70 g).

NMR (DMSO-d$_6$, δ): 2.7–3.3 (4H, m), 3.9–4.3 (1H, m), 4.4–4.9 (1H, m), 5.13 (2H, s), 7.23 (5H, s), 7.36 (5H, s), 7.2–7.5 (2H, m), 7.55–7.85 (2H, m), 8.2 (1H, br s), 8.35 (3H, br s), 9.4 (1H, br s), 9.45 (1H, br d, J=8Hz).

EXAMPLE 3

Starting Compound: Boc—D—Trp—OH
$\quad\quad\quad\quad\quad\quad\quad\quad\quad$ CHO Object Compound: 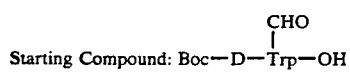

Boc-D-Trp(CHO)-OH (3.26 g), HCl.H-Phe-NMeBzl (2.99 g) and HOBT (1.32 g) were dissolved in DMF (40 ml). To this solution was added WSC under ice cooling. The reaction mixture was stirred for an hour at this temperature and for additional an hour at room temperature. After evaporation and extraction with ethyl acetate, the organic layer was washed successively with diluted sodium hydrogencarbonate solution, water, 0.5N hydrochloric acid, and sodium chloride solution and dried over magnesium sulfate. The evaporated residue was crystallized from a mixed solvent of ethyl acetate and diisopropyl ether (3:4) (35 ml) with seeding. The crystals were collected by filtration after addition of diisopropyl ether (55 ml) and dried to give Boc-D-Trp(CHO)-Phe-NMeBzl (4.96 g).

mp: 88°–90° C.

IR (Nujol): 3300–3200, 1710, 1620, 1530 cm$^{-1}$.

NMR (CDCl$_3$, δ): 1.41 (9H, s), 2.70 and 2.85 (3H, s), 2.90 (2H, d, J=7Hz), 3.18 (2H, d, J=7Hz), 4.2–4.73 (3H, m), 4.98–5.28 (2H, m), 6.9–7.4 (14H, m), 7.5–7.7 (1H, m), 8.3 (1H, br s), 8.8–9.5 (1H, br s).

Elemental Analysis. Calculated for $C_{34}H_{38}N_4O_5$ C 70.08, H 6.57, N 9.62; Found: C 70.39, H 6.86, N 9.49. $[α]_D^{25}$ +16.75° (c 0.794 CHCl$_3$).

EXAMPLE 4

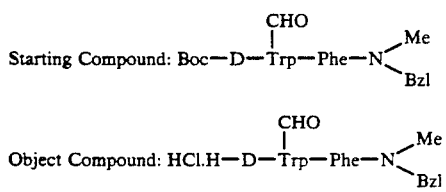

Starting Compound: Boc—D—Trp(CHO)—Phe—N(Me)(Bzl)

Object Compound: HCl.H—D—Trp(CHO)—Phe—N(Me)(Bzl)

A mixture of Boc-D-Trp(CHO)-Phe-NMeBzl (1.53 g) and anisole (1.6 ml) was treated with TFA (10 ml) for 15 minutes under ice-cooling and for additional half an hour at room temperature. After evaporation of TFA, 4N-HCl/DOX (1.3 ml) was added to the residue and the mixture was concentrated again. The residue was triturated with ether, filtered, washed with diisopropyl ether, and dried to give HCl.H-D-Trp(CHO)-Phe-NMeBzl (13.4 g).

NMR (DMSO-d$_6$, δ): 2.5–3.1 (4H, m), 2.81 (s) and 2.89 (s)(3H), 3.8–5.2 (4H, m), 6.9–7.5 (12H, m), 7.5–7.9 (2H, m), 8.2 (1H, br s), 8.4 (3H, br s), 9.1–9.6 (2H, m).

EXAMPLE 5

The following object compound was obtained from the corresponding starting compound according to a similar manner to that of Example 1.

Starting Compound: Boc-D-Trp-Phe-OH

Object Compound: Boc-D-Trp-Phe-OBzl mp: 145°–146° C.

IR (Nujol): 3400 (sh), 3360, 1730, 1690, 1660, 1520 cm$^{-1}$.

NMR (DMSO-d$_6$, δ): 1.30 (9H, s), 2.5–3.3 (4H, m), 4.00–4.35 (1H, m), 4.35–4.75 (1H, m), 5.08 (2H, s), 6.55 (1H, d, J=8.5Hz), 6.80–7.65 (16H, m), 8.36 (1H, d, J=8.5Hz).

Elemental Analysis. Calculated for $C_{32}H_{35}N_3O_5$: C 70.96, H 6.51, N 7.76; Found: C 71.12, H 6.76, N 7.88.

EXAMPLE 6

The following object compound was obtained from the corresponding starting compound according to a similar manner to that of Example 2.

Starting Compound: Boc-D-Trp-Phe-OBzl

Object Compound: HCl.H-D-Trp-Phe-OBzl

IR(Nujol): 3400 (broad), 3200, 1735, 1690 (sh), 1680 cm$^{-1}$.

NMR (DMSO-d$_6$, δ): 2.55–3.25 (4H, m), 3.75–4.15 (1H, m), 4.30–4.60 (1H, m), 5.03 (2H, s), 6.6–7.70 (15H, m), 8.07 (3H, br s), 9.13 (1H, d, J=9Hz), 10.93 (1H, s).

EXAMPLE 7

The following object compound was obtained from the corresponding starting compound according to a similar manner to that of Example 3.

Starting Compound: Boc—D—Trp(Tos)—OH

Object Compound: Boc—D—Trp(Tos)—Phe—N(Me)(Bzl)

IR (Nujol): 3300, 3250, 1710, 1620 cm$^{-1}$.

mp: 98°–100° C.

NMR (CDCl$_3$, δ): 1.35 (9H, s), 2.28 (3H, s), 2.58 and 2.79 (3H, s), 2.74 (2H, d, J=6Hz), 3.11 (2H, d, J=6Hz), 4.22 and 4.60 (2H, ABq, J=14Hz), 4.2–4.5 (1H, m), 4.85–5.2 (2H, m), 6.75–8.0 (20H, m).

Elemental Analysis. Calculated for $C_{40}H_{44}N_4O_6S_1$: C 67.78, H 6.26, N 7.90; Found: C 67.24, H 6.33, N 7.62.

EXAMPLE 8

Starting Compound: Boc—Phe—N(Et)(Bzl)

Object Compound: Boc—D—Trp(CHO)—Phe—N(Et)(Bzl)

To an ice-cooled solution of Boc-Phe-NEtBzl (3.95 g) and anisole (4 ml) in methylene chloride (16 ml) was added TFA (16 ml). The solution was stirred for an hour at room temperature. After evaporation, addition and re-evaporation of 4N-HCl/DOX (5 ml) were repeated twice. The residue was dissolved in DMF (40 ml), and the solution was ice-cooled and neutralized with triethylamine (1.39 ml). To the solution containing H-Phe-NEtBzl obtained was added Boc-D-Trp(CHO)-OH (3.32 g), HOBT (1.35 g) and WSC.HCl (1.92 g). The solution was stirred for one and half an hour at room temperature. After evaporation and extraction with ethyl acetate. The organic layer was washed successively with water, 2% hydrochloric acid, water, 2% sodium hydrogencarbonate, water and saturated sodium chloride and dried over magnesium sulfate. The evaporated residue was subjected to column chromatography on silica gel (200 g) and eluted with a mixture of chloroform and methanol (50:1 to 20:1, gradient elution). The fractions containing the object compound were combined and evaporated. The residue were pulverized with n-hexane, collected by filtration, washed with n-hexane and dried to give Boc-D-Trp(CHO)-Phe-NEtBzl (4.47 g).

IR (Nujol): 3300, 1710, 1630 cm$^{-1}$.

NMR (DMSO-d$_6$, δ): 0.97 (t, J=7Hz) and 1.07 (t, J=7Hz)(3H), 1.25 (9H, s), 2.5–3.4 (6H, m), 4.1–5.2 (4H, m), 6.6–6.9 (1H, m), 6.9–7.9 (14H, m), 7.9–8.3 (1H, m), 8.56 (1H, br d, J=9Hz), 9.3 (1H, broad).

Elemental Analysis. Calculated for $C_{35}H_{40}N_4O_5$: C 70.45, H 6.76, N 9.39; Found: C 70.49, H 7.01, N 9.18.

EXAMPLE 9

The following object compound was obtained from the corresponding starting compound according to a similar manner to that of Example 8.

Starting Compound: Boc—Phe—OCH₂Py(2)

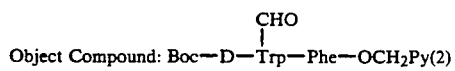

Object Compound: Boc—D—Trp—Phe—OCH₂Py(2) (with CHO on Trp)

mp: 153°–154° C.

IR (Nujol): 3330, 1740, 1720, 1685, 1650, 1555, 1525 cm⁻¹.

NMR (DMSO-d₆, δ): 1.29 (9H, s), 2.55–2.85 (2H, m), 2.85–3.2 (2H, m), 4.1–4.5 (1H, m), 4.5–4.8 (1H, m), 5.22 (2H, s), 6.88 (1H, br d, J=9Hz), 7.2–7.6 (10H, m), 7.6–7.9 (2H, m), 7.9–8.3 (1H, m), 8.5–8.7 (2H, m), 9.4 (1H, broad).

Elemental Analysis. Calculated for $C_{32}H_{34}N_4O_6$: C 67.35, H 6.01, N 9.82; Found: C 67.38, H 5.78, N 9.82.

EXAMPLE 10

The following object compound was obtained from the corresponding starting compound according to a similar manner to that of Example 2.

Starting Compound: Boc—D—Trp(CHO)—Phe—OCH₂Py(2)

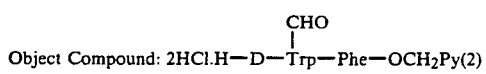

Object Compound: 2HCl.H—D—Trp(CHO)—Phe—OCH₂Py(2)

NMR (DMSO-d₆, δ): 2.7–3.3 (4H, m), 3.9–4.5 (1H, m), 4.5–5.0 (1H, m), 5.44 (2H, s), 7.1–7.5 (7H, m), 7.5–7.9 (6H, m), 8.0–8.6 (4H, m), 8.6–8.9 (1H, m), 9.4 (1H, broad), 9.74 (1H, d, J=8Hz).

EXAMPLE 11

Starting Compound: HCl.H—D—Trp(CHO)—Phe—OBzl

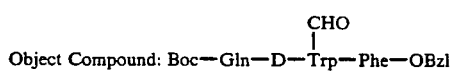

Object Compound: Boc—Gln—D—Trp(CHO)—Phe—OBzl

To a solution of Boc-Gln-OH (2.10 g), HCl.H-D-Trp(CHO)-Phe-OBzl (4.70 g) and HOBT (1.15 g) in a mixed solvent of methylene chloride (60 ml) and DMF (10 ml), was added WSC (1.41 g) under ice cooling. The reaction mixture was stirred for 1.5 hours at the same temperature and for additional 1.5 hours at room temperature and concentrated under reduced pressure. Water was added to the residue and the resulting precipitates were collected and washed successively with water, diluted sodium hydrogencarbonate solution and water. After drying, the crude product (5.84 g) was stirred in hot ethyl acetate (60 ml) in water bath. After cooling, the precipitates were collected by filtration and dried to give Boc-Gln-D-Trp(CHO)-Phe-OBzl (5.70 g).

mp: 202°–203.5° C.

IR (Nujol): 3440, 3300, 1720, 1660 (sh), 1645 cm⁻¹.

NMR (DMSO-d₆, δ): 1.33 (9H, s), 1.5–1.8 (2H, m), 1.85–1.95 (2H, m), 2.7–3.1 (4H, m), 3.90 (1H, br s), 4.45–4.8 (2H, m), 5.10 (2H, s), 6.70 (2H, br s), 7.20 (5H, s), 7.35 (5H, s), 7.1–7.7 (4H, m), 7.55 (1H, m), 7.95–8.25 (2H, m), 8.65 (1H, d, J=6Hz), 9.3 (1H, br s).

Elemental Analysis. Calculated for $C_{38}H_{43}N_5O_8$: C 65.41, H 6.21, N 10.04; Found: C 65.14, H 6.09, N 9.96. $[\alpha]_D^{25}+2.88°$ (c 1.110, DMF).

EXAMPLE 12

The following object compounds were obtained from the corresponding starting compounds according to a similar manner to that of Example 11.

Starting Compound: HCl.H—D—Trp(CHO)—Phe—OBzl

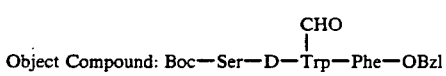

Object Compound: Boc—Ser—D—Trp(CHO)—Phe—OBzl mp: 164°–166° C.

IR (Nujol): 3200, 1700 (broad), 1640, 1550, 1525 cm⁻¹.

NMR (DMSO-d₆, δ): 1.33 (9H, s), 2.7–3.2 (4H, m), 3.35–3.65 (2H, m), 3.8–4.2 (1H, m), 4.4–4.9 (3H, m), 5.12 (2H, s), 6.60 (1H, br s), 7.2–7.7 (4H, m), 7.23 (5H, s), 7.36 (5H, s), 7.9–8.3 (2H, m), 8.67 (1H, br d, J=8Hz), 9.3 (1H, br s).

Elemental Analysis. Calculated for $C_{36}H_{40}N_4O_8 \cdot H_2O$: C 64.08, H 6.27, N 8.30; Found: C 64.42, H 6.28, N 8.68.

(2)

Starting Compound: HCl.H—D—Trp(CHO)—Phe—OBzl

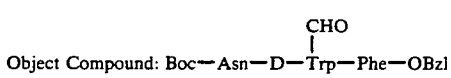

Object Compound: Boc—Asn—D—Trp(CHO)—Phe—OBzl mp: 208°–210° C.

IR (Nujol): 3330, 1710, 1690, 1660, 1640, 1555 (sh), 1540 cm⁻¹.

NMR (DMSO-d₆, δ): 1.30 (9H, s), 2.30 (2H, br d, J=6Hz), 2.6–3.2 (4H, m), 4.0–4.9 (3H, m), 5.12 (2H, s), 6.89 (2H, br s), 7.1–7.7 (5H, m), 7.24 (5H, s), 7.36 (5H, s), 7.93 (1H, br d, J=8Hz), 8.2 (1H, br s), 8.68 (1H, br d, J=8Hz), 9.3 (1H, br s).

Elemental Analysis. Calculated for $C_{37}H_{41}N_5O_8$: C 64.99, H 6.04, N 10.21; Found: C 65.36, H 6.36, N 10.21.

(3)

Starting Compound: HCl.H—D—Trp(CHO)—Phe—OBzl

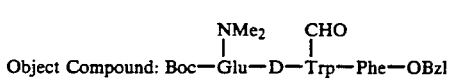

Object Compound: Boc—Glu(NMe₂)—D—Trp(CHO)—Phe—OBzl mp: 95°–100° C.

IR (Nujol): 3280, 1750, 1720 (sh), 1710, 1690 (sh), 1655, 1640, 1560 cm⁻¹.

NMR (DMSO-d₆, δ): 1.31 (9H, s), 1.4–2.1 (4H, m), 2.6–3.3 (4H, m), 2.67 (3H, s), 2.75 (3H, s), 3.8–4.2 (1H, m), 4.4–5.0 (2H, m), 5.14 (2H, s), 6.75 (1H, br s), 7.2–7.8

(4H, m), 7.25 (5H, s), 7.37 (5H, s), 7.8–8.4 (2H, m), 8.73 (1H, br d, J=8Hz), 9.3 (1H, br s).

Elemental Analysis. Calculated for $C_{40}H_{47}N_5O_8$: C 66.19, H 6.53, N 9.65; Found: C 66.38, H 6.59, N 9.21.

(4)

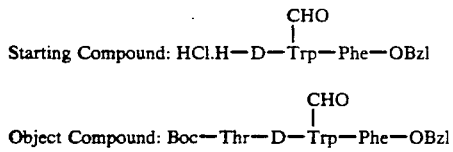

mp: 158°–160° C.

IR (Nujol): 3340, 3290 (sh), 1720, 1685, 1640, 1540 (sh), 1530 cm$^{-1}$.

NMR (DMSO-d$_6$, δ): 0.83 (3H, d, J=6Hz), 1.33 (9H, s), 2.7–3.2 (4H, m), 3.7–4.1 (2H, m), 4.4–5.0 (3H, m), 5.10 (2H, s), 6.2–6.5 (1H, m), 7.2–7.8 (4H, m), 7.21 (5H, s), 7.33 (5H, s), 7.9–8.4 (2H, m), 8.62 (1H, br d, J=9Hz), 9.3 (1H, br s).

Elemental Analysis. Calculated for $C_{37}H_{42}N_4O_8$: C 66.25, H 6.31, N 8.35; Found: C 66.11, H 6.20, N 8.35.

(5)

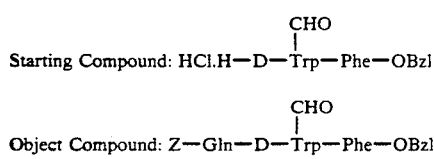

mp: 266°–267° C.

IR (Nujol): 3450, 3340, 3290, 1720, 1690, 1655, 1640, 1555, 1545 (sh) cm$^{-1}$.

NMR (DMSO-d$_6$, δ): 1.4–2.1 (4H, m), 2.6–3.2 (4H, m), 3.8–4.3 (1H, m), 4.4–4.9 (2H, m), 5.00 (2H, s), 5.12 (2H, s), 6.72 (1H, br s), 7.0–7.8 (6H, m), 7.23 (5H, s), 7.34 (10H, s), 8.10 (2H, br d, J=8Hz), 8.69 (1H, br d, J=9Hz), 9.3 (1H, br s).

Elemental Analysis. Calculated for $C_{41}H_{41}N_5O_8$: C 67.29, H 5.65, N 8.57; Found: C 67.63, H 5.42, N 9.48.

(6)

Starting Compound: HCl H-D-Trp-Phe-OBzl

Object Compound: Boc-Gln-D-Trp-Phe-OBzl mp: 195°–197° C.

IR (Nujol): 3420, 3340, 3300, 3240, 1735, 1690, 1665, 1640, 1620, 1540, 1525 cm$^{-1}$.

NMR (DMSO-d$_6$, δ): 1.33 (9H, s), 1.4–2.2 (4H, m), 2.6–3.2 (4H, m), 3.7–4.2 (1H, m), 4.3–4.8 2H, m), 5.09 (2H, s), 6.5–7.6 (19H, m), 7.90 (1H, br d, J=8Hz), 8.51 (1H, br d, J=9Hz).

Elemental Analysis. Calculated for $C_{37}H_{43}N_5O_7$: C 66.35, H 6.47, N 10.46; Found: C 66.37, H 6.39, N 10.41.

EXAMPLE 13

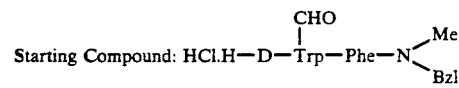

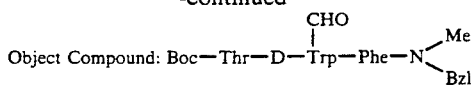

Boc-Thr-OH (1.23 g), HCl.H-D-Trp(CHO)-Phe-NMeBzl (3.0 g) and HOBT (0.757 g) were dissolved in DMF (40 ml). To this solution was added WSC (887 mg) under ice cooling and the mixture was stirred for 1.5 hours at the same temperature and overnight at room temperature. After evaporation and extraction with ethyl acetate, the organic layer was washed successively with water, diluted sodium hydrogencarbonate solution, water, 0.5N hydrochloric acid, and sodium chloride solution and dried over magnesium sulfate. The evaporated residue was crystallized from a mixed solvent of ethyl acetate and diisopropyl ether (1:1) (10 ml) with seeding and the crystals were washed out by addition of diisopropyl ether (30 ml) and dried to give Boc-Thr-D-Trp(CHO)-Phe-NMeBzl (3.64 g).

mp: 104.5°–111° C. (dec.).

IR (Nujol): 3360, 3220, 3070, 1718, 1690, 1668, 1650, 1626, 1560, 1530 cm$^{-1}$.

NMR (DMSO-d$_6$, δ): 0.84 (3H, d, J=6Hz), 1.34 (9H, s), 2.77 (s) and 2.87 (s)(3H), 2.5–3.2 (4H, m), 3.75–3.9 (2H, m), 4.18–5.20 (5H, m), 6.25 (1H, d, J=7Hz), 6.9–7.7 (14H, m), 7.8–8.2 (2H, m), 8.4–8.8 (1H, m), 9.0–9.5 (1H, br s).

Elemental Analysis. Calculated for $C_{38}H_{45}N_5O_7$: C 66.75, H 6.63, N 10.24; Found: C 66.72, H 6.55, N 10.19. $[\alpha]_D^{25}$ +39.03° (c 1.135, CHCl$_3$).

EXAMPLE 14

The following object compounds were obtained from the corresponding starting compounds according to a similar manner to that of Example 13.

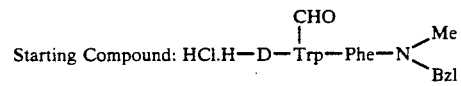

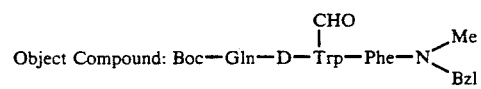

mp: 197°–199° C.

IR (Nujol): 3340, 3350 (sh), 3300, 3240 (sh), 1715, 1690, 1665, 1650, 1635, 1550, 1530 cm$^{-1}$.

NMR (DMSO-d$_6$, δ): 1.33 (9H, s), 1.5–2.2 (4H, m), 2.6–3.2 (4H, m), 2.79 (s) and 2.87 (s)(3H), 3.7–4.2 (1H, m), 4.2–5.3 (4H, m), 6.7 (2H, br s), 7.0–7.6 (14H, m), 7.6–7.9 (1H, m), 7.9–8.4 (2H, m), 8.7 (1H, br s), 9.3 (1H, br s).

Elemental Analysis. Calculated for $C_{39}H_{46}N_6O_7$: C 65.90, H 6.52, N 11.82; Found: C 65.86, H 6.41, N 11.86.

(2)

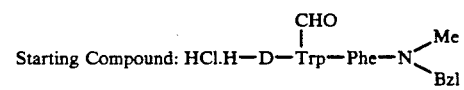

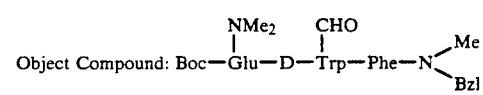

mp: ~110° C. (dec.).

IR (Nujol): 3300, 1710, 1635, 1525 (sh), 1510 (sh), 1490 cm$^{-1}$.

NMR (DMSO-d$_6$, δ): 1.33 (9H, s), 1.3–2.1 (4H, m), 2.6–3.2 (4H, m), 2.69 (3H, s), 2.77 (3H, s), 2.82 (s) and 2.91 (s)(3H), 3.8–4.1 (1H, m), 4.2–5.2 (4H, m), 6.77 (1H, br d, J=6Hz), 7.0–7 7 (13H, m), 7.7–7.9 (1H, m), 7.9–8.3 (2H, m), 8.5–8.9 (1H, m), 9.3 (1H, br s).

Elemental Analysis. Calculated for C$_{41}$H$_{50}$N$_6$O$_7$: C 66.65, H 6.82, N 11.37; Found: C 66.78, H 7.12, N 10.92.

EXAMPLE 15

Starting Compound: Boc—Thr—D—Trp(CHO)—Phe—N(Me)(Bzl)

Object Compound: HCl.H—Thr—D—Trp(CHO)—Phe—N(Me)(Bzl)

Boc-Thr-D-Trp(CHO)-Phe-NMeBzl (2.54 g) and anisole (2.5 ml) were dissolved in methylene chloride (25 ml) and ice-cooled. To this solution was added 4N-HCl/DOX (25 ml). The reaction mixture was stirred for an hour at room temperature. After evaporation, the residue was triturated with diisopropyl ether, filtered, washed with diisopropyl ether, and dried to give HCl.H-Thr-D-Trp(CHO)-Phe-NMeBzl (2.30 g).

NMR (DMSO-d$_6$, δ): 0.77 (3H, tr, J=6Hz), 2.80 (s), and 2.88 (s)(3H), 2.6–3.0 (4H, m), 3.5–3.8 (2H, m), 4.15–5.1 (5H, m), 6.95–7.4 (14H, m) 7.4–7.8 (2H, m), 8.10 (3H, br s), 8.6–9.0 (2H, m), 9.1–9.7 (1H, br).

EXAMPLE 16

The following object compounds were obtained from the corresponding starting compounds according to a similar manner to that of Example 15.

(1)

Starting Compound: Boc—Gln—D—Trp(CHO)—Phe—OBzl

Object Compound: HCl.H—Gln—D—Trp(CHO)—Phe—OBzl mp: ~168° C. (dec.).

IR (Nujol): 3200 (broad), 1735 (sh), 1710 (sh), 1690 (sh), 1675 (sh), 1660, 1605, 1530 (broad) cm$^{-1}$.

NMR (DMSO-d$_6$, δ): 1.5–2.2 (4H, m), 2.6–3.3 (4H, m), 3.6–4.0 (1H, m), 4.4–5.0 (2H, m), 5.14 (2H, s), 6.90 (1H, br s), 7.0–7.8 (5H, m), 7.27 (5H, s), 7.38 (5H, s), 8.33 (4H, br s), 8.7–9.2 (2H, m), 9.3 (1H, br s).

(2)

Starting Compound: Boc—Glu(NMe$_2$)—D—Trp(CHO)—Phe—N(Me)(Bzl)

Object Compound: HCl.H—Glu(NMe$_2$)—D—Trp(CHO)—Phe—N(Me)(Bzl)

IR (Nujol): 3400 (sh), 3200 (broad), 1710 (broad), 1630, 1490 cm$^{-1}$.

NMR (DMSO-d$_6$, δ): 1.4–2.3 (4H, m), 2.5–3.2 (4H, m), 2.57 (3H, s), 2.77 (3H, s), 2.85 (s) and 2.96 (s)(3H), 3.6–4.0 (1H, m), 4.2–5.2 (4H, m), 7.0–7.7 (14H, m), 7.7–8.0 (1H, m), 8.22 (3H, br s), 8.6–9.6 (3H, m).

EXAMPLE 17

Starting Compound: HCl.H—Thr—D—Trp(CHO)—Phe—N(Me)(Bzl)

Object Compound: Ac—Thr—D—Trp(CHO)—Phe—N(Me)(Bzl)

To a solution of HCl.H-Thr-D-Trp(CHO)-Phe-NMeBzl (2.29 g) in methylene chloride (30 ml), were added triethylamine (747 mg) and Ac$_2$O (377 mg) at −20° C. The reaction mixture was stirred for 45 minutes at the same temperature, and washed successively with water, diluted sodium hydrogencarbonate solution, water, 0.5N hydrochloric acid, and sodium chloride solution and dried over magnesium sulfate. After concentration, the residue was dissolved in 65% aqueous ethanol (45 ml) under heating, and the solution was left standing overnight at room temperature. The resulting needles were filtered, washed with 65% aqueous ethanol, and dried to give Ac-Thr-D-Trp(CHO)-Phe-NMeBzl (1.92 g).

mp: 179.5°–180.5° C.

IR (Nujol): 3450 (sh), 3260, 1720 (sh), 1698, 1660 (sh), 1645–1620 (broad), 1550 cm$^{-1}$.

NMR (DMSO-d$_6$, δ): 0.80 (3H, d, J=6Hz), 1.87 (3H, s), 2.80 (s) and 2.87 (s)(3H), 2.6–3.2 (4H, m), 3.6–3.9 (1H, m), 3.95–4.3 (1H, m), 4.3–5.2 (5H, m), 6.95–7.8 (15H, m), 7.8–8.3 (2H, m), 8.5–8.75 (1H, m), 9.0–9.7 (1H, br s).

Elemental Analysis. Calculated for C$_{35}$H$_{39}$N$_5$O$_6$·H$_2$O: C 65.30, H 6.42, N 10.88; Found: C 65.54, H 6.41, N 10.99.

$[\alpha]_D^{25}$ +20.03° (c 1.078, DMF).

EXAMPLE 18

The following object compounds were obtained from the corresponding starting compounds according to a similar manner to that of Example 17.

(1)

Starting Compound: HCl.H—Gln—D—Trp(CHO)—Phe—OBzl

Object Compound: Ac—Gln—D—Trp(CHO)—Phe—OBzl mp: ~233° C. (dec.).

IR (Nujol): 3420, 3290, 3220 (sh), 1725, 1710, 1655, 1640, 1630 (sh), 1545 cm$^{-1}$.

NMR (DMSO-d$_6$, δ): 1.4–2.1 (4H, m), 1.80 (3H, s) 2.6–3.2 (4H, m), 4.0–4.4 (1H, m), 4.4–4.8 (2H, m), 5.13 (2H, s), 6.70 (1H, br s), 7.0–7.8 (5H, m), 7.23 (5H, s), 7.35 (5H, s), 8.00 (1H, br d, J=9Hz), 8.21 (2H, br d, J=9Hz), 8.68 (1H, br d, J=8Hz), 9.30 (1H, br d).

Elemental Analysis. Calculated for C$_{35}$H$_{37}$N$_5$O$_7$: C 65.72, H 5.83, N 10.95; Found: C 65.32, H 5.78, N 10.95.

(2)

Starting Compound:

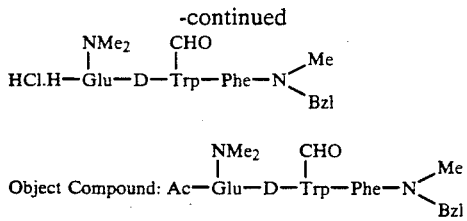

mp: ~120° C. (dec.).

IR (Nujol): 3300, 1710, 1640 (broad), 1545 (sh), 1530, 1490 cm$^{-1}$.

NMR (DMSO-d$_6$, δ): 1.3-2.1 (4H, m), 1.79 (3H, s), 2.5-3.2 (4H, m), 2.63 (3h, s), 2.73 (3H, s), 2.82 (s) and 2.90 (s)(3H), 4.0-5.2 (5H, m), 6.9-7.6 (13H, m), 7.6-8.3 (4H, m), 8.5-8.9 (1H, m), 9.3 (1H, br s).

Elemental Analysis. Calculated for C$_{38}$H$_{44}$N$_6$O$_6$.1/2-H$_2$O: C 66.17, H 6.58, N 12.18; Found: C 65.99, H 6.65, N 11.94.

EXAMPLE 19

The following object compound was obtained from the corresponding starting compound according to similar manners to those of Example 4 and Example 13, successively.

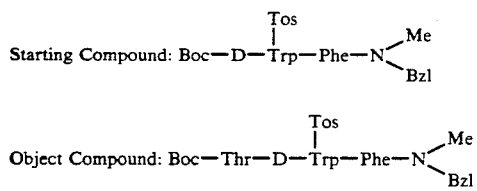

mp: 95°-96° C.

IR (Nujol): 3350, 1695, 1655, 1620 cm$^{-1}$.

NMR (DMSO-d$_6$, δ): 0.86 (3H, d, J=6Hz), 1.38 (9H, s), 2.27 (3H, s), 2.72 and 2.80 (3H, s), 2.6-3.2 (4H, m), 3.7-4.05 (2H, m), 4.2-5.1 (6H, m), 6.33 (1H, d, J=6Hz), 6.95-7.9 (19H, m), 8.0-8.2 (1H, m), 8.5-8.75 (1H, m).

Elemental Analysis. Calculated for C$_{44}$H$_{51}$N$_5$O$_8$S$_1$: C 65.25, H 6.35, N 8.65; Found: C 64.97, H 6.39, N 8.51.

EXAMPLE 20

The following object compounds were obtained from the corresponding starting compounds according to a similar manner to that of Example 11.

(1)

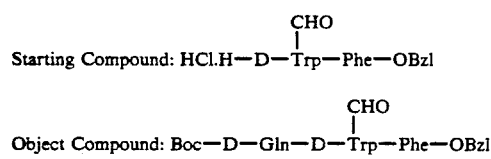

mp: 170°-172° C.

IR (Nujol): 3300, 1720, 1660, 1640, 1550, 1525 cm$^{-1}$.

NMR (DMSO-d$_6$, δ): 1.32 (9H, s), 1.5-2.2 (4H, m), 2.6-3.2 (4H, m), 3.6-4.1 (1H, m), 4.4-4.9 (2H, m), 5.12 (2H, s), 6.6-7.0 (2H, m), 7.0-7.7 (5H, m), 7.25 (5H, s), 7.36 (5H, s), 7.90 (1H, br d, J=9Hz), 8.0-8.3 (1H, m), 8.76 (1H, br d, J=8Hz), 9.2 (1H, broad).

(2)

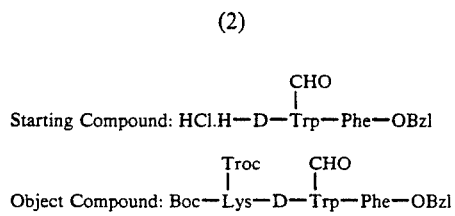

mp: 160°-162° C.

IR (Nujol): 3350, 3300, 1720, 1710, 1690, 1645, 1545, 1520 cm$^{-1}$.

NMR (DMSO-d$_6$, δ): 0.8-1.5 (6H m) 1.32 (9H, s), 2.5-3.1 (6H, m), 3.7-4.0 (1H, m), 4.4-4.8 (2H, m), 4.81 (2H, s), 5.15 (2H, s), 6.6-6.8 (1H, m), 7.1-7.8 (5H, m), 7.27 (5H, s), 7.39 (5H, s), 7.9-8.4 (2H, m), 8.5-8.8 (1H, m), 9.3 (1H, broad).

EXAMPLE 21

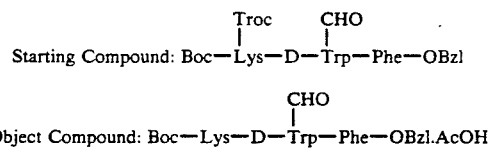

To a solution of Boc-Lys(Troc)-D-Trp(CHO)-Phe-OBzl (0.94 g) in 90% AcOH (20 ml) was added zinc (0.94 g) and the mixture was stirred overnight at room temperature. Insoluble materials were filtered off and the filtrate was evaporated. The residue was subjected to column chromatography on silica gel (50 g) and eluted successively with a mixture of chloroform and methanol (10:1) and then a mixture of chloroform, methanol and AcOH (8:1:1). The fractions containing the object compound were combined and evaporated. The residue was pulverized with n-hexane, filtered, washed with n-hexane, and dried to give Boc-Lys-D-Trp(CHO)-Phe-OBzl AcOH (0.42 g).

mp: ~175° C. (dec.).

IR (Nujol): 3320, 1690 (broad), 1640, 1550, 1525 cm$^{-1}$.

NMR (DMSO-d$_6$, δ): 0.8-1.5 (6H, m). 1.32 (9H, s), 1.87 (3H, s), 2.5-3.2 (6H, m), 3.8-4.1 (1H, m), 4.3-5.5 (5H, m), 5.12 (2H, s), 6.6-6.8 (1H, m), 6.8-7.1 (1H, m), 7.1-7.8 (3H, m), 7.23 (5H, s), 7.33 (5H, s), 7.9-8.3 (2H, m), 8.6-8.9 (1H, m), 9.3 (1H, broad).

EXAMPLE 22

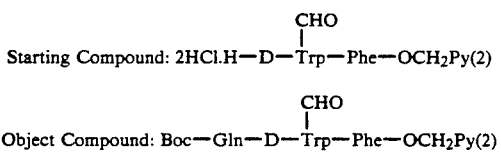

To a solution of 2HCl.H-D-Trp(CHO)-Phe-OCH$_2$Py(2) (0.74 g), BOC-Gln-OH (0.30 g) and HOBT (0.16 g) in DMF (15 ml) were added N,N-diisopropyl-N-ethylamine (0.21 ml) and WSC (0.22 ml) successively under ice cooling, and the mixture was stirred for two hours at room temperature. After evaporation, the residue was pulverized with water, filtered, and washed with water, 2% sodium hydrogen-carbonate solution and water. The solids were dissolved in DMF and reprecipitated with ethyl acetate, filtered and dried to give Boc-Gln-D-Trp(CHO)-Phe-OCH$_2$Py(2) (0.66 g).

mp: 166°-170° C.

IR (Nujol): 3300, 1740, 1710, 1690, 1650 (broad), 1525 cm$^{-1}$.

NMR (DMSO-d$_6$, δ): 1.31 (9H, s), 1.4-2.1 (4H, m), 2.6-3 2 (4H, m), 3.7-4.1 (1H, m), 4.4-4.9 (2H, m), 5.21 (2H, s), 6.6-6.9 (2H, m), 7.0-8.3 (15H, m), 8.5-8.6 (1H, m), 8.6-8.8 (1H, m), 9.3 (1H, broad).

Elemental Analysis. Calculated for C$_{37}$H$_{42}$N$_6$O$_8$: C 63.60, H 6.06, N 12.03; Found: C 63.29, H 6.13, N 12.00.

EXAMPLE 23

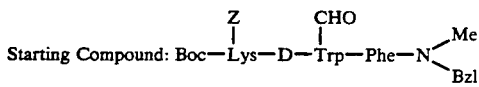

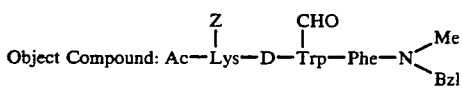

To a solution of Boc-Lys(Z)-D-Trp(CHO)-Phe-NMeBzl (1.04 g) in methylene chloride (10 ml) was added 4N-HCl/DOX (10 ml) under ice-cooling. The mixture was stirred for an hour at room temperature. After evaporation, the residue was pulverized with diisopropyl ether, filtered, washed with diisopropyl ether and dried. The obtained HCl.H-Lys(Z)-D-Trp(CHO)-Phe-NMeBzl (0.94 g) was dissolved in methylene chloride (15 ml) and cooled in an ice-bath. To the solution were added triethylamine (0.34 ml) and Ac$_2$O (0.11 ml) and the mixture was stirred for an hour at the same temperature. After evaporation and extraction with ethyl acetate, the organic layer was washed successively with water, 2% hydrochloric acid, water, 2% sodium hydrogencarbonate, water and saturated sodium chloride, and then dried over magnesium sulfate. The evaporated residue was subjected to column chromatography on silica gel (50 g) and eluted with a mixture of chloroform and methanol (50 ml). The fractions containing the object compound were combined and evaporated. The residue was pulverized with n-hexane, filtered, and dried to give Ac-Lys(Z)-D-Trp(CHO)-Phe-NMeBzl (0.82 g).

mp: ~174° C. (dec.).

IR (Nujol): 3300, 1710, 1690, 1640, 1540 (broad) cm$^{-1}$.

NMR (DMSO-d$_6$, δ): 0.8-1.5 (6H, m), 1.78 (3H, s), 2.6-3.2 (6H, m), 2.78 (s) and 2.87 (s) (3H), 4.0-5.2 (5H, m), 4.98 (2H, s), 6.9-7.6 (19H, m), 7.6-7.9 (2H, m), 7.9-8.3 (2H, m), 8.64 (1H, br t, J=9Hz), 9.3 (1H, broad).

Elemental Analysis. Calculated for C$_{45}$H$_{50}$N$_6$O$_7$: C 68.68, H 6.40, N 10.68; Found: C 68.33, H 6.22, N 10.53.

EXAMPLE 24

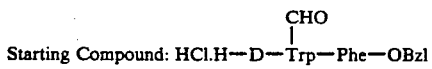

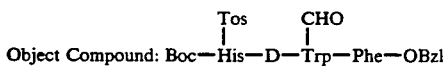

To a solution of Boc-His(Tos)-OH (0.81 g) in methylene chloride (10 ml) were added NMM (0.22 ml) and isobutyl chloroformate (0.26 ml) successively at −15° C., and the mixture was stirred for ten minutes. On the other hand, a solution of HCl.H-D-Trp(CHO)-Phe-OBzl (1.00 g) in DMF (20 ml) was cooled at −30° C. and thereto was added NMM (0.22 ml). This solution was added to the above mentioned mixture and stirred for two hours at −30° C. After evaporation and extraction with ethyl acetate, the organic layer was washed successively with 2% hydrochloric acid, water, 2% sodium hydrogencarbonate, water and saturated sodium chloride solution, and dried over magnesium sulfate. After evaporation, the residue was subjected to column chromatography on silica gel (100 g) and eluted with a mixture of chloroform and methanol (100:1). The fractions containing the object compound were combined and evaporated. The residue was pulverized with n-hexane, filtered, washed with n-hexane and dried to give Boc-His(Tos)-D-Trp(CHO)-Phe-OBzl (1.42 g).

mp: 107°-111° C.

IR (Nujol): 3300, 1700 (broad), 1645 cm$^{-1}$.

NMR (DMSO-d$_6$, δ): 1.30 (9H, s), 2.37 (3H, s), 2.4-3.1 (6H, m), 4.0-4.4 (1H, m), 4.4-4.9 (2H, m), 5.14 (2H, s), 6.7-6.9 (1H, m), 7.1-7.7 (6H, m), 7.25 (5H, s), 7.37 (5H, s), 7.50 (2H, d, J=8Hz), 7.94 (2H, d, J=8Hz), 7.9-8.3 (1H, m), 8.32 (1H, s), 8.75 (1H, br d, J=7Hz), 9.3 (1H, broad).

Elemental Analysis. Calculated for C$_{46}$H$_{48}$N$_6$O$_9$S: C 64.17, H 5.62, N 9.76; Found: C 64.00, H 5.76, N 9.61.

EXAMPLE 25

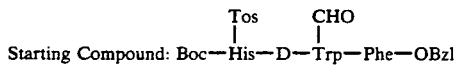

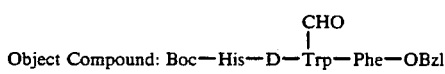

To a solution of Boc-His(Tos)-D-Trp(CHO)-Phe-OBzl (1.16 g) in DMF (35 ml) was added pyridinium chloride (1.6 g) at room temperature. After stirring for one and half an hour, additional pyridinium chloride (0.4 g) was added and the mixture was stirred for additional 50 minutes. After evaporation, the residue was solidified with water, filtered, washed with 2% hydrochloric acid, water, 2% sodium hydrogencarbonate, water, and dried. The powder was subjected to column chromatography on silica gel (100 g) and eluted with a mixture of chloroform and methanol (20:1). The fractions containing the object compound were combined and evaporated. The residue was dissolved in ethanol and reprecipitated with water, filtered and dried to give Boc-His-D-Trp(CHO)-Phe-OBzl (0.70 g).

mp: 112°-115° C.

IR (Nujol): 3300, 1710 (broad), 1640 cm$^{-1}$.

NMR (DMSO-d$_6$, δ): 1.25 (9H, s), 2.5-3.1 (6H, m), 3.8-4.3 (1H, m), 4.3-4.8 (2H, m), 5.03 (2H, s), 6.5-6.7 (1H, m), 6.54 (1H, s), 7.0-7.6 (4H, m), 7.13 (5H, s), 7.27 (5H, s), 7.44 (1H, s), 7.8-8.3 (2H, m), 8.66 (1H, br d, J=9Hz), 9.2 (1H, broad).

Elemental Analysis. Calculated for C$_{39}$H$_{42}$N$_6$O$_7$.1/2-H$_2$O: C 65.44, H 6.05, N 11.74; Found: C 65.59, H 5.90, N 11.84.

EXAMPLE 26

The following object compounds were obtained from the corresponding starting compounds according to a similar manner to that of Example 13.

(1)

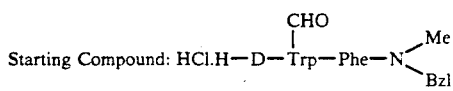

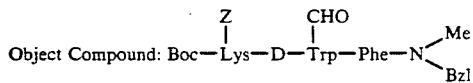

mp: 74°–80° C.

IR (Nujol): 3300, 1710, 1640 cm$^{-1}$.

NMR (DMSO-d$_6$, δ): 0.8–1.5 (6H, m), 1.30 (9H, s), 2.5–3.1 (6H, m), 2.77 (s) and 2.80 (s)(3H), 3.6–4.0 (4H, m), 4.2–5.0 (4H, m), 4.97 (2H, s), 6.6 (1H, broad), 6.9–7.5 (19H, m), 7.5–7.8 (1H, m), 7.8–8.3 (2H, m), 8.45–8.85 (1H, m), 9.3 (1H, broad).

Elemental Analysis. Calculated for C$_{48}$H$_{56}$N$_6$O$_8$.1/2-H$_2$O: C 67.51, H 6.73, N 9.84; Found: C 67.32, H 6.47, N 9.69.

(2)

Starting Compound: HCl.H—D—Trp—Phe—N(Me)(Bzl) with CHO on Trp

Object Compound: Boc—Asp(—D—Trp—Phe—N(Me)(Bzl))—NH$_2$ with CHO on Trp mp: 213°–216° C.

IR (Nujol): 3400, 3340, 3300, 3230, 1715, 1670, 1640, 1525 cm$^{-1}$.

NMR (DMSO-d$_6$, δ): 1.30 (9H, s), 2.3–2.5 (2H, m), 2.6–3.2 (4H, m), 2.76 (s) and 2.83 (s) (3H), 4.0–5.1 (5H, m), 6.6–7.7 (17H, m), 7.8–8.3 (2H, m), 8.4–8.8 (1H, m), 9.3 (1H, broad).

Elemental Analysis. Calculated for C$_{38}$H$_{44}$N$_6$O$_7$: C 65.50, H 6.36, N 12.06; Found: C 65.15, H 6.28, N 11.98.

(3)

Starting Compound: HCl.H—D—Trp—Phe—N(Me)(Bzl) with CHO on Trp

Object Compound: Boc—Orn(Z)—D—Trp(CHO)—Phe—N(Me)(Bzl)

mp: ~171° C.

IR (Nujol): 3330, 3300, 1710, 1695, 1645, 1530 (broad) cm$^{-1}$.

NMR (DMSO-d$_6$, δ): 0.9–1.5 (4H, m), 1.33 (9H, s), 2.5–3.1 (6H, m), 2.77 (s) and 2.85(s)(3H), 3.7–4.0 (1H, m), 4.1–5.1 (4H, m), 4.97 (2H, s), 6.63 (1H, br d, J=7Hz), 6.9–7.5 (19H, m), 7.5–7.8 (1H, m), 7.8–8.3 (2H, m), 8.5–8.8 (1H, m), 9.2 (1H, broad).

Elemental Analysis. Calculated for C$_{47}$H$_{54}$N$_6$O$_8$: C 67.93, H 6.55, N 10.11; Found: C 67.63, H 6.76, N 10.02.

(4)

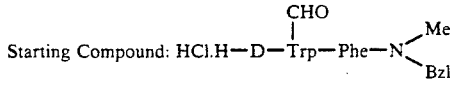

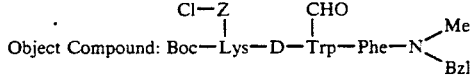

mp: ~124° C. (dec.).

IR (Nujol): 3300, 1690 (broad), 1645, 1530 (broad) cm$^{-1}$.

NMR (DMSO-d$_6$, δ): 0.8–1.5 (6H, m), 1.30 (9H, s), 2.5–3.1 (6H, m), 2.68 (s) and 2.76 (s)(3H), 3.6–4.0 (1H, m), 4.1–5.1 (4H, m), 4.95 (2H, s), 6.55 (1H, broad), 6.8–7.8 (19H, m), 7.8–8.3 (2H, m), 8.3–8.8 (1H, m), 9.25 (1H, broad).

Elemental Analysis. Calculated for C$_{48}$H$_{55}$ClN$_6$O$_8$: C 65.56, H 6.30, N 9.56; Found: C 65.61, H 6.29, N 9.52.

(5)

Starting Compound: HCl.H—D—Trp(CHO)—Phe—N(Me)(Bzl)

Object Compound: Boc—Ser—D—Trp(CHO)—Phe—N(Me)(Bzl)

mp: ~112° C. (dec.).

IR (Nujol): 3300, 1710, 1640 cm$^{-1}$.

NMR (DMSO-d$_6$, δ): 1.34 (9H, s), 2.5–3.1 (4H, m), 2.77 (s) and 2.9 (s)(3H), 3.42 (2H, br t, J=6Hz), 3.7–5.1 (6H, m), 6.51 (1H, br d, J=7Hz), 6.9–7.7 (14H, m), 7.8–8.2 (2H, m), 8.64 (1H, br t, J=8Hz), 9.15 (1H, broad).

(6)

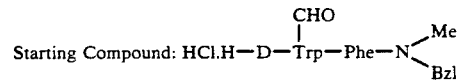

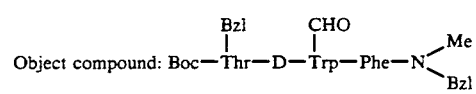

mp: 185°–186° C.

IR (Nujol): 3350, 3300, 1695, 1645, 1630 (broad) cm$^{-1}$.

NMR (DMSO-d$_6$, δ): 0.83 (3H, d, J=6Hz), 1.34 (9H, s), 2.5–3.1 (4H, m), 2.76 (s) and 2.85 (s)(3H), 3.4–3.7 (1H, m), 3.8–5.2 (7H, m), 6.17 (1H, br d, J=9Hz), 6.9–7.6 (18H, m), 7.6–7.8 (1H, m), 7.8–8.3 (2H, m), 8.75 (1H, br t, J=9Hz), 9.2 (1H, broad).

Elemental Analysis. Calculated for C$_{45}$H$_{51}$N$_5$O$_7$.1/2-H$_2$O: C 69.03, H 6.69, N 8.94; Found: C 68.99, H 6.40, N 8.97.

EXAMPLE 27

The following object compound are obtained from the corresponding starting compounds according to a similar manner to that of Example 23.

(1)

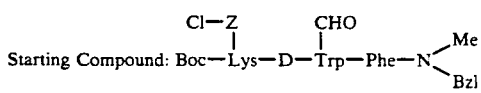

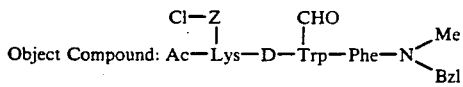

mp: 190°-192° C.

IR (Nujol): 3300, 1710, 1690, 1640, 1545 (broad) cm$^{-1}$.

NMR (DMSO-d$_6$, δ): 0.7-1.5 (6H, m), 1.70 (3H, s), 2.5-3.1 (6H, m), 2.70 (s) and 2.80 (s)(3H), 3.9-5.1 (5H m) 4.98 (2H, s), 6.9-7.5 (18H, m), 7.5-7.9 (2H, m), 7.9-8.3 (2H, m), 8.57 (1H, br t, J=9Hz), 9.3 (1H, broad).

Elemental Analysis. Calculated for C$_{45}$H$_{49}$ClN$_6$O$_7$: C 65.80, H 6.01, N 10.23; Found: C 65.72, H 6.00, N 10.18.

(2)

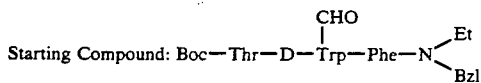

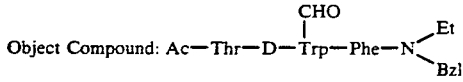

mp: 187°-189° C.

IR (Nujol): 3510, 3340, 3300, 1710, 1660, 1550 (broad) cm$^{-1}$.

NMR (DMSO-d$_6$, δ): 0.78 (3H, d, J=6Hz), 0.96 (3H, t, J=7Hz), 1.85 (3H, s), 2.6-3.1 (4H, m), 3.1-3.5 (2H, m), 3.6-3.95 (1H, m), 4.0-4.3 (1H, m), 4.35-5.15 (5H, m), 7.0-7.8 (15H, m), 7.9-8.3 2H, m), 8.62 (1H, br d, J=9Hz), 9.3 (1H, broad).

Elemental Analysis. Calculated for C$_{36}$H$_{41}$N$_5$O$_6$.1/2-H$_2$O: C 66.65, H 6.53, N 10.80; Found: C 66.35, H 6.21, N 10.79.

EXAMPLE 28

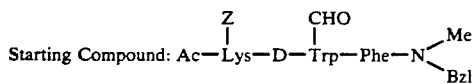

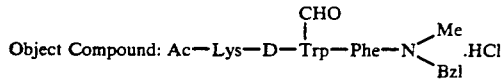

Ac-Lys(Z)-D-Trp(CHO)-Phe-NMeBzl (0.54 g) was hydrogenated in AcOH (20 ml) with 10% palladium on carbon (0.10 g). The catalyst was filtered off and the filtrate was concentrated under reduced pressure. The residue was dissolved in methanol. To the solution was added 4N-HCl/DOx (0.35 ml) and evaporated. The residue was dissolved in ethanol and the solution was treated with activated charcoal. The charcoal was filtered off and the filtrate was concentrated under reduced pressure. The residue was pulverized with diisopropyl ether, filtered, washed with diisopropyl ether and dried to give Ac-Lys-D-Trp(CHO)-Phe-NMeBzl.HCl (0.45 g).

IR (Nujol): 3250 (broad), 1640 (broad), 1540 (broad) cm$^{-1}$.

NMR (DMSO-d$_6$, δ): 0.8-1.8 (6H, m), 1.77 (3H, s), 2.5-3 1 (6H, m), 2.77 (s) and 2.86 (s)(3H), 3.3-4.0 (3H, broad), 4.0-5.2 (5H, m), 6.9-7.6 (11H, m), 7.6-8.4 (6H, m), 8.5-8.8 (1H, m), 9.4 (1H, broad).

EXAMPLE 29

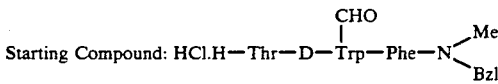

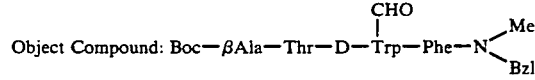

Boc-βAla-OH (0.19 g), HCl.H-Thr-D-Trp(CHO)-Phe-NMeBzl (0.62 g) and HOBT (0.14 g) were dissolved in DMF (10 ml). To this solution was added WSC (0.18 ml) under ice cooling and the mixture was stirred for four hours at room temperature. After evaporation and extraction with ethyl acetate, the organic layer was washed successively with water, 2% sodium hydrogencarbonate solution, water, 2% hydrochloric acid, water and saturated sodium chloride solution, and dried over magnesium sulfate. The evaporated residue was crystallized from a mixed solvent of ethanol and water. Filtration and drying gave Boc-βAla-Thr-D-Trp(CHO)-Phe-NMeBzl (0.66 g).

mp: 182°-192° C. (dec.).

IR (Nujol): 3430, 3350, 3300, 1705, 1690, 1640, 1530 cm$^{-1}$.

NMR (DMSO-d$_6$, δ): 0.80 (3H, t, J=6Hz), 1.35 (9H, s), 2.33 (2H, t, J=7Hz), 2.5-3.3 (4H, m), 2.77 (s) and 2.84 (s)(3H), 3.07 (2H, t, J=7Hz), 3.6-3.9 (1H, m), 3.9-4.3 (1H, m), 4.3-5.2 (5H, m), 6.6 (1H, br s), 6.9-7.8 (15H, m), 7.8-8.3 (2H, m), 8.60 (1H, br t, J=9Hz), 9.2 (1H, br s).

Elemental Analysis. Calculated for C$_{41}$H$_{50}$N$_6$O$_8$: C 65.24, H 6.68, N 11.13; Found: C 65.06, H 6.70, N 11.16.

EXAMPLE 30

The following object compound was obtained from the corresponding starting compound according to similar manners to those of Example 2 and Example 22, successively.

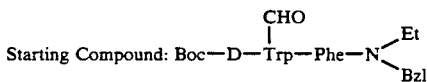

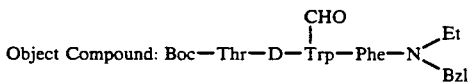

mp: 90°-94° C.

IR (Nujol): 3320, 1710, 1635 (broad) cm$^{-1}$.

NMR (DMSO-d$_6$, δ): 0.7-1.1 (6H, m), 1.33 (9H, s), 2.5-3.4 (6H, m), 3.6-4.0 (2H, m), 4.2-5.2 (5H, m), 6.27 (1H, br d, J=9Hz), 6.9-7.8 (14H, m), 7.8-8.3 (2H, m), 8.66 (1H, br d, J=9Hz), 9.2 (1H, broad).

Elemental Analysis. Calculated for C$_{39}$H$_{47}$N$_5$O$_7$.-H$_2$O: C 65.44, H 6.90, N 9.78; Found: C 65.65, H 6.66, N 9.45.

EXAMPLE 31

The following object compounds were obtained from the corresponding starting compounds according to a similar manner to that of Example 15.

(1)

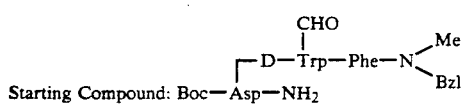

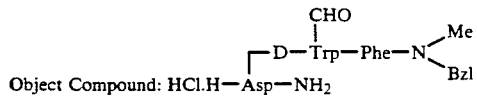

mp: ~178° C. (dec.).

IR (Nujol) 3250 (broad), 1700 (broad), 1640 (broad) cm$^{-1}$.

NMR (DMSO-d$_6$, δ): 2.5-3.1 (6H, m), 2.78 (s) and 2.86 (s)(3H), 3.8-5.1 (5H, m), 6.9-7.9 (16H, m), 8.2 (4H, br s), 8.3-8.6 (1H, m), 8.77 (1H, br t, J=9Hz), 9.3 (1H, broad).

(2)

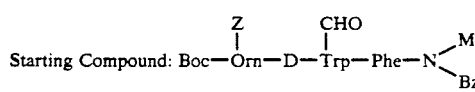

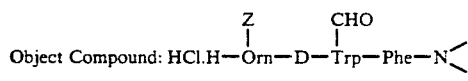

NMR (DMSO-d$_6$, δ): 0.9-1.7 (4H, m), 2.5-3.2 (6H, m), 2.78 (s) and 2.87 (s)(3H), 3.6-3.9 (1H, m), 4.1-5.1 (4H, m), 4.96 (2H, s), 6.9-7.3 (18H, m), 7.3-7.6 (1H, m), 7.6-7.8 (1H, m), 8.16 (4H, br s), 8.6-9.0 (2H, m), 9.3 (1H, broad).

(3)

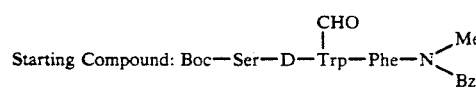

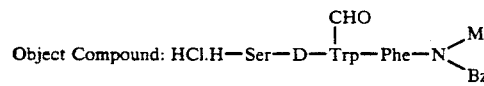

NMR (DMSO-d$_6$, δ): 2.6-3.1 (4H, m), 2.80 (s) and 2.89 (s)(3H), 3.1-3.9 (3H, m), 4.2-5.1 (4H, m), 5.3 (1H, broad), 6.9-7.7 (14H, m), 8.08 (4H, br s), 8.65 (1H, br d, J=9Hz), 8.90 (1H, br t, J=8Hz), 9.3 (1H, broad).

(4)

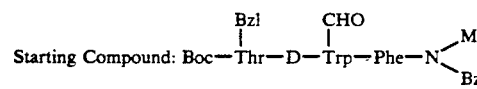

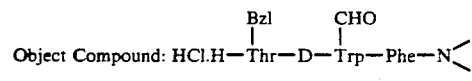

NMR (DMSO-d$_6$, δ): 0.84 (3H, d, J=6Hz), 2.5-3.1 (4H, m), 2.80 (s) and 2.88 (s)(3H), 3.4-5.1 (8H, m), 6.8-7.4 (17H, m), 7.60 (1H, br s), 7.65-7.85 (1H, m), 7.85-8.3 (4H, m), 8.93 (2H, m), 9.2 (1H, broad).

EXAMPLE 32

The following object compounds were obtained from the corresponding starting compounds according to a similar manner to that of Example 17.

(1)

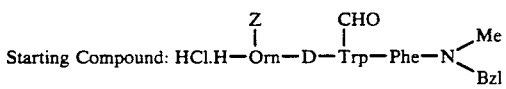

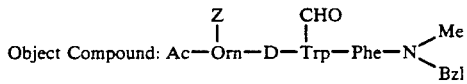

mp: ~212° C. (dec.).

IR (Nujol): 3300, 1710, 1700, 1640, 1540 (broad) cm$^{-1}$.

NMR (DMSO-d$_6$, δ): 0.9-1.5 (4H, m), 1.77 (3H, s), 2.6-3.2 (6H, m), 2.77 (s) and 2.86 (s)(3H), 4.0-5.1 (5H, m), 4.97 (2H, s), 6.9-7.6 (19H, m), 7.6-8.0 (2H, m), 8.0-8.3 (2H, m), 8.65 (1H, br t, J=9Hz), 9.2 (1H, broad).

Elemental Analysis. Calculated for C$_{44}$H$_{48}$N$_6$O$_7$.1/2-H$_2$O: C 67.59, H 6.32, N 10.75; Found: C 67.73, H 6.63, N 10.65.

(2)

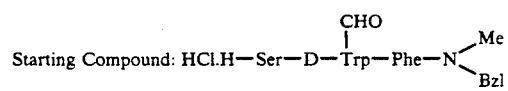

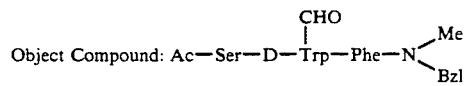

mp: ~125° C. (dec.).

IR (Nujol): 3300, 1710, 1640, 1530 (broad) cm$^{-1}$.

NMR (DMSO-d$_6$, δ): 1.82 (3H, s), 2.5-3.1 (4H, m), 2.77 (s) and 2.85 (s)(3H), 3.40 (2H, t, J=6Hz), 4.0-5.1 (6H, m), 6.9-7.7 (14H, m), 7.80 (1H, d, J=8Hz), 7.9-8.2 (2H, m), 8.62 (1H, t, J=8Hz), 9.2 (1H, broad).

EXAMPLE 33

The following object compounds were obtained from the corresponding starting compounds according to a similar manner to that of Example 29.

(1)

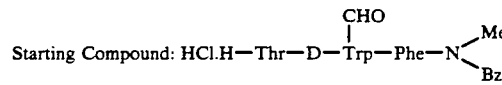

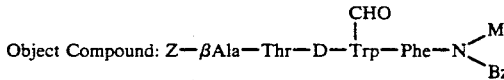

mp: ~177° C. (dec.).

IR (Nujol): 3300, 1710, 1690, 1640, 1535 cm$^{-1}$.

NMR (DMSO-d$_6$, δ): 0.75 (3H, d, J=6Hz), 2.36 (2H, t, J=7Hz), 2.5-3.3 (6H, m), 2.77 (s) and 2.84 (s) (s), 3.5-3.9 (1H, m), 3.9-4.2 (1H, m), 4.2-5.0 (5H, m), 4.96 (2H, s), 6.8-7.5 (18H, m), 7.5-7.8 (2H, m), 7.8-8.2 (2H, m), 8.61 (1H, t, J=9Hz), 9.2 (1H, broad).

Elemental Analysis. Calculated for C₄₄H₄₈N₆O₈: C 66.99, H 6.13, N 10.65; Found: C 66.90, H 6.14, N 10.74.

(2)

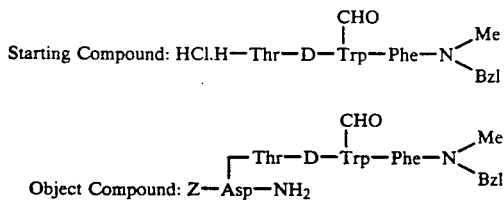

mp: 215°-217° C.

IR (Nujol): 3300, 1705, 1695, 1650 (broad), 1550 cm⁻¹.

NMR (DMSO-d₆, δ): 0.80 (3H, t, J=6Hz), 2.5-3.2 (6H, m), 2.75 (s) and 2.84 (s)(3H), 3.6-4.0 (1H, m), 4.0-4.5 (3H, m), 4.5-5.0 (4H, m), 4.97 (2H, s), 6.9-7.6 (21H, m), 7.6-7.9 (2H, m), 7.9-8.4 (2H, m), 8.66 (1H, br t, J=9Hz), 9.2 (1H, br s).

Elemental Analysis. Calculated for C₄₅H₄₉N₇O₉·H₂O: C 63.59, H 6.05, N 11.53; Found: C 63.54, H 6.02, N 11.48.

(3)

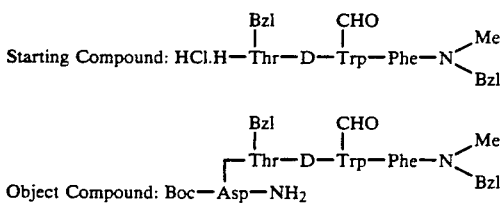

mp: ~195° C. (dec.).

IR (Nujol): 3200, 1710, 1690, 1660, 1640 cm⁻¹.

NMR (DMSO-d₆, δ): 0.90 (3H, d, J=6Hz), 1.33 (9H, s), 2.5-3.2 (7H, m), 2.77 (s) and 2.86 (s)(3H), 3.6-3.9 (1H, m), 3.9-4.85 (6H, m), 4.85-5.2 (1H, m), 6.75 (1H, br d, J=7Hz), 6.9-7.6 (20H, m), 7.6-7.9 (2H, m), 7.9-8.2 (2H, m), 8.80 (1H, br t, J=9Hz), 9.2 (1H, broad).

Elemental Analysis. Calculated for C₄₉H₅₇N₇O₉·3/2-H₂O: C 64.32, H 6.61, N 10.71; Found: C 64.04, H 6.41, N 10.65.

EXAMPLE 34

The following object compound was obtained from the corresponding starting compound according to a similar manner to that of Example 28.

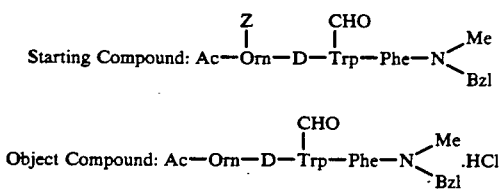

mp: ~214° C.

IR (Nujol): 3300 (broad), 1710-1630 (broad) cm⁻¹.

NMR (DMSO-d₆, δ): 1.1-2.0 (4H, m), 1.80 (3H, s), 2.5-3.2 (6H, m), 2.77 (s) and 2.86 (s)(3H), 4.1-5.1 (5H, m), 6.9-7.5 (14H, m), 7.5-8.4 (6H, m), 8.70 (1H, br t, J=8Hz), 9.3 (1H, broad).

EXAMPLE 35

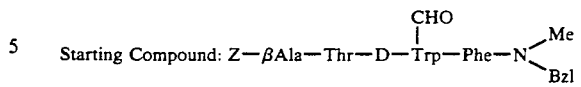

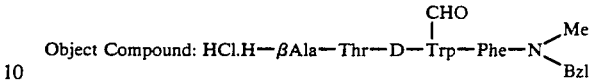

Z-βAla-Thr-D-Trp(CHO)-Phe-NMeBzl (0.32 g) was hydrogenated with 10% palladium on carbon (0.10 g) in AcOH (10 ml). The catalyst was filtered off and the filtrate was concentrated under reduced pressure. To the residue was added 4N-HCl/DOX (0.4 ml) and evaporated. The residue was pulverized with diethyl ether, filtered, washed with diethyl ether, and dried to give HCl.H-βAla-Thr-D-Trp(CHO)-Phe-NMeBzl (0.26 g).

mp: ~155° C. (dec.).

IR (Nujol): 3300 (broad), 1640 (broad) cm⁻¹.

NMR (DMSO-d₆, δ): 0.82 (3H, d, J=6Hz), 2.5-3.1 (8H, m), 2.78 (s) and 2.85 (s)(3H), 3.1-5.1 (10H, m), 6.8-7.3 (11H, m), 7.3-7.7 (2H, m), 7.7-8.2 (4H, m), 8.3-8.6 (1H, m), 9.2 (1H, broad).

EXAMPLE 36

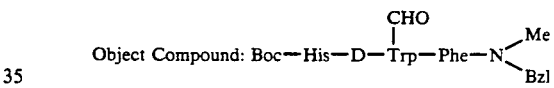

A solution of Boc-His(Tos)-OH (0.82 g) in DMF (10 ml) was cooled at −15° C. To the solution, NMM (0.22 ml) and isobutyl chloroformate (0.26 ml) were added successively and the mixture was stirred for ten minutes. On the other and, a solution of HCl.H-D-Trp(CHO)-Phe-NMeBzl in DMF (10 ml) was cooled at −15° C. and thereto was added NMM (0.22 ml). This solution was added to the above mentioned mixture and stirred for an hour at −15° C. After evaporation and extraction with ethyl acetate, the organic layer was washed successively with 2% hydrochloric acid, water, 2% sodium hydrogencarbonate, water and saturated sodium chloride solution, and dried over magnesium sulfate to give Boc-His(Tos)-D-Trp(CHO)-Phe-NMeBzl. After evaporation, the residue was dissolved in DMF (20 ml). To the solution, pyridinium chloride (2.18 g) was added under stirring at room temperature. After an hour, additional pyridinium chloride (0.5 g) was added and stirred for additional fifty minutes. After evaporation and extraction with ethyl acetate, the organic layer was washed successively with water, 2% hydrochloric acid, water, 2% sodium hydrogencarbonate, water, saturated sodium chloride solution and dried over magnesium sulfate. After evaporation, the residue was subjected to column chromatography on silica gel (60 g) and eluted with a mixture of chloroform and methanol (20:1). The fractions containing the object compound were combined and evaporated. The residue was pulverized with a mixture of ethanol, diethyl ether and n-hexane. The powder was filtered, washed with n-hexane and dried to give Boc-His-D-Trp(CHO)-Phe-NMeBzl (1.04 g).

mp: ~133° C. (dec.).

IR (Nujol): 3300, 1710, 1640 cm⁻¹.

NMR (DMSO-d₆, δ): 1.31 (9H, s), 2.5-3.1 (6H, m), 2.76 (s) and 2.84 (s)(3H), 3.9-5.1 (5H, m), 6.5-6.9 (1H, m), 6.56 (1H, s), 6.9-7.7 (14H, m), 7.45 (1H, s), 7.7-8.3 (2H, m), 8.6-8.8 (1H, m), 9.2 (1H, broad), 11.6 (1H, br s).

EXAMPLE 37

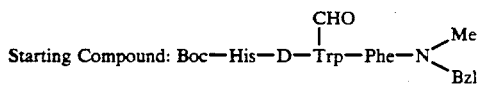

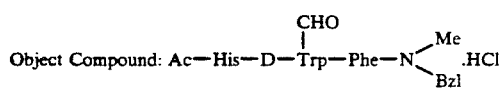

To an ice-cooled solution of Boc-His-D-Trp(CHO)-Phe-NMeBzl (0.70 g) and anisole (0.7 ml) in methylene chloride (5 ml) was added 4N-HCl/DOX (5 ml). The solution was stirred for an hour at room temperature. After evaporation, the residue was pulverized with diisopropyl ether, filtered, washed with diisopropyl ether and dried to give 2HCl.H-His-D-Trp(CHO)-Phe-NMeBzl. The powder (0.70 g) was dissolved in a mixture of methylene chloride (10 ml) and DMF (1 ml) and ice-cooled. To the solution, triethylamine (0.41 ml) and Ac₂O (0.09 ml) were added. After stirring for an hour and twenty minutes, triethylamine (0.12 ml) and Ac₂O (0.09 ml) were added and stirred for additional half an hour. The mixture was evaporated and the residue was extracted with ethyl acetate. The organic layer was washed successively with water, 2% hydrochloric acid, water and saturated sodium chloride solution, and dried over magnesium sulfate. After evaporation, the residue was dissolved in DMF (10 ml). To the solution, pyridinium chloride (1.16 g) was added and the mixture was stirred for an hour. After evaporation the residue was solidified with water, filtered, washed with water, and dried. The powder was subjected to column chromatography on silica gel (20 g) and eluted with a mixture of chloroform and methanol (9:1). The fractions containing the object compound were combined and evaporated. The residue was pulverized with diethyl ether and filtered. The powder was dissolved in a mixture of chloroform and methanol. To the solution was added 4N-HCl/DOX (0.25 ml) and evaporated. The residue was pulverized with diethyl ether, filtered, washed with diethyl ether and dried to give Ac-His-D-Trp(CHO)-Phe-NMeBzl.HCl (0.31 g).

mp: ~150° C. (dec.).

IR (Nujol): 3270 (broad), 1710-1630 (broad) cm⁻¹.

NMR (DMSOd-6, δ): 1.77 (3H, s), 2.5-3.1 (6H, m), 2.78 (s) and 2.85 (s)(3H), 4.2-5.1 (5H, m), 6.9-7.4 (13H, m), 7.4-7.5 (1H, m), 7.5-7.8 (1H, m), 7.8-8.3 (3H, m), 8.5-8.9 (1H, m), 8.89 (1H, s), 9.3 (1H, broad), 14.4 (2H, broad).

EXAMPLE 38

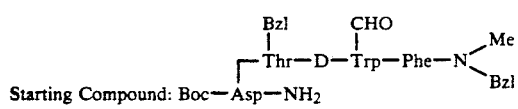

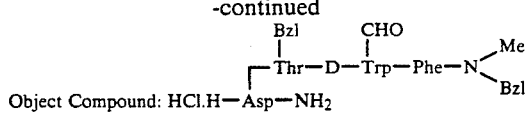

To a mixture of Boc-β-Asp(α-NH₂)-Thr(Bzl)-D-Trp(CHO)-Phe-NMeBzl (0.92 g) and anisole (1 ml) was added 4N-HCl/Dox (10 ml) at 5° C. The mixture was stirred for ten minutes under ice-cooling, and for an hour at room temperature. After evaporation, the residue was pulverized with diisopropyl ether, filtered, washed with diisopropyl ether and dried to give HCl.H-β-Asp(α-NH₂)-Thr(Bzl)-D-Trp(CHO)-Phe-NMeBzl (0.81 g).

IR (Nujol): 3300 (broad), 1690, 1640 (broad) cm⁻¹.

NMR (DMSOd-6, δ): 0.85 (3H, d, J=6Hz), 2.5-3.1 (6H, m), 2.77 (s) and 2.85 (s)(3H), 3.5-5.2 (9H, m), 6.9-7.4 (17H, m), 7.4-7.6 (2H, m), 7.6-7.9 (2H, m), 7.9-8.4 (6H, m), 8.79 (1H, br t, J=8Hz), 9.2 (1H, broad).

EXAMPLE 39

The following object compound was obtained from the corresponding starting compound according to a similar manner to that of Example 3.

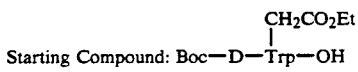

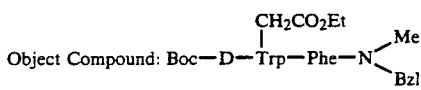

mp: 91°-104° C.

IR (Nujol): 3300, 3250, 1760, 1740, 1705, 1670, 1620 cm⁻¹.

NMR (CDCl₃, δ): 0.95 and 1.00 (3H, t, J=7Hz), 1.40 (9H, s), 2.54 and 2.73 (3H, s), 2.6-2.8 (2H, m), 3.23 (2H, d, J=5Hz), 4.16 (2H, q, J=7Hz), 4.23 and 4.53 (2H, ABq, J=15Hz), 4.5 (1H, m), 4.70 (2H, s), 4.9-5.2 (2H, m), 6.5-6.7 (1H, m), 6.8-7.3 (14H, m), 7.5-7.7 (1H, m).

Elemental Analysis. Calculated for C₃₇H₄₄N₄O₆: C 69.35, H 6.92, N 8.74; Found: C 69.14, H 6.98, N 8.73.

EXAMPLE 40

The following object compound was obtained from the corresponding starting compound according to a similar manner to that of Example 4.

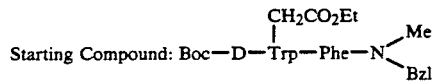

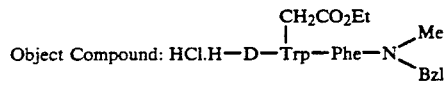

EXAMPLE 41

The following object compound was obtained from the corresponding starting compound according to a similar manner to that of Example 13.

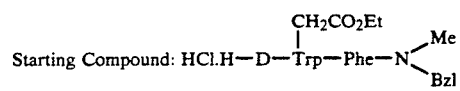

-continued

Object Compound: 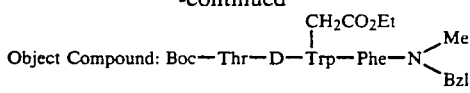

NMR (CDCl₃, δ): 1.04 (3H, d, J=6Hz), 1.23 (3H, t, J=7Hz), 1.36 (9H, s), 2.61 and 2.73 (3H, s), 2.85 (2H, d, J=6Hz), 3.23 (2H, d, J=6Hz), 4.08 (2H, q, J=7Hz), 3.8–4.5 (5H, m), 4.71 (2H, s), 4.7 (1H, m), 4.95 (1H, m), 5.41 (1H, d, J=6Hz), 6.7–7.3 (16H, m), 7.4–7.6 (1H, m).

EXAMPLE 42

The following object compound was obtained from the corresponding starting compound according to a similar manner to that of Example 15.

Starting Compound: 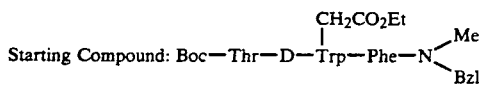

Object Compound: 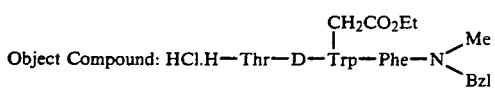

EXAMPLE 43

The following object compound was obtained from the corresponding starting compound according to a similar manner to that of Example 17.

Starting Compound: 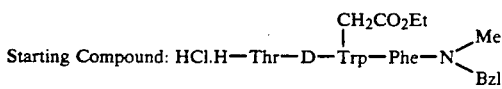

Object Compound: 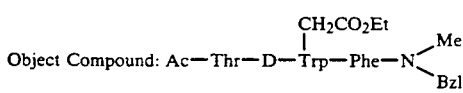

NMR (DMSOd-₆, δ): 0.85 (3H, d, J=6Hz), 1.18 (3H, t, J=6Hz), 1.87 (3H, s), 2.74 and 2.81 (3H, s), 2.7–3.1 (4H, m), 3.27 (1H, m), 3.8 (1H, m), 4.1 (1H, m), 4.10 (2H, q, J=6Hz), 4.3–5.1 (4H, m), 4.92 (2H, s), 6.9–7.35 (9H, m), 7.20 (5H, s), 7.5–7.9 (3H, m), 8.5 (1H, m).

EXAMPLE 44

Starting Compound: 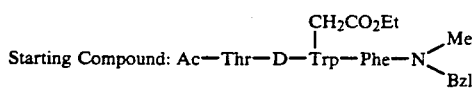

Object Compound: 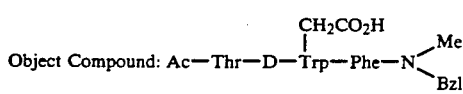

To a solution of Ac-Thr-D-Trp(CH₂CO₂Et)-Phe-NMeBzl (0.98 g) in ethanol (25 ml) was added 0.1N sodium hydroxide solution (14.3 ml) under ice-cooling. After stirring two hours, 0.1N sodium hydroxide solution (2.0 ml) was added and the mixture was stirred for additional two hours. The ethanol was evaporated and the solution was extracted twice with ethyl acetate. The aqueous layer was acidified with 1N hydrochloric acid and extracted twice with ethyl acetate. The extract was washed with sodium chloride solution and concentrated to give Ac-Thr-D-Trp(CH₂CO₂H)-Phe-NMeBzl as an amorphous solid (0.90 g).

IR (Nujol): 3300, 1730, 1660 (sh), 1645, 1630 cm⁻¹.

NMR (DMSOd-₆, δ): 0.84 (3H, d, J=6Hz), 1.86 (3H, s), 2.7–3.0 (7H, m), 3.3 (1H, m), 3.8 (1H, m), 4.05–4.2 (2H, m), 4.35–5.0 (3H, m), 4.82 (2H, s), 6.9–7.3 (9H, m), 7.20 (5H, s), 7.45–7.9 (3H, m), 8.4–8.6 (1H, m), 12.7 (1H, br s).

EXAMPLE 45

Starting Compound: 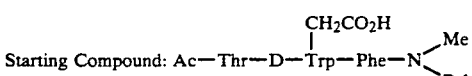

Object Compound: 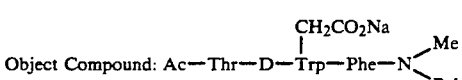

Ac-Thr-D-Trp(CH₂CO₂H)-Phe-NMeBzl (0.509 g) was dissolved in a mixed solvent of acetone (8 ml) and THF (6 ml) and the insoluble material was filtered off. To the solution was added sodium 2-ethyl hexanoate (129 mg) at room temperature. The solution was concentrated to one-third volume and ether (10 ml) was added thereto. After stirring for an hour, the precipitates were collected, washed with ether and dried under vacuum to give Ac-Thr-D-Trp(CH₂CO₂Na)-Phe-NMeBzl (0.55 g) as an amorphous solid.

IR (Nujol): 3300, 1660 (sh), 1640, 1540 cm⁻¹.

NMR (DMSOd-₆, δ): 1.03 (3H, d, J=6Hz), 1.93 (3H, s), 2.46 and 2.64 (3H, s), 2.5–2.6 (2H, m), 3.15 (2H, m), 3.8–4.4 (6H, m), 4.60 (2H, s), 6.7–7.4 (15H, m).

EXAMPLE 46

The following object compounds were obtained from the corresponding starting compounds according to a similar manner to that of Example 1.

(1)

Starting Compound: 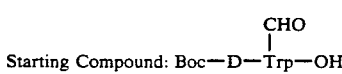

Object Compound: 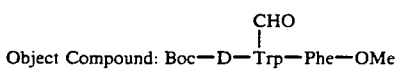

mp: 114°–116° C.

IR (Nujol): 3320, 1740, 1710, 1700, 1680, 1660, 1545, 1525 cm⁻¹.

NMR (DMSOd-₆, δ): 1.28 (9H, m), 2.6–3.3 (4H, m), 3.65 (3H, s), 4.1–4.8 (2H, m), 6.83 (1H, br d, J=9Hz), 7.2–7.6 (3H, m), 7.24 (5H, s), 7.6–7.9 (1H, m), 8.0–8.4 (1H, m), 8.54 (1H, br d, J=9Hz), 9.4 (1H, broad).

Elemental Analysis. Calculated for C₂₇H₃₁N₃O₆: C 65.71, H 6.33, N 8.51; Found: C 65.82, H 6.19, N 8.45.

(2)

Starting Compound: 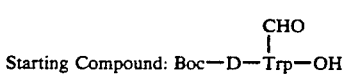

Object Compound: 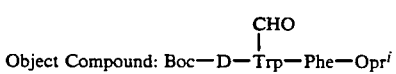

mp: 100°–103° C.

IR (Nujol): 3340, 1725, 1710, 1690, 1650, 1530 cm⁻¹.

NMR (DMSOd-₆, δ): 1.12 (6H, d, J=6Hz), 1.27 (9H, s), 2.6–3.2 (4H, m), 4.1–4.7 (2H, m), 4.91 (1H, sep), 6.87 (1H, br d, J=9Hz), 7.2–7.6 (3H, m), 7.25 (5H, s), 7.6–7.9

(1H, m), 8.0–8.3 (1H, m), 8.53 (1H, br d, J=9Hz), 9.4 (1H, broad).

Elemental Analysis. Calculated for $C_{29}H_{35}N_3O_6$: C 66.78, H 6.76, N 8.06; Found: C 66.62, H 6.47, N 8.14.

(3)

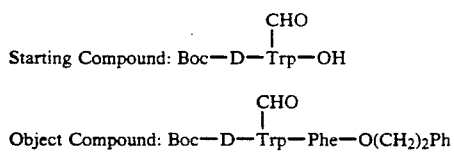

mp: 141°–142° C.
IR (Nujol): 3400, 1740, 1720, 1680, 1670, 1525, 1510 cm$^{-1}$.
NMR (DMSOd-$_6$, δ): 1.26 (9H, s), 2.6–3.1 (4H, m), 2.88 (2H, t, J=6Hz), 4.2–4.8 (2H, m), 4.28 (2H, t, J=6Hz), 6.83 (1H, br d, J=9Hz), 7.1–7.6 (3H, m), 7.20 (5H, s), 7.28 (5H, s), 7.6–7.9 (1H, m), 7.9–8.3 (1H, m), 8.53 (1H, br d, J=9Hz), 9.4 (1H, broad).
Elemental Analysis. Calculated for $C_{34}H_{37}N_3O_6$: C 69.97, H 6.39, N 7.20; Found: C 69.78, H 6.47, N 7.26.

(4)

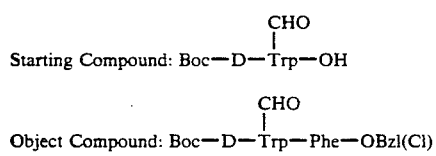

mp: 157°–158° C.
IR (Nujol): 3350, 1740, 1720, 1680, 1660, 1545, 1515 cm$^{-1}$.
NMR (DMSO-d$_6$, δ): 1.29 (9H, s), 2.6–3.3 (4H, m), 4.1–4.8 (2H, m), 5.14 (2H, s), 6.93 (1H, br d, J=9Hz), 7.2–7.9 (4H, m), 7.26 (5H, s), 7.43 (4H, s), 8.2 (1H, br s), 8.58 (1H, br d, J=8Hz), 9.4 (1H, broad).
Elemental Analysis. Calculated for $C_{33}H_{34}ClN_3O_6$: C 65.61, H 5.67, N 6.96; Found: C 65.48, H 5.56, N 7.04.

(5)

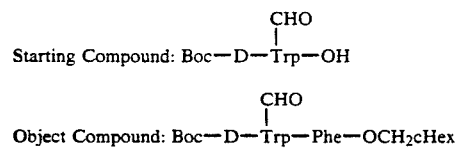

mp: 78°–80° C.
IR (Nujol): 3350, 1710, 1690, 1650, 1525 cm$^{-1}$.
NMR (DMSOd-$_6$, δ): 0.7–1.8 (10H, m), 1.28 (9H, s), 2.6–3.2 (5H, m), 3.87 (2H, d, J=6Hz), 4.0–4.8 (2H, m), 6.6–6.9 (1H, m), 7.1–7.8 (4H, m), 7.26 (5H, s), 7.9–8.3 (1H, m), 8.53 (1H, br d, J=9Hz), 9.4 (1H, broad).
Elemental Analysis. Calculated for $C_{33}H_{41}N_3O_6$: C 68.85, H 7.18, N 7.30; Found: C 68.94, H 7.18, N 7.30.

(6)

Starting Compound: Z-D-Trp-OH

Object Compound: Z-D-Trp-Phe-OBzl mp: 108°–111° C.
IR (Nujol): 3450, 3300, 1750, 1700, 1655, 1530 cm$^{-1}$.
NMR (DMSOd-$_6$, δ): 2.6–3.2 (4H, m), 4.1–4.8 (2H, m), 4.94 (2H s) 5.13 (2H s) 6.8–7.8 (21H, m), 8.4–8.7 (1H, m), 10.73 (1H, br s).
Elemental Analysis. Calculated for $C_{35}H_{33}N_3O_5$: C 73.03, H 5.7, N 7.30; Found: C 72.88, H 5.83, N 7.29.

EXAMPLE 47

The following object compounds were obtained from the corresponding starting compounds according to a similar manner to that of Example 2.

(1)

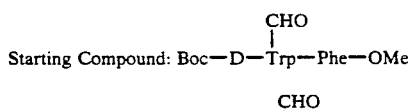

IR (Nujol): 1740, 1710, 1690 cm$^{-1}$.
NMR (DMSOd-$_6$, δ): 2.7–3.3 (4H, m), 3.65 (3H, s), 4.0–4.3 (1H, m), 4.4–4.8 (1H, m), 7.24 (5H, s), 7.3–7.5 (2H, m), 7.6–7.9 (2H, m), 8.1–8.5 (1H, m), 8.38 (3H, br s), 9.47 (1H, d, J=8Hz), 9.5 (1H, broad).

(2)

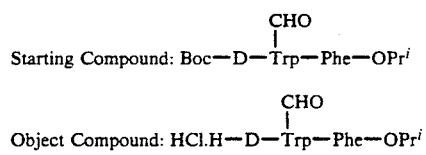

IR (Nujol): 3350, 1700, 1690 cm$^{-1}$.
NMR (DMSOd-$_6$, δ): 1.09 (3H, d, J=7Hz), 1.18 (3H, d, J=7Hz), 2.8–3.3 (4H, m), 3.9–4.3 (1H, m), 4.3–4.7 (1H, m), 4.88 (1H, sep, J=7Hz), 7.27 (5H, s), 7.3–7.5 (2H, m), 7.5–7.9 (2H, m), 8.2 (1H, broad), 8.4 (3H, br s), 9.37 (1H, d, J=8Hz), 9.4 (1H, broad).

(3)

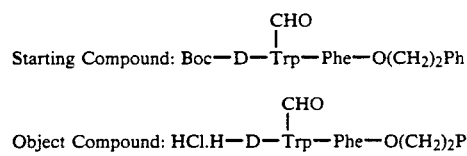

IR (Nujol): 1710, 1690 cm$^{-1}$.
NMR (DMSOd-$_6$, δ): 2.6–3.2 (4H, m), 2.87 (2H, t, J=7Hz), 3.9–4.7 (2H, m), 4.27 (2H, t, J=7Hz), 7.1–7.5 (2H, m), 7.19 (5H, s), 7.30 (5H, s), 7.6–7.9 (2H, m), 8.0–8.4 (1H, m), 8.35 (3H, br s), 9.4 (1H, broad), 9.41 (1H, d, J=7Hz).

(4)

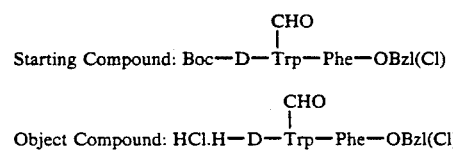

IR (Nujol): 1710, 1690, 1600 cm$^{-1}$.
NMR (DMSOd-$_6$, δ): 2.7–3.4 (4H, m), 4.0–4.3 (1H, m), 4.4–4.8 (1H, m), 5.14 (2H, s), 7.2–7.6 (6H, m), 7.26

(5H, s), 7.6–7.9 (2H, m), 8.2 (1H, broad), 8.42 (3H, br s), 9.4 (1H, broad), 9.54 (1H, br d, J=8Hz).

(5)

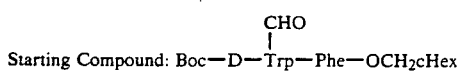

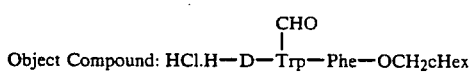

NMR (DMSO-d₆, δ) 0.6–1.8 (10H, m), 2.6–3.3 (5H, m), 3.85(2H, d, J=6Hz), 4.13 (1H, br t, J=6Hz), 4.57 (1H, br q, J=7Hz), 7.1–7.5 (2H, m), 7.25 (5H, s), 7.6–7.8 (2H, m), 8.2 (1H, br s), 8.4 (3H, br s), 9.4 (1H, broad), 9.43 (1H, d, J=8Hz).

(6)

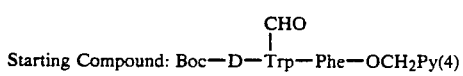

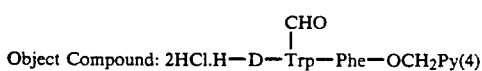

NMR (DMSOd-₆, δ): 2.7–3.4 (4H, m), 4.0–4.4 (1H, m), 4.5–4.9 (1H, m), 5.43 (2H, s), 7.1–7.5 (3H, m), 7.30 (5H, s), 7.5–7.9 (2H, m), 7.96 (2H, d, J=6Hz), 8.0–8.3 (1H, m), 8.5 (3H, br s), 8.92 (2H, d, J=6Hz), 9.45 (1H, broad), 9.82 (1H, br d, J=8Hz).

(7)

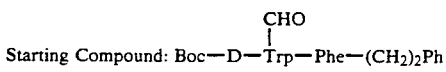

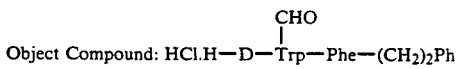

NMR (DMSOd-₆, δ): 2.6–3.3 (8H, m), 3.9–4.3 (1H, m), 4.4–4.8 (1H, m), 7.0–7.5 (2H, m), 7.20 (10H, s), 7.5–7.8 (2H, m), 8.2 (1H, br s), 8.3 (3H, br s), 9.4 (1H, broad), 9.49 (1H, d, J=8Hz).

EXAMPLE 48

The following object compounds were obtained from the corresponding starting compounds according to a similar manner to that of Example 11.

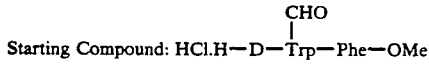

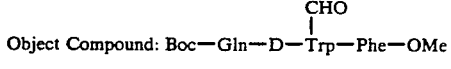

mp: 165°–167° C.

IR (Nujol): 3310, 1710, 1690, 1650 (broad), 1540, 1525 cm⁻¹.

NMR (DMSOd-₆, δ): 1.33 (9H, s), 1.4–2.1 (4H, m), 2.6–3.1 (4H, m), 3.63 (3H, s), 3.7–4.1 (1H, m), 4.3–4.8 (2H, m), 6.6–6.9 (2H, m), 7.0–7.5 (4H, m), 7.25 (5H, s), 7.5–7.7 (1H, m), 7.9–8.3 (2H, m), 8.64 (1H, br d, J=8Hz), 9.3 (1H, broad).

Elemental Analysis. Calculated for C₃₂H₃₉N₅O₈.2/3-H₂O: C 60.65, H 6.41, N 11.05; Found: C 60.59, H 6.06, N 10.97.

(2)

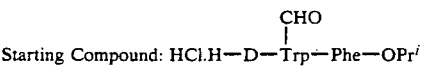

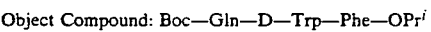

mp: 213°–216° C.

IR (Nujol): 3450, 3350, 1715, 1690, 1660, 1645, 1545, 1530 cm⁻¹.

NMR (DMSO-d₆, δ): 1.07 (3H, d, J=7Hz), 1.17 (3H, d, J=7Hz), 1.32 (9H, s), 1.5–2.2 (4H, m), 2.6–3.2 (4H, m), 3.8–4.1 (1H, m), 4.3–4.9 (2H, m), 4.88 (1H, sep, J=7Hz), 6.6–7.0 (2H, m), 7.0–7.6 (4H, m), 7.23 (5H, s), 7.6–7.8 (1H, m), 7.9–8.3 (2H, m), 8.70 (1H, br d, J=8Hz), 9.3 (1H, broad).

Elemental Analysis. Calculated for C₃₄H₄₃N₅O₈: C 62.85, H 6.67, N 10.78; Found: C 63.11, H 7.00, N 10.54.

(3)

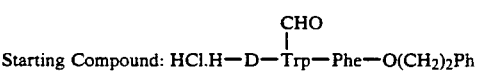

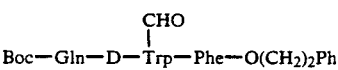

mp: 157°–159° C.

IR (Nujol): 3330, 1725, 1710, 1690, 1645, 1530 cm⁻¹.

NMR (DMSOd-₆, δ): 1.33 (9H, s), 1.5–2.2 (4H, m), 2.6–3.1 (6H, m), 3.7–4.2 (1H, m), 4.27 (2H, t, J=6Hz), 4.4–4.9 (2H, m), 6.6–6.9 (2H, m), 7.0–7.8 (5H, m), 7.22 (5H, s), 7.28 (5H, s), 7.9–8.3 (2H, m), 8.61 (1H, br d, J=8Hz), 9.3 (1H, broad).

Elemental Analysis. Calculated for C₃₉H₄₅N₅O₈: C 65.81, H 6.37, N 9.84; Found: C 65.76, H 6.75, N 9.73.

(4)

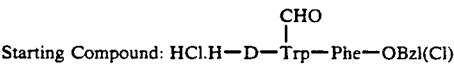

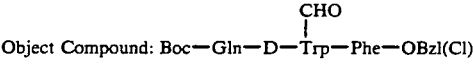

mp: 214°–216° C.

IR (Nujol): 3310, 1725, 1710, 1685, 1640, 1545, 1530 cm⁻¹.

NMR (DMSOd-₆, δ): 1.32 (9H, s), 1.4–2.2 (4H, m), 2.6–3.2 (4H, m), 3.8–4.1 (1H, m), 4.4–4.9 (2H, m), 5.11 (2H, s), 6.6–6.9 (2H, m), 7.0–7.7 (9H, m), 7.23 (5H, s), 7.9–8.4 (2H, m), 8.73 (1H, br d, J=9Hz), 9.3 (1H, broad).

Elemental Analysis. Calculated for C₃₈H₄₂ClN₅O₈: C 62.33, H 5.78, N 9.56; Found: C 62.28, H 5.75, N 9.57.

(5)

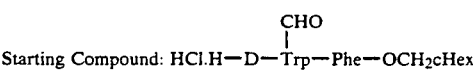

-continued

Object Compound:

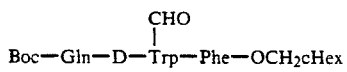
Boc—Gln—D—Trp(CHO)—Phe—OCH₂cHex mp: 199°–201° C.
IR (Nujol): 3340, 1710, 1690, 1655, 1645, 1545, 1530 cm⁻¹.
NMR (DMSOd-6, δ): 0.6–2.1 (14H, m), 1.33 (9H, s), 2.7–3.3 (5H, m), 3.7–4.1 (1H, m), 3.84 (2H, d, J=6Hz), 4.3–4.9 (2H, m), 6.6–6.9 (2H, m), 7.0–7.8 (5H, m), 7.25 (5H, s), 7.9–8.4 (2H, m), 8.5–8.8 (1H, m), 9.3 (1H, broad).
Elemental Analysis. Calculated for C₃₈H₄₉N₅O₈.1/2-H₂O: C 64.03, H 7.07, N 9.82; Found: C 64.10, H 6.96, N 9.75.

(6)

Starting Compound: 2HCl.H—D—Trp(CHO)—Phe—OCH₂Py(4)

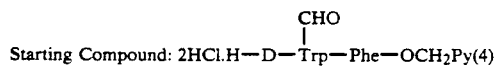

Object Compound: Boc—Gln—D—Trp(CHO)—Phe—OCH₂Py(4)

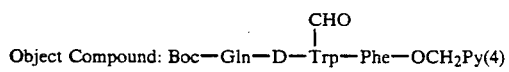

mp: ~169° C. (dec.).
IR (Nujol): 3330, 1710, 1690, 1660, 1640, 1525 cm⁻¹.
NMR (DMSOd-6, δ): 1.30 (9H, s), 1.4–2.2 (4H, m), 2.6–3.2 (4H, m), 3.7–4.1 (1H, m), 4.5–4.9 (2H, m), 5.16 (2H, s), 6.6–6.9 (2H, m), 7.0–7.7 (7H, m), 7.24 (5H, s), 7.9–8.3 (2H, m), 8.5–8.6 (2H, m), 8.72 (1H, br d, J=7Hz), 9.3 (1H, broad).
Elemental Analysis. Calculated for C₃₇H₄₂N₆O₈.1/2-H₂O: C 62.79, H 6.12, N 11.87; Found: C 62.88, H 5.96, N 11.87.

(7)

Starting Compound: HCl.H—D—Trp(CHO)—Phe—OBzl

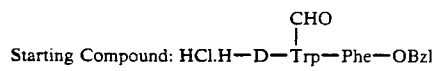

Object Compound: Boc—Gly—D—Trp(CHO)—Phe—OBzl

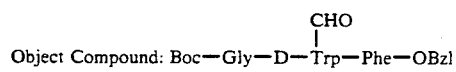

mp: 78°–80° C.
IR (Nujol): 3290, 1750, 1710, 1650, 1555 cm⁻¹.
NMR (DMSO-d6, δ): 1.33 (9H, s), 2.6–3.3 (4H, m), 3.49 (2H, d, J=6Hz), 4.4–4.9 (2H, m), 5.13 (2H, s), 6.9 (1H, br s), 7.2–7.8 (4H, m), 7.24 (5H, s), 7.37 (5H, s), 7.97 (1H, d, J=9Hz), 8.2 (1H, broad), 8.76 (1H, d, J=9Hz), 9.3 (1H, broad).
Elemental Analysis. Calculated for C₃₅H₃₈N₄O₇: C 67.08, H 6.11, N 8.94; Found: C 66.83, H 5.58, N 8.93.

(8)

Starting Compound: HCl.H—D—Trp(CHO)—Phe—OBzl

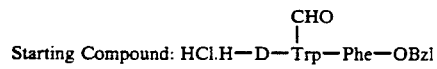

Object Compound: Boc—Tyr—D—Trp(CHO)—Phe—OBzl

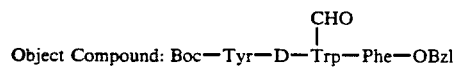

mp: 213°–215° C.
IR (Nujol): 3450, 3290, 1755, 1715, 1640, 1560 cm⁻¹.
NMR (DMSO-d6, δ): 1.25 (9H, s), 2.3–2.6 (2H, m), 2.6–3.2 (4H, m), 3.9–4.3 (1H, m), 4.4–5.0 (2H, m), 5.12 (2H, s), 6.4–6.7 (1H, m), 6.53 (2H, d, J=9Hz), 6.86 (2H, d, J=9Hz), 7.2–7.8 (4H, m), 7.26 (5H, s), 7.35(5H, s), 8.0–8.4 (2H, m), 8.6–8.9 (1H, m), 9.08 (1H, s), 9.3 (1H, broad).
Elemental Analysis. Calculated for C₄₂H₄₄N₄O₈: C 68.84, H 6.05, N 7.65; Found: C 68.62, H 6.09, N 7.67.

(9)

Starting Compound: HCl.H—D—Trp(CHO)—Phe—OBzl

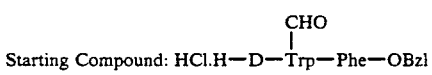

Object Compound:

H₂NCO(CH₂)₂CO—D—Trp(CHO)—Phe—OBzl

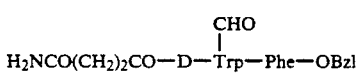

mp: 199°–200° C.
IR (Nujol): 3430, 3300, 1735, 1715, 1665, 1645, 1535 cm⁻¹.
NMR (DMSO-d6, δ): 2.24 (3H, s), 2.6–3.3 (4H, m), 4.5–4.8 (2H, m), 5.11 (2H, s), 6.74 (1H, br s), 7.1–7.8 (5H, m), 7.20 (5H, s), 7.35 (5H, s), 8.10 (2H, br d, J=9Hz), 8.65 (1H, d, J=8Hz), 9.35 (1H, broad).
Elemental Analysis. Calculated for C₃₂H₃₂N₄O₆: C 67.59, H 5.67, N 9.85; Found: C 67.45, H 5.62, N 9.96.

(10)

Starting Compound: HCl.H-D-Trp-Phe-OBzl

Object Compound: Boc-D-Trp-D-Trp-Phe-OBzl mp: 142°–144° C.
IR (Nujol): 3430, 3350, 1750, 1690, 1640, 1525 cm⁻¹.
NMR (DMSO-d6, δ): 1.23 (9H s) 2.6–3.1 (6H m), 3.9–4.25 (1H, m), 4.25–4.75 (2H, m), 5.03 (2H, s), 6.6–7.6 (11H, m), 7.14 (5H, s), 7.23 (5H, s), 7.73 (1H, br d, J=8Hz), 8.51 (1H, br d, J=8Hz), 10.64 (2H, s).
Elemental Analysis. Calculated for C₄₃H₄₅N₅O₆: C 70.96, H 6.23, N 9.62; Found: C 70.68, H 6.17, N 9.61.

EXAMPLE 49

Starting Compound: Boc—D—Trp(CHO)—OH

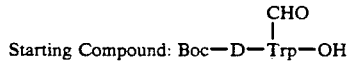

Object Compound: Boc—D—Trp(CHO)—Phe—OCH₂Py(4)

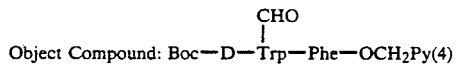

To a solution of Boc-D-Trp(CHO)-OH (1.00 g), 2HCl.H-Phe-OCH₂Py(4) (0.99 g) and HOBT (0.41 g) in DMF (25 ml) were added N,N-diisopropylethylamine (0.53 ml) and WSC (0.55 ml) under ice cooling. The mixture was stirred for an hour at this temperature and for additional 1.5 hours at room temperature. After evaporation and extraction with ethyl acetate the organic layer was washed successively with water, 2% sodium hydrogencarbonate solution, water and saturated sodium chloride solution, and dried over magnesium sulfate. The evaporated residue was subjected to column chromatography on silica gel (40 g) and eluted with a mixture of chloroform and methanol (20:1). The fractions containing the object compound were combined and evaporated. The residue was pulverized with n-hexane and filtered. The powder was dissolved in ethanol and reprecipitated with water, filtered and dried to give Boc-D-Trp(CHO)-Phe-OCH$_2$Py(4) (1.29 g).

mp: 113°–115° C.

IR (Nujol): 3350, 1740, 1710, 1680, 1655, 1525 cm$^{-1}$.

NMR (DMSO-d$_6$, δ): 1.28 (9H, s), 2.6–3.3 (4H, m), 4.1–4.5 (1H, m), 4.5–4.9 (1H, m), 5.20 (2H, s), 6.92 (1H, br d, J=9Hz), 7.1–7.9 (6H, m), 7.27 (5H, s), 7.9–8.4 (1H, m), 8.5–8.8 (3H, m), 9.4 (1H, broad).

Elemental Analysis. Calculated for C$_{32}$H$_{34}$N$_4$O$_6$: C 67.35, H 6.01, N 9.82; Found: C 67.02, H 5.98, N 9.78.

EXAMPLE 50

Starting Compound:

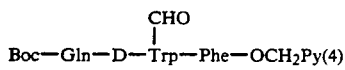

Object Compound:

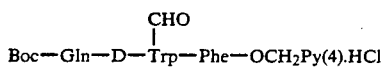

To a solution of Boc-Gln-D-Trp(CHO)-Phe-OCH$_2$Py(4) (0.27 g) in a mixture of THF (25 ml) and DMF (5 ml) was added 4N-HCl/DOX (0.1 ml). After evaporation, the residue was pulverized with diethyl ether. The powder was filtered, washed with diisopropyl ether and dried to give Boc-Gln-D-Trp(CHO)-Phe-OCH$_2$Py(4).HCl (0.24 g).

mp: ~160° C. (dec.).

IR (Nujol): 3300 (broad), 1750, 1710–1640, 1530–1500 cm$^{-1}$.

NMR (DMSO-d$_6$, δ): 1.31 (9H, s), 1.5–2.1 (4H, m), 2.7–3.2 (4H, m), 3.8–4.1 (1H, m), 4.6 (10H, broad, overlapped with HOD), 5.42 (2H, s), 6.7–7.0 (2H, m), 7.0–7.8 (6H, m), 7.28 (5H, s), 7.89 (2H, d, J=6Hz), 8.0–8.3 (2H, m), 8.89 (2H, d, J=6Hz), 9.3 (1H, broad).

EXAMPLE 51

The following object compounds were obtained from the corresponding starting compounds according to a similar manner to that of Example 8.

(1)

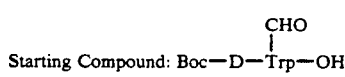

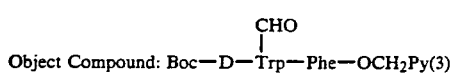

mp: 144°–145° C.

IR (Nujol): 3410, 1720, 1690, 1650, 1545, 1530 cm$^{-1}$.

NMR (DMSO-d$_6$, δ): 1.30 (9H, s), 2.5–3.2 (4H, m), 4.0–4.4 (1H, m), 4.4–4.8 (1H, m), 5.14 (2H, s), 6.80 (1H, br d, J=8Hz), 7.0–7.5 (4H, m), 7.18 (5H, s), 7.5–7.8 (2H, m), 8.1 (1H, broad), 8.4–8.7 (3H, m), 9.3 (1H, broad).

Elemental Analysis. Calculated for C$_{32}$H$_{34}$N$_4$O$_6$: C 67.35, H 6.01, N 9.82; Found: C 67.49, H 6.02, N 9.75.

(2)

-continued

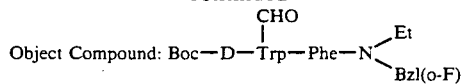

mp: 69°–79° C.

IR (Nujol): 3300, 1710, 1630 cm$^{-1}$.

NMR (DMSO-d$_6$, δ): 0.95 (t, J=6Hz) and 1.01 (t, J=6Hz)(3H), 1.25 (9H, s), 2.5–3.1 (4H, m), 3.1–3.6 (2H, m), 4.0–5.2 (4H, m), 6.7–6.9 (1H, m), 6.9–7.9 (13H, m), 8.1 (1H, br s), 8.60 (1H, br d, J=9Hz), 9.0–9.7 (1H, broad).

Elemental Analysis. Calculated for C$_{35}$H$_{39}$FN$_4$O$_5$.1/2H$_2$O: C 67.40, H 6.46, N 8.98; Found: C 67.28, H 6.56, N 8.74.

(3)

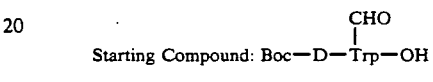

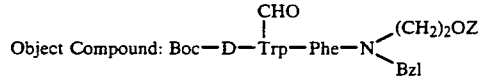

mp: ~70° C.

IR (Nujol): 3300, 1745, 1710, 1635 cm$^{-1}$.

NMR (DMSO-d$_6$, δ): 1.24 (9H, s), 2.5–3.1 (4H, m), 3.2–3.6 (2H, m), 3.9–5.1 (6H, m), 5.09 (s) and 5.12 (s)(2H), 6.6–6.9 (1H, m), 6.9–7.55 (13H, m), 7.33 (5H, s), 7.55–7.8 (1H, m), 7.9–8.2 (1H, m), 8.4–8.8 (1H, m), 9.3 (1H, broad).

Elemental Analysis. Calculated for C$_{43}$H$_{46}$N$_4$O$_8$: C 69.15, H 6.21, N 7.50; Found: C 68.91, H 6.07, N 7.37.

EXAMPLE 52

The following object compounds were obtained from the corresponding starting compounds according to similar manner to those of Example 4 and Example 13, successively.

(1)

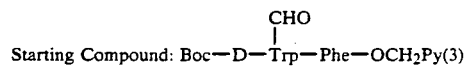

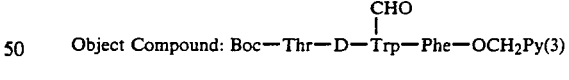

mp: 143°–145° C.

IR (Nujol): 3330, 1735, 1715, 1690, 1645, 1550, 1530 cm$^{-1}$.

NMR (DMSO-d$_6$, δ): 0.84 (3H, d, J=6Hz), 1.34 (9H, s), 2.6–3.2 (4H, m), 3.6–4.0 (2H, m), 4.3–4.8 (3H, m), 5.11 (2H, s), 6.31 (1H, br d, J=7Hz), 7.0–7.7 (6H, m), 7.17 (5H, s), 7.8–8.3 (2H, m), 8.4–8.7 (3H, m), 8.9–9.6 (1H, broad).

Elemental Analysis. Calculated for C$_{36}$H$_{41}$N$_5$O$_8$: C 64.37, N 6.15, H 10.43; Found: C 64.15, N 6.01, H 10.37.

(2)

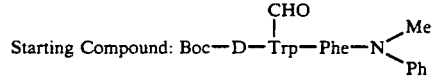

-continued

Object Compound: 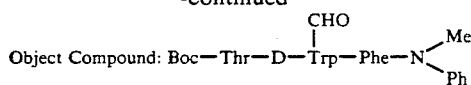

mp: 130°–133° C.

IR (Nujol): 3330, 1710, 1690, 1650, 1630, 1590 cm$^{-1}$.

NMR (DMSO-d$_6$, δ): 0.81 (3H, d, J=6Hz), 1.34 (9H, s), 2.5–3.1 (4H, m), 3.12 (3H, s), 3.6–4.0 (2H, m), 4.3–4.8 (3H, m), 6.22 (1H, br d, J=9Hz), 6.6–6.9 (2H, m), 6.9–7.6 (12H, m), 7.88 (1H, br d, J=9Hz), 8.0 (1H, broad), 8.47 (1H, br d, J=9Hz), 9.1 (1H, broad).

Elemental Analysis. Calculated for C$_{37}$H$_{43}$N$_5$O$_7$·1/3-H$_2$O: C 65.76, H 6.51, N 10.36; Found: C 65.89, H 6.21, N 10.38.

(3)

Starting Compound: 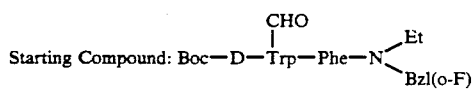

Object Compound: 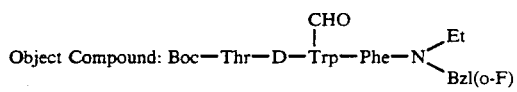

mp: 80°–103° C.

IR (Nujol): 3300, 1710, 1640, 1520 (broad), 1490 cm$^{-1}$.

NMR (DMSO-d$_6$, δ): 0.7–1.1 (6H, m), 1.33 (9H, s), 2.5–3.1 (4H, m), 3.1–3.5 (2H, m), 3.5–4.0 (2H, m), 4.2–5.1 (5H, m), 6.0–6.4 (1H, m), 6.8–7.7 (13H, m), 7.8–8.3 (2H, m), 8.5–8.8 (1H, m), 9.2 (1H, broad).

(4)

Starting Compound: 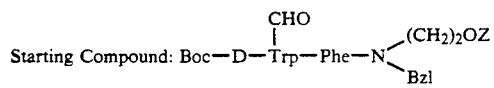

Object Compound: 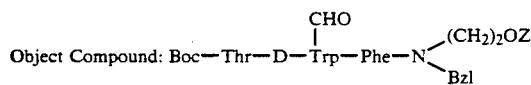

IR (Nujol): 3300, 1745, 1710, 1640 cm$^{-1}$.

NMR (DMSO-d$_6$, δ): 0.83 (3H, d, J=6Hz), 1.33 (9H, s), 2.5–3.1 (4H, m), 3.2–4.0 (4H, m), 4.13 (2H, br s), 4.4–5.2 (5H, m), 5.10 (s) and 5.13 (s)(2H), 6.25 (1H, br d, J=7Hz), 6.9–7.7 (14H, m), 7.35 (5H, s), 7.7–8.3 (2H, m), 8.4–8.8 (1H, m), 9.2 (1H, broad).

Elemental Analysis. Calculated for C$_{47}$H$_{53}$N$_5$O$_{10}$·1/2H$_2$O: C 65.87, H 6.35, N 8.17; Found: C 65.84, H 6.33, N 8.00.

EXAMPLE 53

The following object compounds were obtained from the corresponding starting compounds according to a similar manner to that of Example 3.

(1)

Starting Compound: 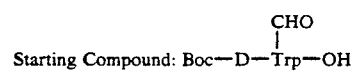

Object Compound: 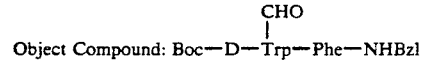

mp: 190°–191° C.

IR (Nujol): 3310, 1700, 1685, 1640, 1550, 1530 cm$^{-1}$.

NMR (DMSO-d$_6$, δ): 1.27 (9H, s), 2.6–3.1 (4H, m), 4.1–4.8 (2H, m), 4.35 (2H, d, J=6Hz), 6.92 (1H, br d, J=9Hz), 7.0–7.8 (14H, m), 8.2 (1H, broad), 8.47 (2H, br d, J=9Hz), 9.4 (1H, broad).

Elemental Analysis. Calculated for C$_{33}$H$_{36}$N$_4$O$_5$: C 69.70, H 6.38, N 9.85; Found: C 70.11, H 6.41, N 9.84.

(2)

Starting Compound: 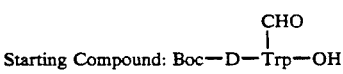

Object Compound: 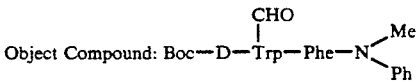

mp: ~102° C. (dec.).

IR (Nujol): 3300, 1710, 1640, 1595, 1495 cm$^{-1}$.

NMR (DMSO-d$_6$, δ): 1.27 (9H, s) 2.5–3.1 (4H, m), 3.16 (3H, s), 4.1–4.7 (2H, m), 6.6–7.0 (3H, m), 7.0–7.8 (12H, m), 8.15 (1H, br s), 8.46 (1H, br d, J=9Hz), 9.3 (1H, broad).

Elemental Analysis. Calculated for C$_{33}$H$_{36}$N$_4$O$_5$·H$_2$O: C 67.56, H 6.53, N 9.55; Found: C 67.67, H 6.60, N 9.18.

(3)

Starting Compound: 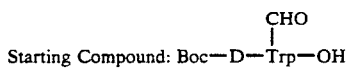

Object Compound: 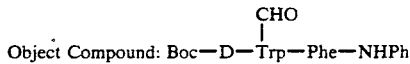

mp: 213°–215° C.

IR (Nujol): 3310, 1695, 1650, 1600, 1530, 1510 cm$^{-1}$.

NMR (DMSO-d$_6$, δ): 1.25 (9H, s), 2.5–3.3 (4H, m), 4.1–4.5 (1H, m), 4.5–5.0 (1H, m), 6.7–7.0 (1H, m), 7.0–7.8 (14H, m), 8.1 (1H, broad), 8.53 (1H, d, J=8Hz), 9.3 (1H, broad), 9.95 (1H, s).

Elemental Analysis. Calculated for C$_{32}$H$_{34}$N$_4$O$_5$: C 69.30, H 6.18, N 10.10; Found: C 69.35, H 6.33, N 9.99.

EXAMPLE 54

The following object compounds were obtained from the corresponding starting compounds according to a similar manner to that of Example 4.

(1)

Starting Compound: 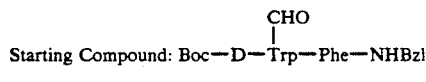

Object Compound: 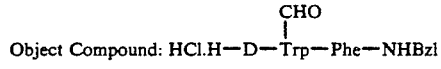

IR (Nujol): 3250 (broad), 1710, 1690, 1655 cm$^{-1}$.

NMR (DMSO-d$_6$, δ): 2.5–3.3 (4H, m), 3.9–4.3 (1H, m), 4.30 (2H, d, J=6Hz), 4.4–4.9 (1H, m), 7.0–7.5 (12H, m), 7.5–7.8 (2H, m), 8.0–8.3 (1H, broad), 8.36 (3H, br s), 8.88 (1H, br t, J=6Hz), 9.27 (1H, d, J=9Hz), 9.4 (1H, broad).

(2)

Starting Compound: Boc—D—Trp—Phe—NH$_2$

Object Compound: HCl.H—D—Trp—Phe—NH$_2$ mp: 222°–228° C. (dec.).
IR (Nujol): 3400, 1675, 1610, 1570, 1500 cm$^{-1}$.
NMR (DMSO-d$_6$, δ): 2.5–3.3 (4H, m), 3.8–4.1 (1H, m), 4.3–4.7 (1H, m), 6.8–7.4 (10H, m), 7.4–7.7 (2H, m), 7.94 (3H, s), 8.90 (1H, d, J=9Hz), 10.88 (1H, s).
Elemental Analysis. Calculated for C$_{20}$H$_{22}$N$_4$O$_2$.HCl: C 62.09, H 5.99, N 14.48, Cl 9.16; Found: C 61.89, H 5.93, N 14.37, Cl 9.37.

EXAMPLE 55

The following object compounds were obtained from the corresponding starting compounds according to a similar manner to that of Example 13.

(1)

Starting Compound: HCl.H—D—Trp(CHO)—Phe—NHBzl

Object Compound: Boc—Gln—D—Trp(CHO)—Phe—NHBzl mp: ~206° C. (dec.).
IR (Nujol): 3300, 1705, 1690, 1660, 1640, 1545 cm$^{-1}$.
NMR (DMSO-d$_6$, δ): 1.30 (9H, s), 1.5–2.2 (4H, m), 2.6–3.1 (4H, m), 3.7–4.2 (1H, m), 4.31 (2H, d, J=6Hz), 4.5–4.9 (2H, m), 6.6–6.9 (2H, m), 7.1–7.8 (15H, m), 7.8–8.3 (2H, m), 8.4–8.7 (2H, m), 9.3 (1H, broad).
Elemental Analysis. Calculated for C$_{38}$H$_{44}$N$_6$O$_7$.1/3-H$_2$O: C 64.94, H 6.41, N 11.96; Found: C 64.93, H 6.64, N 11.89.

(2)

Starting Compound: HCl.H—D—Trp(CHO)—Phe—N(Me)(Bzl)

Object Compound: Boc—MeThr—D—Trp(CHO)—Phe—N(Me)(Bzl)

mp: 75°–80° C.
IR (Nujol): 3420, 3300, 1710–1640 cm$^{-1}$.
NMR (DMSO-d$_6$, δ): 0.6–1.0 (3H, m), 1.35 (9H, s), 2.6–3.1 (4H, m), 2.73 (3H, s), 2.78 (s) and 2.85 (s)(3H), 3.6–5.2 (7H, m), 6.9–7.8 (14H, m), 7.8–8.2 (2H, m), 8.65 (1H, broad), 9.2 (1H, broad).

(3)

Starting Compound: HCl.H—D—Trp(CHO)—Phe—OBzl

Object Compound: Boc—Glu(OTce)—D—Trp(CHO)—Phe—OBzl mp: 147°–155° C.
IR (Nujol): 3330, 1720, 1690, 1645, 1540, 1525 cm$^{-1}$.
NMR (DMSO-d$_6$, δ): 1.32 (9H, s), 1.4–1.9 (2H, m), 1.9–2.4 (2H, m), 2.6–3.2 (4H, m), 3.8–4.3 (1H, m), 4.4–4.9 (2H, m), 4.83 (2H, s), 5.13 (2H, s), 6.7–7.0 (1H, m), 7.2–7.5 (3H, m), 7.25 (5H, s), 7.36 (5H, s), 7.5–7.8 (1H, m), 7.9–8.3 (2H, m), 8.6–8.9 (1H, m), 9.3 (1H, broad).

(4)

Starting Compound: HCl.H—Thr—D—Trp(CHO)—Phe—N(Me)(Bzl)

Object Compound: Z—Gly—Thr—D—Trp(CHO)—Phe—N(Me)(Bzl)

IR (Nujol): 3300, 1710, 1640 (sh), 1630, 1530 cm$^{-1}$.
NMR (DMSO-d$_6$, δ): 0.80 (3H, d, J=6Hz), 2.6–3.1 (4H, m), 2.77 and 2.84 (3H, s), 3.70 (2H, d, J=6Hz), 3.8 (1H, m), 4.1 (1H, m), 4.3–5.0 (5H, m), 4.92 (2H, s), 6.9–7.7 (15H, m), 7.27 (5H, s), 8.0 (2H, m), 8.6 (1H, t, J=6Hz), 9.15 (1H, br s).

(5)

Starting Compound: HCl.H—Thr—D—Trp(CHO)—Phe—N(Me)(Bzl)

Object Compound: Bu$^t$OCOCO—Thr—D—Trp(CHO)—Phe—N(Me)(Bzl)

IR (Nujol): 3300, 1710, 1660, 1630 cm$^{-1}$.
NMR (CDCl$_3$, δ): 1.09 (3H, d, J=6Hz), 1.48 (9H, s), 2.16 (1H, s), 2.67 and 2.77 (3H, s), 2.87 (2H, m), 3.15 (2H, m), 4.2–4.4 (4H, m), 4.6–5.1 (2H, m), 6.9–7.35 (14H, m), 7.45–7.6 (2H, m), 7.85 (1H, d, J=7Hz), 8.25 (1H, br), 9.0 (1H, br).

(6)

Starting Compound: HCl.H—Thr—D—Trp(CHO)—Phe—N(Me)(Bzl)

Object Compound:

Et$_2$N(CH$_2$)$_2$CO—Thr—D—Trp(CHO)—Phe—N(Me)(Bzl).HCl

IR (Nujol): 3300, 1710, 1660 (sh), 1640 cm$^{-1}$.
NMR (DMSO-d$_6$, δ): 0.80 (3H, d, J=6Hz), 1.17 (6H, t, J=7Hz), 2.77 and 2.83 (3H, s), 2.6–3.3 (12H, m), 3.77 (1H, m), 4.0–4.4 (3H, m), 4.5–4.8 (2H, m), 4.95 (1H, m), 7.0–7.4 (13H, m), 7.45–7.8 (2H, m), 8.0–8.3 (2H, m), 8.65 (1H, m), 9.3 (1H, br), 10.45 (1H, br).
Elemental Analysis. Calculated for C$_{40}$H$_{50}$N$_6$O$_6$.HCl.2.5H$_2$O: C 62.04, H 6.90, N 10.35; Found: C 61.44, H 6.89, N 10.86.

(7)

Starting Compound: HCl.H—Gln—D—Trp(CHO)—Phe—OBzl

Object Compound:

-continued

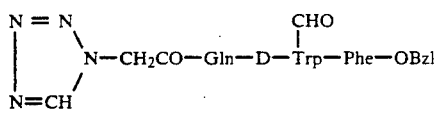

mp: 225°-227° C. (dec.).

IR (Nujol): 3450, 3300, 1730 (sh), 1710, 1660, 1640, 1650 cm$^{-1}$.

NMR (DMSO-d$_6$, δ): 1.5-2.15 (4H, m), 2.8 (2H, m), 3.1 (2H, m), 4.4 (1H, m), 4.7 (2H, m), 5.17 (2H, s), 5.30 (2H, s), 6.73 (1H, br), 7.27 (5H, s), 7.37 (5H, s), 7.2-7.6 (4H, m), 7.7 (1H, m), 8.2 (1H, m), 8.37 (1H, d, J=9Hz), 8.7 (2H, m), 9.27 (1H, br), 9.33 (1H, s).

Elemental Analysis. Calculated for C$_{36}$H$_{37}$N$_9$O$_6$: C 59.84, H 5.92, N 17.89; Found: C 59.37(59.29), H 5.38(5.32), N 17.47(17.40).

(8)

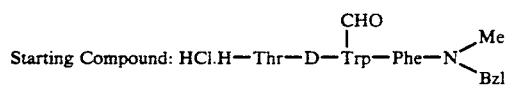

Object Compound:

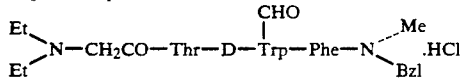

NMR (DMSO-d$_6$, δ): 0.83 (3H, d, J=6Hz), 1.13 (6H, t, J=7Hz), 2.87 (3H, s), 2.78 (2H, br), 2.9-3.0 (2H, m), 3.80 (1H, m), 3.97 (2H, s), 4.20 (1H, m), 4.3-5.0 (4H, m), 7.0-7.42 (13H, m), 7.5-7.8 m), 8.2 (2H, m), 8.7 (1H, m), 9.3 (1H, br), 9.9 (1H, br).

Elemental Analysis. Calculated for C$_{39}$H$_{48}$N$_6$O$_6$.HCl: C 63.88, H 6.73, N 11.46, Cl 4.83; Found: C 59.93, H 6.73, N 10.81, Cl 4.73.

(9)

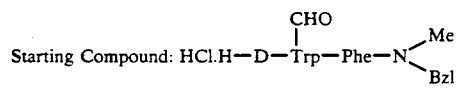

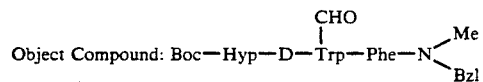

IR (Nujol): 3300, 1710, 1690, 1670, 1630 cm$^{-1}$.

NMR (DMSO-d$_6$, δ): 1.13, 1.20 and 1.33 (9H, s), 2.6-3.0 (9H, m), 3.23 (2H, m), 3.9-4.2 (2H, m), 4.3-5.1 (5H, m), 6.9-7.5 (14H, m), 7.65 (1H, m), 7.9-8.3 (2H, m), 8.8 (1H, m), 9.3 (1H, br).

(10)

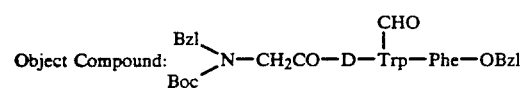

mp: 109°-110° C.

IR (Nujol): 3300, 1740, 1710, 1690, 1640 cm$^{-1}$.

NMR (DMSO-d$_6$, δ): 1.37 (9H, br s), 2.81 (2H, m), 3.07 (2H, m), 3.69 (2H, m), 4.28 (2H, m), 4.5-4.9 (2H, m), 5.14 (2H, s), 7.24 (5H, s), 7.38 (5H, s), 7.05-7.5 (9H, m), 7.66 (1H, m), 8.12 (1H, m), 8.78 (1H, d, J=8Hz), 9.31 (1H, br s).

Elemental Analysis. Calculated for C$_{42}$H$_{44}$N$_4$O$_7$: C 70.37, H 6.19, N 7.82; Found: C 69.42, H 6.39, N 7.58.

EXAMPLE 56

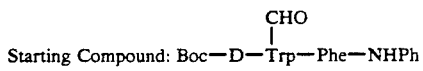

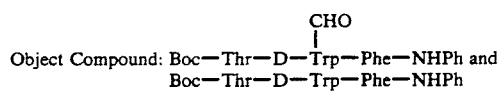

A mixture of Boc-D-Trp(CHO)-Phe-NHPh (0.93 g) in 4N-HCl/DOX (15 ml) was stirred for 3 hours. After evaporation, the residue was pulverized with diethyl ether, filtered washed with diethyl ether and dried. The residual powder (0.78 g) of HCl.H-D-Trp(CHO)-Phe-NHPh. Boc-Thr-OH (0.35 g) and HOBT (0.21 g) were dissolved in DMF (15 ml). To the solution was added WSC (0.29 ml) under ice-cooling and the mixture was stirred at room temperature. After stirring for 3, 4 and 5 hours, triethylamine (0.04 ml) was added respectively. Stirring was continued for further an hour. After evaporation, the residue was crystallized with 2% hydrochloric acid. The crystals were filtered, washed with water, 2% sodium hydrogen carbonate (twice) and water. The resultant crystals were subjected to column chromatography on silica gel (100 g) and eluted with a mixture of chloroform and methanol (50:1 to 30:1, gradient elution). The fractions containing less polar compound were combined and evaporated. The residue was pulverized with diisopropyl ether, filtered and dried to give Boc-Thr-D-Trp(CHO)-Phe-NHPh (0.10 g).

mp: 158°-160° C.

IR (Nujol): 3300, 1700, 1690, 1640, 1545 cm$^{-1}$.

NMR (DMSO-d$_6$, δ): 0.81 (3H, d, J=6Hz), 1.32 (9H, s), 2.6-3.3 (4H, m), 3.6-4.0 (2H, m), 4.4-4.8 (3H, m), 6.25 (1H, br d, J=9Hz), 6.9-7.7 (14H, m), 7.8-8.2 (2H, m), 8.55 (1H, br d, J=8Hz), 9.2 (1H, broad), 9.97 (1H, s).

The next fractions containing more polar compound on column chromatography were combined and evaporated. The residue was pulverized with diisopropyl ether, filtered and dried to give Boo-Thr-D-Trp-Phe-NHPh (0.45 g).

mp: 223°-226° C.

IP (Nujol): 3450, 3340, 1700, 1655, 1550, 1535 cm$^{-1}$.

NMR (DMSO-d$_6$, δ): 0.88 (3H, br d, J=6Hz), 1.32 (9H, s), 2.6-3.3 (4H, m), 3.6-4.0 (2H, m), 4.3-4.8 (3H, m), 6.26 (1H, br d, J=8Hz), 6.8-7.8 (15H, m), 7.92 (1H, br d, J=7Hz), 8.40 (1H, br d, J=8Hz), 9.79 (1H, s), 10.70 (1H, s).

Elemental Analysis. Calculated for C$_{35}$H$_{41}$N$_5$O$_6$.1/2-H$_2$O: C 66.02, H 6.65, N 11.00; Found: C 66.28, H 6.47, N 11.03.

EXAMPLE 57

The following object compound was obtained from the corresponding starting compound according to a similar manner to that of Example 23.

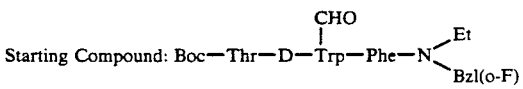

-continued

Object Compound: 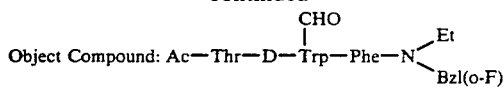

mp: ~110° C. (dec.).

IR (Nujol): 3310, 1710, 1640 (broad), 1535 cm⁻¹.

NMR (DMSO-d$_6$, δ): 0.7-1.2 (6H, m), 1.83 (3H, s), 2.5-3.1 (4H, m), 3.1-3.5 (2H, m), 3.5-3.9 (1H, m), 3.9-4.2 (1H, m), 4.2-5.1 (5H, m), 6.9-7.8 (14H, m), 7.8-8.3 (2H, m), 8.5-8.8 (1H, m), 9.2 (1H, broad).

EXAMPLE 58

Starting Compound: 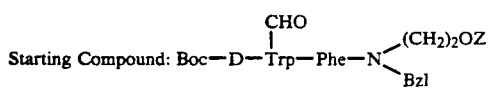

Object Compound: 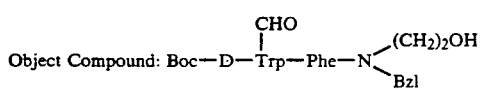

Boc-D-Trp(CHO)-Phe-N((CH$_2$)$_2$OZ)Bzl (0.75 g) was hydrogenated in ethanol (10 ml) with 10% palladium on carbon (0.15 g). The catalyst was filtered off and the filtrate was condensed under reduced pressure. The residue was subjected to column chromatography on silica gel (50 g) and eluted with chloroform and then a mixture of chloroform and methanol (50:1). The fractions containing the object compound was combined and evaporated. The residue was pulverized with n-hexane, filtered and dried to give Boc-D-Trp(CHO)-Phe-N((CH$_2$)$_2$OH)Bzl (0.57 g)

IR (Nujol): 3300, 1710, 1630 cm⁻¹.

NMR (DMSO-d$_6$, δ): 1.27 (9H, s), 2.5-3.1 (4H, m), 3.1-3.8 (4H, m), 4.0-5.3 (5H, m), 6.78 (1H, br d, J=8Hz), 6.9-7.9 (13H, m), 7.9-8.3 (11H, m), 8.58 (1H, d, J=9Hz), 9.3 (1H, broad).

Elemental Analysis. Calculated for C$_{35}$H$_{40}$N$_4$O$_6$.1/2-H$_2$O: C 67.62, H 6.65, N 9.01; Found: C 68.00, H 6.61, N 8.75.

EXAMPLE 59

The following object compounds were obtained from the corresponding starting compounds according to a similar manner to that of Example 58.

(1)

Starting Compound: 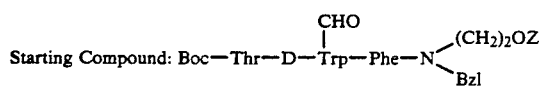

Object Compound: 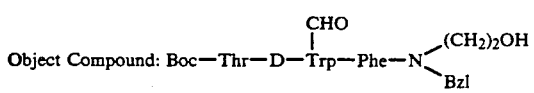

IR (Nujol): 3300, 1705, 1635 (broad) cm⁻¹.

NMR (DMSO-d$_6$, δ): 0.83 (3H, d, J=5Hz), 1.35 (9H, s), 2.5-4.0 (10H, m), 4.4-5.2 (6H, m), 6.1-6.4 (1H, m), 6.9-7.7 (14H, m), 7.7-8.2 (2H, m), 8.4-8.8 (1H, m), 9.15 (1H, broad).

(2)

Starting Compound: 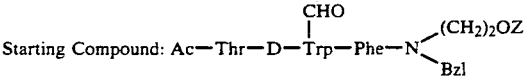

Object Compound: 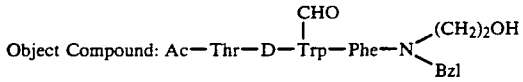

IR (Nujol): 3300, 1635 (broad), 1545, 1525 (broad) cm⁻¹.

NMR (DMSO-d$_6$, δ): 0.77 (3H, d, J=6Hz), 1.85 (3H, s), 2.6-3.9 (9H, m), 4.0-4.3 (1H, m), 4.4-5.3 (6H, m), 6.9-7.6 (13H, m), 7.6-7.9 (2H, m), 7.9-8.3 (2H, m), 8.66 (1H, d, J=9Hz), 9.2 (1H, broad).

(3)

Starting Compound: 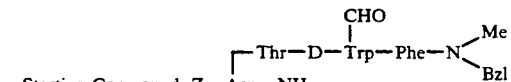

Object Compound: 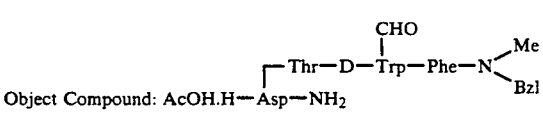

IR (Nujol): 3300, 1640, 1550 cm⁻¹.

NMR (DMSO-d$_6$, δ): 0.80 (3H, br d, J=6Hz), 1.87 (3H, s), 2.2-3.1 (9H, m), 3.3-3.6 (1H, m), 3.6-4.2 (6H, m), 4.2-5.1 (4H, m), 6.7-7.6 (16H, m), 7.6-8.2 (3H, m), 8.4-8.7 (1H, m), 9.2 (1H, broad).

(4)

Starting Compound: 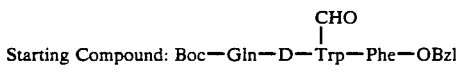

Object Compound: 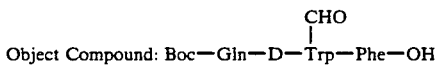

mp: ~187° C. (dec.).

IR (Nujol): 3300, 1700 (broad), 1640, 1525 cm⁻¹.

NMR (DMSO-d$_6$, δ): 1.30 (9H, s), 1.4-2.1 (4H, m), 2.5-3.6 (5H, m), 3.7-4.1 (1H, m), 4.3-4.8 (2H, m), 6.6-6.9 (2H, m), 7.0-7.5 (4H, m), 7.21 (5H, s), 7.5-7.7 (1H, m), 7.8-8.3 (2H, m), 8.50 (1H, br d, J=8Hz), 9.3 (1H, broad).

Elemental Analysis. Calculated for C$_{31}$H$_{37}$N$_5$O$_8$: C 61.27, H 6.14, N 11.53; Found: C 61.64, H 5.99, N 11.30.

(5)

Starting Compound: 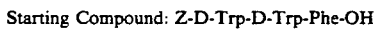

Object Compound: 

mp: ~193° C. (dec.).

NMR (DMSO-d$_6$, δ): 2.6-3.3 (6H, m), 4.1-5.3 (9H, m, overlapped with H$_2$O), 6.7-7.7 (17H, m), 8.1-8.5 (2H, m), 10.70 (1H, s), 10.86 (1H, s).

Elemental Analysis. Calculated for C$_{31}$H$_{31}$N$_5$O$_4$.3/2-H$_2$O C 65.94, H 6.07, N 12.40; Found: C 66.11, H 5.56, N 12.46.

EXAMPLE 60

The following object compound was obtained from the corresponding starting compound according to a similar manner to that of Example 23.

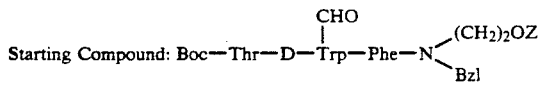

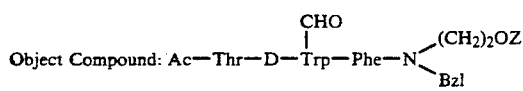

IR (Nujol): 3300, 1750, 1710, 1640, 1525 (broad) cm$^{-1}$.

NMR (DMSO-d$_6$, δ): 0.77 (3H, d, J=6Hz), 1.84 (3H, s), 2.6–3.1 (4H, m), 3.2–4.3 (6H, m), 4.4–5.1 (5H, m), 5.12 (2H, s), 6.9–7.8 (15H, m), 7.34 (5H, s), 7.8–8.3 (2H, m), 8.4–8.8 (1H, m), 9.2 (1H, broad).

EXAMPLE 61

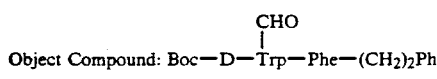

To a solution of Boc-D-Trp(CHO)-OH (0.92 g) in methylene chloride (15 ml) were added NMM (0.28 ml) and isobutyl chloroformate (0.36 ml) successively at −15° C., and the mixture was stirred for ten minutes. On the other hand, a solution of HCl.H-Phe-(CH$_2$)$_2$Ph (0.80 g) in methylene chloride (15 ml) was cooled at −30° C. and thereto was added NMM (0.28 ml). This solution was added to the above mentioned mixture at −50° C., and stirred for an hour at −50° C. and then stirred for 2 hours at room temperature. After evaporation and extraction with ethyl acetate, the organic layer was washed successively with 2% hydrochloric acid, water, 2% sodium hydrogen carbonate solution, water, and saturated sodium chloride solution, and dried over magnesium sulfate. After evaporation, the residual white crystals were filtered and washed with n-hexane. The crystals were recrystallized from ethanol to give Boc-D-Trp(CHO)-Phe-(CH$_2$)$_2$Ph (1.16 g).

mp: 171°–172° C.

IR (Nujol): 3350, 1720, 1660, 1520 cm$^{-1}$.

NMR (DMSO-d$_6$, δ): 1.13 (9H, s), 2.5–3.2 (8H, m), 4.25 (1H, br q, J=7Hz), 4.3–4.7 (1H, m), 6.6–7.7 (5H, m), 7.10(10H, s), 7.8–8.2 (1H, m), 8.58 (1H, d, J=9Hz), 9.3 (1H, broad).

Elemental Analysis. Calculated for C$_{34}$H$_{37}$N$_3$O$_5$: C 71.94, H 6.57, N 7.40; Found: C 7180, H 6.58, N 7.53.

EXAMPLE 62

The following object compound was obtained from the corresponding starting compound according to a similar manner to that of Example 24.

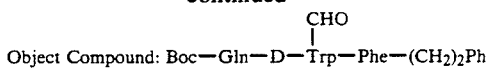

mp: ~193° C. (dec.).

IR (Nujol): 3330, 1710, 1690, 1655, 1640, 1525 cm$^{-1}$.

NMR (DMSO-d$_6$, δ): 1.31 (9H, s), 1.4–2.1 (4H, m), 2.5–3.3 (8H, m), 3.7–4.1 (1H, m), 4.3–4.8 (2H, m), 6.6–6.9 (2H, m), 7.0–7.8 (5H, m), 7.18 (10H, s), 7.8–8.3 (2H, m), 8.3–8.7 (1H, m), 9.25 (1H, broad).

Elemental Analysis. Calculated for C$_{39}$H$_{45}$N$_5$O$_7$: C 67.32, H 6.52, N 10.06; Found: C 67.14, H 6.52, N 10.03.

EXAMPLE 63

The following compounds were obtained from the compounding starting compounds according to a similar manner to that of Example 17.

(1)

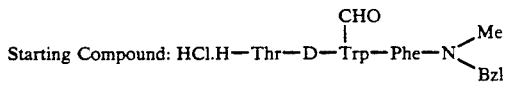

Object Compound:

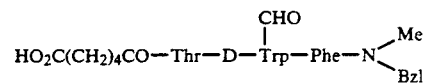

mp: 110°–116° C.

IR (Nujol): 3300, 1710, 1640, 1540 (broad) cm$^{-1}$.

NMR (DMSO-d$_6$, δ): 0.81 (3H, d, J=6Hz), 1.46 (4H, br s), 1.8–2.3 (4H, m), 2.6–3.2 (4H, m), 2.77 (s) and 2.83 (s)(3H), 3.6–4.0 (1H, m), 4.0–5.2 (6H, m), ca. 6.3 (1H, broad), 6.9–7.4 (12H, m), 7.4–7.8 (3H, m), 7.8–8.2 (2H, m), 8.4–8.8 (1H, m), 9.2 (1H, broad).

(2)

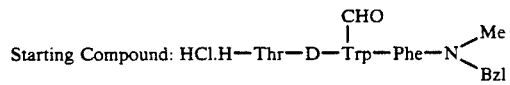

Object Compound:

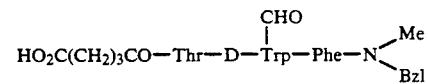

mp: ~145° C. (dec.).

IR (Nujol): 3300, 1710, 1635, 1540 (broad) cm$^{-1}$.

NMR (DMSO-d$_6$, δ): 0.82 (3H, d, J=6Hz), 1.5–1.9 (2H, m), 1.9–2.4 (4H, m), 2.6–3.2 (4H, m), 2.75 (s) and 2.82 (s)(3H), 3.7–4.0 (1H, m), 4.0–5.2 (7H, m), 6.9–7.4 (12H, m), 7.4–7.8 (3H, m), 7.9–8.3 (2H, m), 8.4–8.8 (1H, m), 9.3 (1H, broad).

(3)

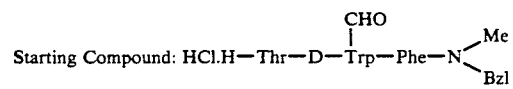

Object Compound:

-continued

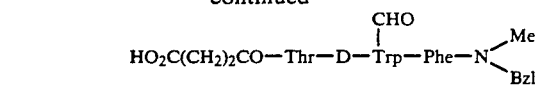

mp: ~160° C. (dec.).

IR (Nujol): 3300, 1710, 1640, 1540 (broad) cm⁻¹.

NMR (DMSO-d₆, δ): 0.84 (3H, d, J=6Hz), 2.35 (4H, s), 2.6–3.1 (7H, m), 3.7–5.1 (8H, m), 6.9–7.4 (12H, m), 7.4–7.9 (3H, m), 7.9–8.3 (2H, m), 8.6–8.9 (1H, m), 9.2 (1H, broad).

Elemental Analysis. Calculated for C₃₇H₄₁N₅O₈·H₂O: C 63.33, H 6.18, N 9.89; Found: C 63.03, H 5.90, N 9.79.

(4)

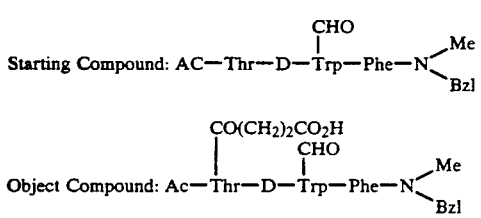

mp: ~135° C.

IR (Nujol): 3500, 3290, 1735, 1710, 1640, 1550 cm⁻¹.

NMR (DMSO-d₆, δ): 0.82 (3H, d, J=6Hz), 1.82 (3H, s), 2.27 (4H, s), 2.86 (3H, s), 2.6–3.0 (4H, m), 4.30 and 4.53 (2H, ABq, J=15Hz), 4.4–5.1 (4H, m), 6.9–7.6 (13H, m), 7.7 (1H, m), 7.90 (1H, d, J=7Hz), 8.1 (1H, m), 8.22 (1H, d, J=7Hz), 8.73 (1H, m), 9.28 (1H, br).

Elemental Analysis. Calculated for C₃₈H₄₃N₅O₇·H₂O: C 62.98, H 6.10, N 9.42; Found: C 62.98, H 6.20, N 9.48.

(5)

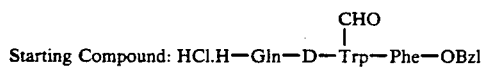

Starting Compound: HCl.H—Gln—D—Trp—Phe—OBzl

Object Compound: HO₂C(CH₂)₂CO—Gln—D—Trp—Phe—OBzl mp: 229°–230° C. (dec.).

IR (Nujol): 3400, 3280, 1725, 1710, 1660, 1640, 1550 cm⁻¹.

NMR (DMSO-d₆, δ): 1.47–2.1 (4H, m), 2.40 (4H, s), 2.86 (2H, m), 3.04 (2H, m), 4.20 (1H, m), 4.63 (2H, m), 5.13 (2H, s), 6.73 (1H, br), 7.28 (5H, s), 7.37 (5H, s), 7.1–7.5 (4H, m), 7.6 (1H, m), 8.1 (3H, m), 8.73 (1H, d, J=7Hz), 9.3 (1H, br).

(6)

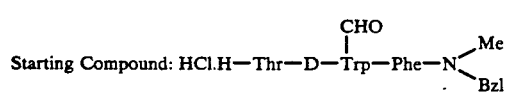

Object Compound:

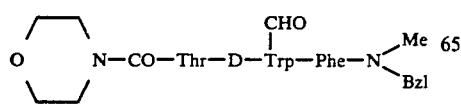

IR (Nujol): 3400, 3280, 1710, 1660 (sh), 1640 (sh), 1630, 1530 cm⁻¹.

DMSO-d₆, δ): 0.80 (3H, t, J=6Hz), 2.77 (2H, m), 2.83 (3H, s), 2.83 (2H, m), 3.28 (4H, s), 3.50 (4H, br s), 3.65–4.1 (2H, m), 4.2–5.1 (5H, m), 6.12 (1H, d, J=7Hz), 6.95–7.4 (13H, m), 7.4–7.6 (2H, m), 8.1 (6H, m), 8.6 (1H, m), 9.25 (1H, br s).

(7)

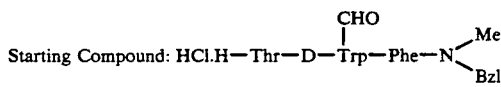

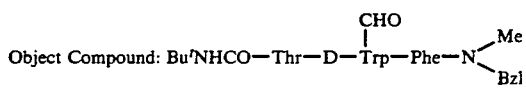

IR (Nujol): 3360, 3220, 1710, 1650, 1630, 1550 cm⁻¹.

NMR (DMSO-d₆, δ): 0.78 (3H, d, J=6Hz), 1.20 (9H, s), 2.83 (3H, s), 2.6–3.15 (4H, m), 3.6–4.05 (2H, m), 4.30 and 4.63 (2H, ABq, J=15Hz), 4.5–5.2 (3H, m), 5.90 (1H, d, J=7Hz), 6.14 (1H, s), 6.9–7.7 (15H, m), 7.86 (1H, m), 8.13 (1H, m), 8.66 (1H, m), 9.23 (1H, br s).

EXAMPLE 64

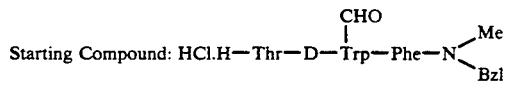

Object Compound:

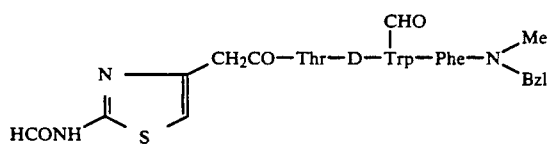

To a solution of DMF (0.17 ml) in ethyl acetate (0.68 ml) was added phosphorus oxychloride (0.20 ml) at −10° C. The mixture was stirred for 25 minutes. 2-Formamidothiazol-4-ylacetic acid (0.37 g) and ethyl acetate (0.68 ml) were added and the mixture was stirred for an hour (mixture A). On the other hand, to the mixture of HCl.H-Thr-D-Trp(CHO)-Phe-NMeBzl (1.24 g) in ethyl acetate (20 ml) was added bis(trimethylsilyl)acetamide (3.0 ml). After stirring for an hour at room temperature, the mixture was cooled at −15° C. To the mixture was added the mixture A and stirred for 1.5 hours at −15° C. Water (15 ml) was added and the mixture was stirred for 20 minutes at room temperature. The organic layer was separated and washed with 2% hydrochloric acid, water, 2% sodium hydrogencarbonate, water and saturated sodium chloride solution and dried over magnesium sulfate. After evaporation the residue was subjected to column chromatography on silica gel (100 g) and eluted with a mixture of chloroform and methanol (30:1). The fractions containing the object compound were combined and evaporated. The residue was pulverized with diisopropyl ether, filtered and dried to give

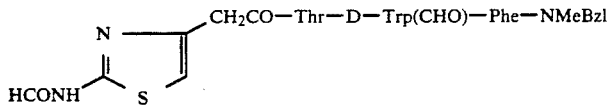

(1.08 g).

mp: ~130° C. (dec.).

IR (Nujol): 3300, 1710–1640, 1545–1510 cm$^{-1}$.

NMR (DMSO-d$_6$, δ): 0.82 (3H,, d, J=6Hz), 2.6–3.2 (4H, m), 2.77 (s) and 2.84 (s)(3H), 3.57 (2H, s), 3.7–5.1 (7H, m), 6.88 (1H, s), 6.9–7.7 (14H, m), 7.7–8.4 (4H, m), 8.6–8.9 (1H, m), 9.1 (1H, broad), 12.0 (1H, broad).

Elemental Analysis. Calculated for C$_{39}$H$_{41}$N$_7$O$_7$O.5/2H$_2$O: C 58.78, H 5.82, N 12.30; Found: C 58.74, H 5.46, N 11.97.

EXAMPLE 65

The following compounds were obtained from the corresponding starting compounds according to a similar manner to that of Example 15.

(1)

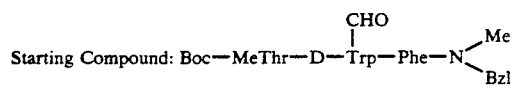

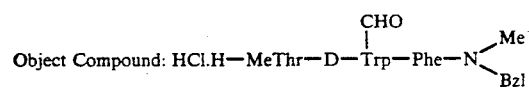

mp: ~148° C. (dec.).

IR (Nujol): 3300, 1710, 1675, 1635, 1550 cm$^{-1}$.

NMR (DMSO-d$_6$, δ): 0.64 (3H, d, J=6Hz), 2.34 (3H, s), 2.6–3.1 (4H, m), 2.77 (s) and 2.86 (s)(3H), 3.4–3.8 (2H, m), 4.2–5.2 (4H, m), 5.5–5.7 (1H, m), 6.9–7.5 (12H, m), 7.59 (1H, s), 7.7–7.9 (1H, m), 7.9–8.2 (1H, m), 8.7–9.1 (4H, m), 9.3 (1H, broad).

(2)

Starting Compound: Boc—Gln—D—Trp—Phe—NH$_2$

Object Compound: H—Gln—D—Trp—Phe—NH$_2$ mp: ~269° C. (dec.).

IR (Nujol): 3300, 1670 (broad), 1640, 1535 cm$^{-1}$.

NMR (DMSO-d$_6$, δ): 1.3–2.2 (6H, m), 2.6–3.4 (5H, m), 4.2–4.6 (2H, m), 6.6 (1H, br s), 6.7–7.5 (3H, m), 7.9 (1H, broad), 8.24 (1H, d, J=9Hz), 10.64 (1H, s).

Elemental Analysis. Calculated for C$_{25}$H$_{30}$N$_6$O$_4$.1/4-H$_2$O: C 62.16, H 6.36, N 17.40; Found: C 62.23, H 6.19, N 17.24.

(3)

Starting Compound: Boc-D-Trp-D-Trp-Phe-OBzl

Object Compound: HCl.H-D-Trp-D-Trp-Phe-OBzl (4)

Starting Compound:

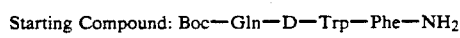

Object Compound:

mp: 137° C. (dec.).

IR (Nujol): 3300, 1730 (sh), 1710, 1630 cm$^{-1}$.

NMR (DMSO-d$_6$, δ): 0.80 (3H, d, J=6Hz), 2.77, 2.87 (s), and 2.5–3.0 (m)(7H), 3.87 (1H, m), 4.1–4.25 (1H, m), 4.35–5.1 (5H, m), 6.9–7.4 (9H, m), 7.2 (5H, s), 7.6 (1H, m), 7.95–8.3 (3H, m), 8.6 (1H, m), 9.2 (1H, br).

(5)

Starting Compound:

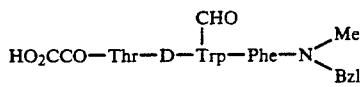

Object Compound:

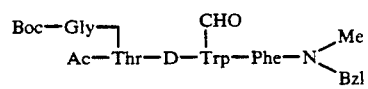

mp: ~120° C.

IR (Nujol): 3280, 1760, 1710 (h), 1695 (sh), 1670, 1640 cm$^{-1}$.

NMR (DMSO-d$_6$, δ): 0.87 (3H, d, J=6Hz), 1.87 (3H, s), 2.83 (3H, s), 2.6–3.0 (4H, m), 3.67 (2H, s), 4.28 and 4.63 (2H, ABq, J=15Hz), 4.95 (2H, m), 4.5 (2H, m), 6.9–7.3 (13H, m), 7.47 (1H, m), 7.67 (1H, m), 8.02 (1H, d, J=7Hz), 8.29 (4H, br), 8.70 (1H, d, J=7Hz), 9.25 (1H, br).

(6)

Starting Compound:

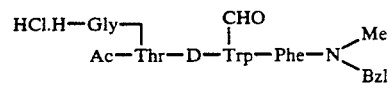

Object Compound:

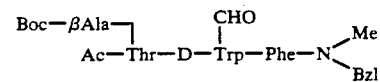

IR (Nujol): 3250, 1740, 1710, 1660 (sh), 1640 cm$^{-1}$.

NMR (DMSO-d$_6$, δ): 0.87 (3H, d, J=7Hz), 1.87 (3H, s), 2.56 (2H, t, J=7Hz), 2.87 (3H, s), 2.7–3.15 (4H, m), 4.30 and 4.63 (2H, ABq, J=15Hz), 4.4–5.1 (4H, m), 7.0–7.4 (14H, m), 7.58 (1H, br s), 7.75 (1H, m), 8.1 (3H, m), 8.48 (1H, d, J=8Hz), 8.76 (1H, m), 9.3 (1H, br s).

(7)

Starting Compound:

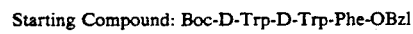

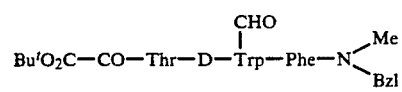

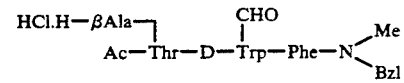

-continued

Boc—N(CH₂CO₂Buᵗ)CH₂CO—D—Trp(CHO)—Phe—OBzl

Object Compound:

HO₂CCH₂NHCH₂CO—D—Trp(CHO)—Phe—OBzl mp: ~205° C. (dec.).
IR (Nujol): 3300, 1715, 1640, 1550 cm⁻¹.
NMR (DMSO-d₆, δ): 2.82 (2H, m), 3.05 (2H, m), 3.17 (2H, s), 3.30 (2H, s), 4.4–4.9 (2H, m), 5.16 (2H, s), 7.26 (5H, s), 7.37 (5H, s), 7.2–7.5 (4H, m), 7.65 (1H, m), 8.2 (1H, br), 8.32 (1H, d, J=8Hz), 8.87 (1H, d, J=8Hz), 9.25 (1H, br s).
Elemental Analysis. Calculated for C₃₂H₃₂N₄O₇: C 65.74, H 5.52, N 9.58; Found: C 64.21, H 5.35, N 9.17.

(8)

Starting Compound:

Boc—N(Bzl)CH₂CO—D—Trp(CHO)—Phe—OBzl

Object Compound:

HCl.HN(Bzl)CH₂CO—D—Trp(CHO)—Phe—OBzl mp: ~200° C. (dec.).
IR (Nujol): 3270, 2600–2700, 1710 (sh), 1680 (sh), 1695 cm⁻¹.
NMR (DMSO-d₆, δ): 2.78 (2H, m), 3.03 (2H, m), 3.58 (2H, s), 4.02 (2H, s), 4.4–4.9 (2H, m), 5.13 (28H, s), 7.25 (5H, s), 7.36 (5H, s), 7.44 (5H, s), 7.2–7.7 (4H, m), 8.15 (1H, br), 8.81 (1H, d, J=8Hz), 8.96 (1H, d, J=8Hz), 9.4 (2H, br).
Elemental Analysis. Calculated for C₃₇H₃₇N₄O₅Cl: C 68.04, H 5.71, N 8.58, Cl 5.43; Found: C 65.21, H 5.47, N 7.94, Cl 2.47.

EXAMPLE 66

Starting Compound: HCl.H—Gln—D—Trp(CHO)—Phe—OBzl

Object Compound: pGlu—D—Trp(CHO)—Phe—OBzl

A mixture of HCl.H-Gln-D-Trp(CHO)-Phe-OBzl (0.48 g) in AcOH (25 ml) was stirred for 8 hours at 50° C. After evaporation, the residue was pulverized with water. The white solid was filtered and washed successively with 2% hydrochloric acid, water, 2% sodium hydrogencarbonate and water, and dried. The obtained powder was dissolved in DMF and reprecipitated with ethyl acetate. The precipitate was filtered and dried to give pGlu-D-Trp(CHO)-Phe-OBzl (0.35 g).
mp: 205°–209° C.
IR (Nujol): 3300, 1710, 1640, 1550 cm⁻¹.
NMR (DMSO-d₆, δ): 1.3–1.8 (1H, m), 1.8–2.3 (3H, m), 2.6–3.3 (4H, m), 3.9–4.1 (1H, m), 4.4–4.9 (2H, m), 5.10 (2H, s), 7.1–7.5 (3H, m), 7.17 (5H, s), 7.29 (5H, s), 7.5–7.8 (2H, m), 8.08 (2H, br d, J=9Hz), 8.72 (1H, d, J=8Hz), 9.3 (1H, broad).

Elemental Analysis. Calculated for C₃₃H₃₂N₄O₆: C 68.26, H 5.55, N 9.65; Found: C 67.96, H 5.57, N 9.61.

EXAMPLE 67

Starting Compound: HCl.H—Gln—D—Trp(CHO)—Phe—OBzl

Object Compound: HCO—Gln—D—Trp(CHO)—Phe—OBzl

To a solution of HCl.H-Gln-D-Trp(CHO)-Phe-OBzl (0.33 g) and sodium formate (0.35 g) in formic acid (21 ml) was added dropwise Ac₂O (7 ml) under ice-cooling. The mixture was stirred for three and half an hour at room temperature. Water (10 ml) was added to the mixture and then evaporated. To the residue, water was added and evaporated. The residue was pulverized with water, filtered. The solids were dissolved in DMF and reprecipitated with ethyl acetate, filtered and dried to give HCO-Gln-D-Trp(CHO)-Phe-OBzl (0.27 g).
mp: ~217° C. (dec.).
IR (Nujol): 3300, 1710, 1660, 1640, 1550 cm⁻¹.
NMR (DMSO-d₆, δ): 1.3–2.2 (4H, m), 2.6–3.2 (4H, m), 4.1–4.9 (3H, m), 5.14 (2H, s), 6.7 (1H, br s), 7.0–7.8 (5H, m), 7.21 (5H, s), 7.32 (5H, s), 7.9–8.5 (4H, m), 8.73 (1H, br d, J=8Hz), 9.3 (1H, broad).

EXAMPLE 68

Starting Compound: Boc—Glu(OTce)—D—Trp(CHO)—Phe—OBzl

Object Compound: Boc—Glu—D—Trp(CHO)—Phe—OBzl

To a solution of Boc-Glu(OTce)-D-Trp(CHO)-Phe-OBzl (0.40 g) in 90% AcOH (10 ml), was added zinc (0.20 g). The mixture was stirred for four and half an hour at room temperature. After filtration and evaporation, the residue was extracted with ethyl acetate. The organic layer was washed with water and saturated sodium chloride, and dried over magnesium sulfate. The evaporated residue was subjected to column chromatography on silica gel (20 g) and eluted with a mixture of chloroform and methanol (30:1 to 9:1, gradient elution). The fractions containing the object compound were combined and evaporated. The residue was pulverized with n-hexane, filtered and dried to give Boc-Glu-D-Trp(CHO)-Phe-OBzl (0.27 g).
mp: 172°–175° C.
IR (Nujol): 3320, 1720, 1710, 1690, 1640, 1545, 1525 cm⁻¹.
NMR (DMSO-d₆, δ): 1.32 (9H, s), 1.5–2.3 (4H, m), 2.6–3.4 (5H, m), 3.8–4.2 (1H, m), 4.4–4.9 (2H, m), 5.12 (2H, s), 6.7–7.0 (1H, m), 7.1–7.8 (4H, m), 7.25 (5H, s), 7.35 (5H, s), 7.9–8.4 (2H, m), 8.6–8.9 (1H, m), 9.3 (1H, broad).
Elemental Analysis. Calculated for C₃₈H₄₂N₄O₉.1/2-H₂O: C 64.49, H 6.12, N 7.92; Found: C 64.48, H 5.98, N 7.87.

EXAMPLE 69

Starting Compound: Boc—Gln—D—Trp(CHO)—Phe—OBzl

-continued

Object Compound: Boc—Gln—D—Trp—Phe—OH

A mixture of Boc-Gln-D-Trp(CHO)-Phe-OBzl (1.2 g) and 1N sodium hydroxide (3.6 ml) in a mixture of THF (30 ml), methanol (10 ml) and water (5 ml) was stirred for 1.5 hours. After adding water (10 ml), the organic solvent was evaporated. The resulting aqueous solution was washed with diethyl ether, acidified with 10% citric acid solution and allowed to stand in a refrigerator overnight. The precipitates were filtered, washed with water and recrystallized with a mixture of ethanol and water to give Boc-Gln-D-Trp-Phe-OH (0.80 g).

mp: 168°-170° C.

IR (Nujol): 3320, 1715, 1690, 1645, 1545, 1530 cm$^{-1}$.

NMR (DMSO-d$_6$, δ): 1.33 (9H, s), 1.4–2.2 (4H, m), 2.6–3.5 (4H, m), 3.7–4.1 (1H, m), 4.3–4.8 (2H, m), 6.6–7.6 (13H, m), 7.86 (1H, d, J=8Hz), 8.36 (1H, d, J=9Hz), 10.70 (1H, s), 12.7 (1H, broad).

Elemental Analysis. Calculated for C$_{30}$H$_{37}$N$_5$O$_7$·1/2-H$_2$O: C 61.21, H 6.51, N 11.90; Found: C 61.42, H 6.31, N 11.90.

EXAMPLE 70

The following object compound was obtained from the corresponding starting compound according to a similar manner to that of Example 71.

Starting Compound: Boc—Gln—D—Trp(CHO)—Phe—OBzl

Object Compound: Boc—Gln—D—Trp—Phe—NH$_2$ mp: 210°-212° C.

IR (Nujol): 3420, 3300, 3220, 1690, 1640, 1540, 1525 cm$^{-1}$.

NMR (DMSO-d$_6$, δ): 1.33 (9H, s), 1.4–2.1 (4H, m), 2.6–3.2 (4H, m), 3.7–4.1 (1H, m), 4.3–4.7 (2H, m), 6.6–7.6 (10H, m), 7.22 (5H, s), 7.7–8.0 (1H, m), 8.1–8.4 (1H, m), 10.73 (1H, s).

Elemental Analysis. Calculated for C$_{30}$H$_{38}$N$_6$O$_6$: C 62.27, H 6.62, N 14.52; Found: C 62.03, H 6.59, N 14.36.

EXAMPLE 71

Starting Compound: Boc-D-Trp-Phe-OBzl

Object Compound: Boc-D-Trp-Phe-NH$_2$

A mixture of Boc-D-Trp-Phe-OBzl (1.0 g) and 24% methanolic ammonia (20 ml) was allowed to stand at room temperature in a sealed tube for 18 hours. After evaporation, the residual crystals were collected and recrystallized from a mixture of water and ethanol to give Boc-D-Trp-Phe-NH$_2$ (0.63 g).

mp: 204°-206° C.

IR (Nujol): 3430, 3350, 1675, 1640, 1550, 1535 cm$^{-1}$.

NMR (DMSO-d$_6$, δ): 1.30 (9H, s), 2.5–3.4 (4H, m), 3.9–4.6 (2H, m), 6.68 (1H, br d, J=8Hz), 6.8–7.6 (12H, m), 8.13 (1H, br d, J=9Hz), 10.63 (1H, s).

Elemental Analysis. Calculated for C$_{25}$H$_{30}$N$_4$O$_4$: C 66.65, H 6.71, N 12.44; Found: C 66.92, H 6.72, N 12.33.

EXAMPLE 72

The following object compound was obtained from the corresponding starting compound according to similar manners to those of Example 4 and Example 13, successively.

Starting Compound: Boc—D—Trp(CHO)—Phe—OBzl

Object Compound: Z—D—Trp—D—Trp(CHO)—Phe—OBzl mp: 169°-173° C.

IR (Nujol): 3300, 1710, 1690, 1645, 1540 cm$^{-1}$.

NMR (DMSO-d$_6$, δ): 2.6–3.3 (6H, m), 4.1–5.0 (3H, m), 4.94 (2H, s), 5.13 (2H, s), 6.7–7.8 (25H, m), 8.0–8.4 (2H, m), 8.74 (1H, d, J=8Hz), 9.2 (1H, broad).

Elemental Analysis. Calculated for C$_{47}$H$_{43}$N$_5$O$_7$: C 71.47, H 5.49, N 8.87; Found: C 71.61, H 5.37, N 8.87.

EXAMPLE 73

The following object compound was obtained from the corresponding starting compound according to a similar manner to that of Example 69.

Starting Compound: Z—D—Trp—D—Trp(CHO)—Phe—OBzl

Object Compound: Z—D—Trp—D—Trp—Phe—OH mp: 153°-160° C. (dec.).

IR (Nujol): 3600, 3400, 3300, 1740, 1670, 1640, 1565, 1540 cm$^{-1}$.

NMR (DMSO-d$_6$, δ): 2.6–3.2 (6H, m), 3.2–3.6 (3H, broad), 4.1–4.9 (3H, m), 4.93 (2H, s), 6.8–7.5 (19H, m), 7.5–7.7 (2H, m), 7.9–8.2 (1H, m), 8.43 (1H, d, J=9Hz), 10.74 (2H, s).

Elemental Analysis. Calculated for C$_{39}$H$_{37}$N$_5$O$_6$·H$_2$O: C 67.91, H 5.70, N 10.15; Found: C 67.99, H 5.58, N 10.16.

EXAMPLE 74

The following object compound was obtained from the corresponding starting compound according to similar manners to those of Example 15 and continuously Example 17.

Starting Compound: Boc—Thr—D—Trp(Tos)—Phe—N(Me)(Bzl)

Object Compound: Ac—Thr—D—Trp(Tos)—Phe—N(Me)(Bzl)

mp: 112°-116° C.

IR (Nujol): 3400, 3250, 1660 (sh), 1640, 1170 cm$^{-1}$.

NMR (DMSO-d$_6$, δ): 0.78 (3H, d, J=6Hz), 1.97 (3H, s), 2.27 (3H, s), 2.80 (3H, s), 2.6–3.1 (4H, m), 3.75 (1H, m), 4.1 (1H, m), 4.3–5.0 (5H, m), 6.9–7.35 (14H, m), 7.5–7.9 (6H, m), 8.05 (1H, d, J=6Hz), 8.60 (1H, t, J=6Hz).

Elemental Analysis. Calculated for C$_{41}$H$_{45}$N$_5$O$_7$S: C 65.49, H 6.03, N 9.31; Found: C 64.80, H 6.03, N 9.24.

EXAMPLE 75

Starting Compound:

Z—Gly—Thr—D—Trp(CHO)—Phe—N(Me)(Bzl)

-continued

Object Compound:

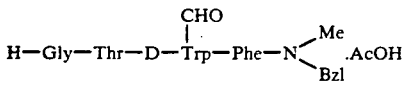

A solution of Z-Gly-Thr-D-Trp(CHO)-Phe-NMeBzl (560 mg) in a mixed solvent of ethanol (30 ml) and acetic acid (10 ml) was hydrogenated over 10% palladium on carbon (350 mg) under atmospheric pressure for two hours. After filtration of the catalyst and evaporation, the residue was dissolved in water (50 ml) and lyophilized to give H-Gly-Thr-D-Trp(CHO)-Phe-NMeBzl.AcOH (230 mg).

IR (Nujol): 3300, 1720 (sh), 1690 (sh), 1660 (sh), 1640 cm$^{-1}$.

NMR (DMSO-d$_6$/D$_2$O, δ): 0.80 (3H, d, J=6Hz), 2.80 and 2.97 (3H, s), 2.6-3.0 (4H, m), 3.27 (2H, m), 4.3-5.1 (5H, m), 7.20 (5H, s), 6.8-7.6 (10H, m), 8.0 (1H, br), 9.1 (1H, br).

EXAMPLE 76

The following object compound was obtained from the corresponding starting compound according to a similar manner to that of Example 79.

Starting Compound:

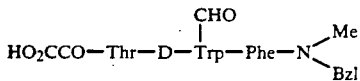

Object Compound:

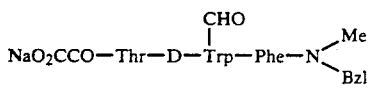

IR (Nujol): 3300, 1710, 1685, 1660, 1640 cm$^{-1}$.
NMR (D$_2$O, δ): 1.03 (3H, d, J=6Hz), 2.37 and 2.63 (3H, s), 2.5 (2H, m), 2.9 (2H, m), 3.7 (1H, m), 4.0-4.3 (2H, m), 5.4 (1H, m), 6.6-7.4 (14H, m), 8.9 (1H, m), 9.8 (1H, br s).

EXAMPLE 77

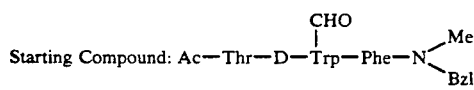

Object Compound:

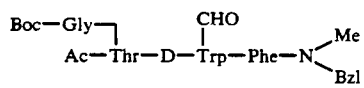

To a solution of Ac-Thr-D-Trp(CHO)-Phe-NMeBzl (1.07 g), Boc-Gly-OH (0.36 g) and 4-dimethylaminopyridine (125.3 g) in DMF (16 ml) was added WSC.HCl (392 mg) at room temperature. After stirring the solution overnight, Boc-Gly-OH (175 mg) and WSC.HCl (191 mg) were added thereto, and the solution was further stirred for 18 hours. The solution was concentrated under vacuum, and the product was extracted with ethyl acetate. The extract was washed successively with water, diluted sodium hydrogencarbonate solution, 0.5N hydrochloric acid, and sodium chloride solution and dried over magnesium sulfate. The crude product was purified on a silica gel column chromatography (25 g) eluting with chloroform-methanol (100:2 to 100:2.5) to give Ac-Thr(Boc-Gly)-D-Trp(CHO)-Phe-NMeBzl (1.26 g) as an amorphous solid.

NMR (DMSO-d$_6$, δ): 0.80 (3H, d, J=6Hz), 1.37 (9H, s), 1.83 (3H, s), 2.83 (3H, s), 2.7-3.1 (4H, m), 3.55 (2H, d, J=6Hz), 4.28 and 4.63 (2H, ABq, J=15Hz), 4.4-5.1 (4H, m), 6.9-7.5 (14H, m), 7.77 (1H, m), 8.0 (1H, t, J=7Hz), 8.15 (1H, m), 8.30 (1H, d, J=7Hz), 8.67 (1H, m), 9.30 (1H, br s).

EXAMPLE 78

The following object compound was obtained from the corresponding starting compound according to a similar manner to that of Example 77.

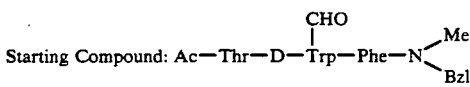

Object Compound:

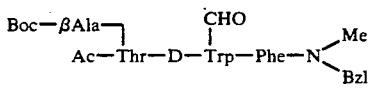

NMR (DMSO-d$_6$, δ) : 0.83 (3H, d, J=7Hz), 1.37 (9H, s), 1.87 (3H, s), 2.24 (2H, t, J=7Hz), 2.87 (3H, s), 2.6-3.0 (4H, m), 3.05 (2H, m), 4.30 and 4.68 (2H, ABq, J=15Hz), 4.4-5.1 (4H, m), 6.67 (1H, m), 6.95-7.55 (14H, m), 7.6 (1H, m), 7.90 (1H, d, J=8Hz), 8.1 (1H, m), 8.34 (1H, d, J=8Hz), 8.70 (1H, m), 9.25 (1H, br s).

EXAMPLE 79

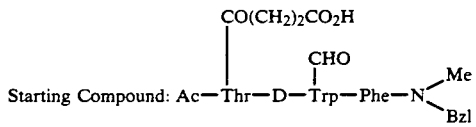

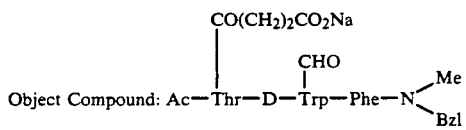

Ac-Thr(CO(CH$_2$)$_2$CO$_2$H)-D-Trp(CHO)-Phe-NMeBzl (482 mg) was dissolved in acetone (10 ml) and sodium 2-ethyl-hexanoate (111 mg) at room temperature. The mixture was stirred for 20 minutes at the same temperature, and the precipitates were collected, washed with acetone, and dried under vacuum to give Ac-Thr(CO(CH$_2$)$_2$CO$_2$Na)-D-Trp(CHO)-Phe-NMeBzl (300 mg).

IR (Nujol): 3250, 1740 (sh), 1710, 1640, 1590 cm$^{-1}$.
NMR (DMSO-d$_6$, δ): 0.80 (3H, d, J=6Hz), 1.85 (3H, s), 2.25 (4H, s), 2.78 and 2.81 (3H, s), 2.85-3.1 (4H, m), 4.2-5.0 (6H, m), 6.95-7.4 (13H, m), 7.6 (2H, m), 8.1 (2H, m), 8.9 (1H, d, J=7Hz), 9.2 (1H, m).

EXAMPLE 80

The following object compound was obtained from the corresponding starting compound according to a similar manner to that of Example 64.

Starting Compound: 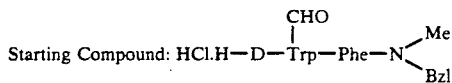

Object Compound: 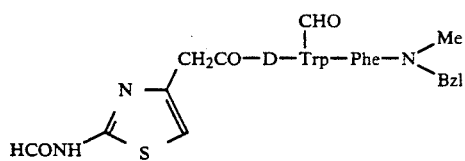

IR (Nujol): 3270, 3180, 1705, 1790, 1660, 1630 cm⁻¹.
NMR (DMSO-d₆, δ): 2.80 (2H, s), 2.88 (3H, s), 2.7–2.9 (2H, m), 3.47 (2H, s), 4.33 and 4.63 (2H, ABq, J=15Hz), 4.65 (1H, m), 5.04 (1H, m), 6.73 (1H, s), 7.0–7.5 (14H, m), 7.67 (1H, m), 8.20 (1H, d, J=8Hz), 8.45 (1H, s), 8.78 (1H, m), 9.25 (1H, br), 12.1 (1H, br).

EXAMPLE 81

Starting Compound: 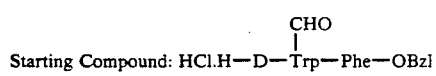

Object Compound: 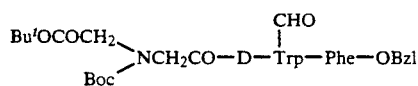

To an ice-cooled solution of HCl.H-D-Trp(CHO)-Phe-OBzl (800 mg) and NMM (162 mg) in DMF (15 ml) was added

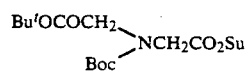

(618 mg). The solution was stirred for two hours under ice-cooling and for two and half hours at room temperature, and to the reaction mixture were added NMM (72 mg) and the active ester (50 mg). After stirring for additional three hours, N,N-dimethyl-1,3-propanediamine (3 drops) was added and the mixture was stirred further for an hour. After concentration, the product was extracted with ethyl acetate and the extract was washed successively with water, diluted sodium hydrogencarbonate solution, 0.5N hydrochloric acid, and sodium chloride solution, and dried over magnesium sulfate. The crude product was purified on a silica gel column (30 g) elution with chloroform-methanol (100:1) to give a purified product which was crystallized with diisopropyl ether to give

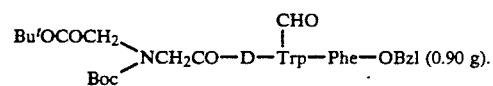

mp: 126°–127° C.
IR (Nujol): 3300, 1740, 1710, 1690, 1670, 1650 cm⁻¹.
NMR (CDCl₃, δ): 1.30, 1.36 and 1.46 (18H, s), 3.0–3.4 (4H, m), 3.6–4.2 (4H, m), 4.7–5.0 (2H, m), 5.10 (2H, s), 7.9 (1H, m), 7.1–7.5 (14H, m), 7.6 (1H, m), 8.4 (1H, d, J=7Hz), 9.1 (1H, br s).

EXAMPLE 82

The following compounds were obtained from the corresponding starting compounds according to a similar manner to that of Example 58.

(1)

Starting Compound: Z-D-Trp-Phe-OBzl

Object Compound: H-D-Trp-Phe-OH mp: ~249° C. (dec.).
IR (Nujol): 3250, 1690, 1605, 1535 cm⁻¹.
NMR (DMSO-d₆, δ): 2.6–3.3 (4H, m), 3.7–4.0 (1H, m), 4.2–4.6 (1H, m), 6.53 (3H, br s), 6.9–7.3 (8H, m), 7.23–7.5 (1H, m), 7.5–7.8 (1H, m), 8.3 (1H, broad), 10.95 (1H, s).
Elemental Analysis. Calculated for $C_{20}H_{21}N_3O_3$: C 68.36, H 6.02, N 11.96; Found: C 68.25, H 5.93, N 12.01.

(2)

Starting Compound: Boc-D-Trp-Phe-OBzl

Object Compound: Boc-D-Trp-Phe-OH mp: 190°–200° C.
IR (Nujol): 3400, 3300, 1720, 1680, 1650, 1525 cm⁻¹.
NMR (DMSO-d₆, δ): 1.29 (9H, s), 2.5–3.2 (4H, m), 3.27 (4H, broad, overlapped with H₂O), 4.0–4.6 (2H, m), 6.51 (1H, br d, J=8Hz), 6.8–7.0 (3H, m), 7.0–7.6 (2H, m), 7.17 (5H, s), 8.11 (1H, br d, J=8Hz), 10.62 (1H, s).
Elemental Analysis. Calculated for $C_{25}H_{29}N_3O_5$: C 66.50, H 6.47, N 9.31; Found: C 66.13, H 6.39, N 9.32.

EXAMPLE 83

The following object compound was obtained from the corresponding starting compound according to a similar manner to that of Example 8.

Starting Compound: 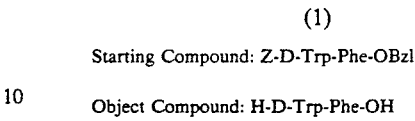

Object Compound: 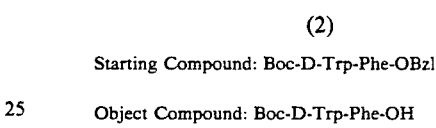

mp: 216°–218° C.
IR (Nujol): 3360, 1720, 1705, 1655, 1630, 1515 cm⁻¹.
NMR (DMSO-d₆, δ): 1.06 (s) and 1.26 (s)(9H), 2.5–3.1 (6H, m), 3.5–3.7 (1H, m), 3.7–3.9 (1H, m), 4.1–4.3 (1H, m), 4.4–4.8 (2H, m), 5.0–5.2 (1H, m), 6.8–7.0 (1H, m), 7.0–8.3 (14H, m), 8.5–8.8 (1H, m), 9.22 (s) and 9.61 (s)(1H).
Elemental Analysis. Calculated for $C_{35}H_{38}N_4O_5$: C 70.69, H 6.44, N 9.42; Found: C 70.33, H 6.46, N 9.32.

EXAMPLE 84

The following object compound was obtained from the corresponding starting compound according to a similar manner to that of Preparation 1-(1).

Starting Compound: 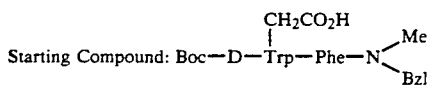

Object Compound: 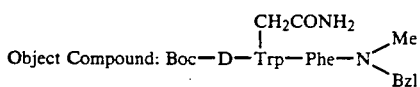

IR (CH$_2$Cl$_2$): 3490, 3400, 3350, 1710, 1695, 1670 (sh), 1640 cm$^{-1}$.

NMR (DMSO-d$_6$, δ): 1.29 (9H, s), 2.65–3.05 (4H, m), 2.78 and 2.88 (3H, s), 4.23 (1H, m), 4.41 and 4.57 (2H, ABq, J=14Hz), 4.68 (2H, s), 4.9–5.1 (1H, m), 6.6–6.75 (1H, m), 6.9–7.4 (16H, m), 7.6–7.8 (1H, m), 8.5–8.7 (1H, m).

EXAMPLE 85

The following object compounds were obtained from the corresponding starting compounds according to similar manners to those of Example 4 and Example 13, successively.

(1)

Starting Compound:

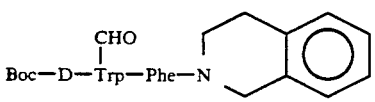

Object Compound:

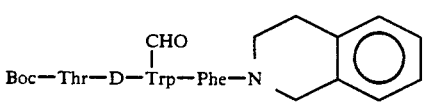

IR (Nujol): 3300, 1710, 1655–1625 cm$^{-1}$.

NMR (DMSO-d$_6$, δ): 1.7–1.9 (3H, m), 1.34 (9H, s), 2.5–3.1 (6H, m), 3.4–3.6 (1H, m), 3.6–3.9 (3H, m), 4.4–4.8 (4H, m), 5.0–5.1 (1H, m), 6.32 (1H, d, J=8Hz), 7.1–7.7 (13H, m), 7.9–8.3 (2H, m), 8.5–8.8 (1H, m), 9.13 (s) and 9.61 (s)(1H).

(2)

Starting Compound: 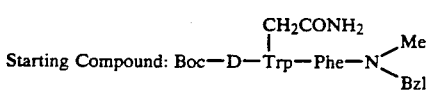

Object Compound: 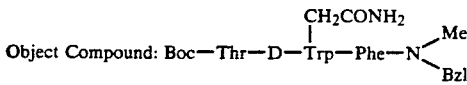

IR (Nujol): 3300, 1710 (sh), 1690 (sh), 1680 (sh), 1630 cm$^{-1}$.

NMR (DMSO-d$_6$, δ): 0.84 (3H, d, J=5.6Hz), 1.37 (9H, s), 2.76 and 2.84 (3H, s), 2.6–3.0 (4H, m), 3.7–3.95 (2H, m), 4.27–4.78 (6H, m), 4.85–5.0 (1H, m), 6.3 (1H, m), 6.95–7.4 (16H, m), 7.5–7.6 (1H, m), 7.9–8.0 (1H, m), 8.5–8.65 (1H, m).

Elemental Analysis. Calculated for C$_{39}$H$_{48}$N$_6$O$_7$·H$_2$O: C 64.09, H 6.90, N 11.50; Found: C 64.17, H 6.70, N 11.35.

EXAMPLE 86

The following object compound was obtained from the corresponding starting compound according to a similar manner to that of Example 23.

Starting Compound:

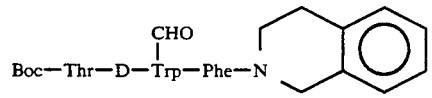

Object Compound:

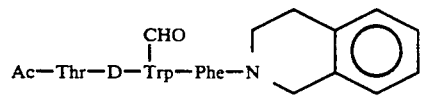

IR (Nujol): 3270, 1705, 1640, 1545 cm$^{-1}$.

NMR (DMSO-d$_6$, δ): 0.74 (3H, d, J=5Hz), 1.84 (3H, s), 2.5–3.1 (6H, m), 3.4–3.6 (1H, m), 3.6–3.9 (2H, m), 4.0–4.1 (1H, m), 4.4–4.8 (4H, m), 4.95–5.1 (1H, m), 7.1–7.5 (12H, m), 7.5–7.8 (2H, m), 7.9–8.3 (2H, m), 8.6–8.8 (1H, m), 9.14 (s) and 9.60 (s)(1H).

EXAMPLE 87

The following object compounds were obtained from the corresponding starting compounds according to a similar manner to that of Example 13.

(1)

Starting Compound: 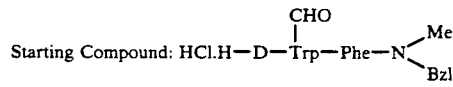

Object Compound:

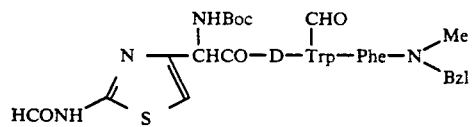

IR (Nujol): 3300, 1710, 1690, 1670, 1655 (sh), 1640, 1630, 1545 cm$^{-1}$.

NMR (DMSO-d$_6$, δ): 1.34 and 1.36 (9H, s), 2.7–3.1 (7H, m), 4.3–4.5 (1H, m), 4.6–4.8 (2H, m), 4.9–5.2 (1H, m), 5.24 (1H, d, J=8Hz), 6.68 (1H, d, J=8Hz), 7.0–7.4 (15H, m), 7.64 (1H, m), 8.22 (1H, m), 8.44 and 8.49 (1H, s), 8.7–9.2 (1H, m), 12.2–12.4 (1H, m).

(2)

Starting Compound: 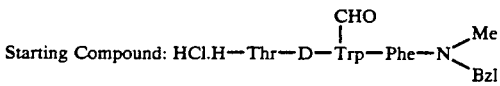

Object Compound: 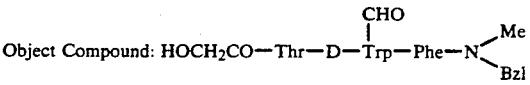

IR (Nujol): 3300, 1710, 1640, 1535 cm$^{-1}$.

NMR (DMSO-d$_6$, δ): 0.71 (3H, br), 2.80 and 2.89 (3H, s), 2.6–3.1 (4H, m), 3.18 (1H, br), 3.86 (2H, s), 4.1–4.2 (1H, m), 4.5–4.8 (2H, m), 4.82–5.05 (2H, m), 5.7 (1H, br), 7.0–7.4 (13H, m), 7.4–7.6 (1H, m), 7.7 (1H, br), 7.9–8.3

(2H, m), 8.70 and 8.80 (1H, d, J=8Hz), 9.15 and 9.60 (1H, s).

EXAMPLE 88

The following object compounds were obtained from the corresponding starting compounds according to similar manners to those of Example 2 and Example 17, successively.

(1)

Starting Compound:

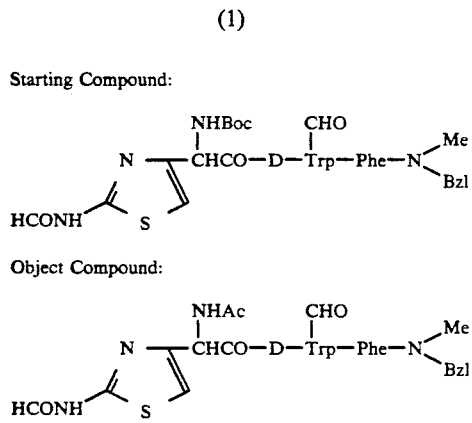

Object Compound:

The product was a mixture of two enantiomers and used in the next reaction without separation.

This crude product was suspended in ethyl acetate and heated with water bath under reflux. After cooling to room temperature, the precipitates were collected, washed with ethyl acetate, and dried to give one of the enantiomers (HPLC RT=4.7 min, isomer A). The filtrate was applied to silica gel column and eluted with chloroform-methanol (100:3) to give another enantiomer (HPLC RT=5.1 min, isomer B) which was triturated with diisopropyl ether.

isomer A
mp: 218°–220° C.
IR (Nujol): 3280, 1690, 1670 (sh), 1645 (sh), 1632, 1535 cm$^{-1}$.
NMR (DMSO-d$_6$, δ): 1.845 (3H, s), 2.82 and 2.92 (3H, s), 2.6–3.1 (4H, m), 4.33–4.40 and 4.53–4.80 (3H, m), 5.0 (1H, m), 5.50 (1H, d, J=8Hz), 6.5–6.75 (1H, m), 7.0–7.4 (13H, m), 7.68 (1H, br s), 7.9–8.4 (3H, m), 8.44 (1H, s), 8.79 and 8.88 (1H, d, J=8Hz), 9.05 and 9.58 (1H, br s), 12.21 (1H, s).

isomer B
IR (3288-16): 3280, 1715–1610, 1550–1510 cm$^{-1}$.
NMR (DMSO-d$_6$, δ): 1.88 (3H, s), 2.81 and 2.89 (3H, s), 2.7–3.1 (4H, m), (3288-15) 4.3–4.8 (3H, m), 4.9–5.1 (1H, m), 5.56 (1H, d, J=8Hz), 7.0–7.4 (13H, m), 7.5–7.7 (2H, m), 8.0–8.8, 9.17 and 9.62 (5H, m), 12.41 and 12.80 (1H, m).

(2)

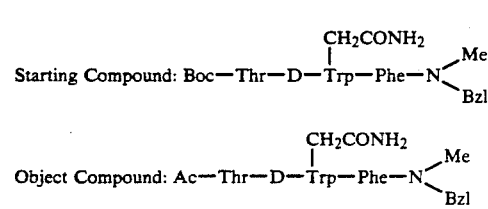

mp: 230°–232° C. (dec.).
IR (Nujol): 3390, 3290, 1680, 1670 (sh), 1635, 1530 cm$^{-1}$.

NMR (DMSO-d$_6$, δ): 0.8 (3H, m), 1.87 (3H, s), 2.77 and 2.85 (3H, s), 2.7–3.14 (4H, m), 3.8 (1H, m), 4.1 (1H, m), 4.3–4.8 (6H, m), 4.85–5.0 (1H, m), 6.95–7.4 (17H, m), 7.6 (1H, m), 7.8–8.0 (2H, m), 8.5–8.7 (1H, m).

Elemental Analysis. Calculated for C$_{30}$H$_{42}$N$_6$O$_6$·H$_2$O: C 64.27, H 6.59, N 12.49; Found: C 64.69, H 6.60, N 12.64.

EXAMPLE 89

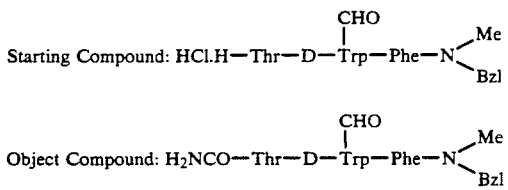

To a solution of HCl.H-Thr-D-Trp(CHO)-Phe-NMeBzl (0.94 g) and triethylamine (0.153 g) in acetonitrile (12 ml), was added chlorosulfonyl isocyanate (0.214 g) under cooling with Dry ice and carbon tetrachloride bath. The solution was stirred at the same temperature for an hour and then stirred under ice-cooling. Chlorosulfonyl isocyanate (0.214 g) was added at this temperature, after stirring for fifteen minutes, water (3 ml) was added. The pH was adjusted to pH 4 with sodium hydrogencarbonate and the mixture was stirred for an hour. After evaporation of acetonitrile, the product was extracted with ethyl acetate under saturation with sodium chloride. The organic layer was washed with sodium chloride solution and concentrated. The residue was dissolved in CH$_3$CN-H$_2$O (8:2) (20 ml) and applied to a column of ®TOYO PEARL HW-40 (26 mmφ, 400 ml) and eluted with CH$_3$CH-H$_2$O (7:3), and fractionated. The main fraction was collected, and after evaporation of acetonitrile, n-butanol and ethyl acetate was added and the organic layer was separated and concentrated to give H$_2$NCO-Thr-D-Trp(CHO)-Phe-NMeBzl (600 mg).

NMR (DMSO-d$_6$, δ): 0.6–0.8 (3H, m), 2.83 and 2.92 (3H, s), 2.7–3.1 (4H, m), 3.84 (1H, d, J=5Hz), 4.1–4.4 and 4.5–5.1 (4H, m), 7.0–7.4 (15H, m), 7.5–7.9 (1H, m), 8.2–8.6 (3H, m), 8.9–9.6 (1H, m).

Column: Lichrosob RP-18 (4×250 nm),
Eluant: MeOH-H$_2$O (75:25) 0.1% trifluoroacetic acid,
Flow rate: 1.5 ml/min, Detection: UV 254 nm

EXAMPLE 90

The following object compound was obtained from the corresponding starting compound according to a similar manner to that of Example 13.

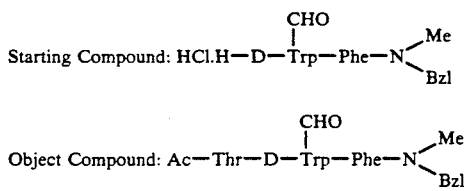

IR (Nujol): 3450 (sh), 3260, 1720 (sh), 1698, 1660 (sh), 1645–1620 (broad), 1550 cm$^{-1}$.

NMR (DMSO-d$_6$, δ): 0.80 (3H, d, J=6Hz), 1.87 (3H, s), 2.80 (s) and 2.87 (s)(3H), 2.6–3.2 (4H, m), 3.6–3.9 (1H, m), 3.95–4.3 (1H, m), 4.3–5.2 (5H, m), 6.95–7.8 (15H, m), 7.8–8.3 (2H, m), 8.5–8.75 (1H, m), 9.0–9.7 (1H, br s).

EXAMPLE 91

The following object compound was obtained from the corresponding starting compound according to similar manners to those of Example 13 and Example 71, successively.

What we claims is:

1. A compound of the formula:

$R^1$—A—D—Trp($R^2$)—Phe—$R^3$ wherein $R^1$ is hydrogen, carbamoyl, lower alkoxycarbonyl, lower alkanoyl, ar(lower)alkoxycarbonyl, carbamoyl(lower)alkanoyl, lower alkoxalyl, di(lower)alkylamino(lower)alkanoyl, N-ar(lower)alkyl-N-lower alkoxycarbonylamino(lower)alkanoyl, tetrazolyl(lower)alkanoyl, carboxy(lower)alkanoyl, hydroxy(lower)alkanoyl, morpholinecarbonyl, N-lower alkylcarbamoyl, lower alkanoylaminothiazolyl(lower)alkanoyl, lower alkanoylaminothiazolyl(lower)alkanoyl having lower alkoxycarbonylamino or lower alkanoylamino on the alkanoyl moiety, carboxy(lower) alkylamino(lower)alkanoyl, ar(lower)alkylamino(lower)alkanoyl or N-lower alkoxycarbonyl-N-lower alkoxycarbonyl(lower)alkylamino(lower)alkanoyl, $R^2$ is hydrogen, lower alkanoyl, arenesulfonyl, carbamoyl(lower)alkyl, carboxy(lower)alkyl or lower alkoxycarbonyl(lower)alkyl, $R^3$ is a group of the formula:

wherein $R^4$ is hydrogen, lower alkyl, hydroxy(lower)alkyl or ar(lower)alkoxycarbonyloxy(lower)alkyl, and $R^5$ is aryl, ar(lower)alkyl or haloar(lower)alkyl, or a group of the formula:

—O$R^6$ wherein $R^6$ is aryl, lower alkyl, ar(lower)alkyl, haloar(lower)alkyl or pyridyl(lower)alkyl, and A is one amino acid residue selected from Gln Ser, Asn Thr, D-Gln, Lys, His, βAsp, Orn, Glyn Hyp, pGlu, Glu,

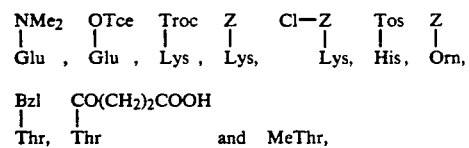

wherein

Z is benzyloxycarbonyl or a pharmaceutically acceptable salt thereof.

2. A compound of claim 1, wherein $R^1$ is hydrogen, t-butoxycarbonyl, formyl, benzyloxycarbonyl, acetyl, succinamoyl, t-butoxalyl, 3-diethylaminopropionyl, diethylaminoacetyl, 2-benzyl-t-butoxycarbonylaminoacetyl, (1H-tetrazol-1-yl)acetyl, 5-carboxyvaleryl, 4-carboxybutyryl, 3-carboxypropionyl, 4-morpholinecarbonyl, t-butylcarbamoyl, (2-formamidothiazol-4-yl)acetyl, oxalo, carboxymethylaminoacetyl, benzylaminoacetyl or N-t-butoxycarbonyl-N-t-butoxycarbonylmethylaminoacetyl, $R^2$ is hydrogen, formyl, tosyl, carbamoylmethyl, carboxymethyl or ethoxycarbonylmethyl, and $R^3$ is a group of the formula:

wherein $R^4$ is hydrogen, methyl, ethyl, hydroxyethyl or benzyloxycarbonyloxyethyl, and $R^5$ is phenyl, benzyl or O-fluorobenzyl.

3. A compound of claim 2, which is selected from the group consisting of:
Boc-Gln-D-Trp(CHO)-Phe-NMeBzl,
Boc-Thr-D-Trp(CHO)-Phe-NMeBzl,
Boc-Glu(NMe$_2$)-D-Trp(CHO)-Phe-NMeBzl,
Ac-Thr-D-Trp(CHO)-Phe-NMeBzl, and
Ac-Glu(NMe$_2$)-D-Trp(CHO)-Phe-NMeBzl.

4. A compound of claim 1, wherein $R^1$ is hydrogen, t-butoxycarbonyl, formyl, benzyloxycarbonyl, acetyl, succinamoyl, t-butoxalyl, 3-diethylaminopropionyl, diethylaminoacetyl, 2-benzyl-t-butoxycarbonylaminoacetyl, (1H-tetrazol-1-yl)acetyl, 5-carboxyvaleryl, 4-carboxybutyryl, 3-carboxypropionyl, 4-morpholinecarbonyl, t-butylcarbamoyl, (2-formamidothiazol-4-yl)acetyl, oxalo, carboxymethylaminoacetyl, benzylaminoacetyl or N-t-butoxycarbonyl-N-t-butoxycarbonylmethylaminoacetyl, $R^2$ is hydrogen, formyl, tosyl, carbamoylmethyl, carboxymethyl or ethoxycarbonylmethyl, and $R^3$ is a group of the formula:

—O$R^6$ wherein $R^6$ is phenyl, methyl, isopropyl, benzyl, phenethyl, p-chlorobenzyl, 2-pyridylmethyl, 3-pyridylmethyl or 4-pyridylmethyl.

5. A compound of claim 4, which is selected from the group consisting of:
Boc-Gln-D-Trp(CHO)-Phe-OBzl,
Ac-Gln-D-Trp(CHO)-Phe-OBzl,
Z-Gln-D-Trp(CHO)-Phe-OBzl,
Boc-Asn-D-Trp(CHO)-Phe-OBzl,
Boc-Ser-D-Trp(CHO)-Phe-OBzl,
Boc-Glu(NMe$_2$)-D-Trp(CHO)-Phe-OBzl, and
Boc-Thr-D-Trp(CHO)-Phe-OBzl.

* * * * *